United States Patent
Butt et al.

(10) Patent No.: US 8,691,958 B2
(45) Date of Patent: Apr. 8, 2014

(54) METHODS AND COMPOSITIONS FOR ENHANCED PROTEIN EXPRESSION AND PURIFICATION

(75) Inventors: Tauseef R. Butt, Malvern, PA (US); Tadas Panavas, Wayne, PA (US); Amolkumar Karwa, Paoli, PA (US); Raymond J. Peroutka, Philadelphia, PA (US); Jeffrey G. Marblestone, Philadelphia, PA (US)

(73) Assignees: Progenra, Inc., Malvern, PA (US); Lifesensors, Inc., Malvern, PA (US)

( * ) Notice: Subject to any disclaimer, the term of this patent is extended or adjusted under 35 U.S.C. 154(b) by 767 days.

(21) Appl. No.: 12/521,468

(22) PCT Filed: Dec. 28, 2007

(86) PCT No.: PCT/US2007/089035
§ 371 (c)(1),
(2), (4) Date: Jun. 1, 2010

(87) PCT Pub. No.: WO2008/083271
PCT Pub. Date: Jul. 10, 2008

(65) Prior Publication Data
US 2012/0065106 A1    Mar. 15, 2012

Related U.S. Application Data

(60) Provisional application No. 60/877,914, filed on Dec. 29, 2006.

(51) Int. Cl.
*C07H 21/04* (2006.01)
*C12N 15/63* (2006.01)
*C12N 15/85* (2006.01)
*C12N 9/00* (2006.01)

(52) U.S. Cl.
USPC ........ 536/23.1; 435/320.1; 435/325; 435/183

(58) Field of Classification Search
None
See application file for complete search history.

(56) References Cited

FOREIGN PATENT DOCUMENTS

WO    2006073976    7/2006

OTHER PUBLICATIONS

Bork (Genome Research, 10:348-400, 2000).*
Smith et al (Nature Biotechnology 15:1222-1223, 1997).*
Brenner (TIG 15:132-133, 1999).*
Broun et al. (Science 282:1315-1317, 1998).*
Van de Loo et al. (Proc. Natl. Acad. Sci. 92:6743-6747, 1995).*
Kim, K.I., et al. "Versatile protein tag, SUMO: its enzymology and biological function." J Cell Physiol. Jun. 2002;191 (3):257-68.
Marblestone, J.G., et al. "Comparison of SUMO fusion technology with traditional gene fusion systems: enhanced expression and solubility with SUMO." Protein Sci. Jan. 2006;15(1):182-9. Epub Dec. 1, 2005.
Malakhov, M.P., et al. "SUMO fusions and SUMO-specific protease for efficient expression and purification of proteins." J Struct Funct Genomics. 2004;5(1-2):75-86.
Peroutka, R.J., et al. "Enhanced protein expression in mammalian cells using engineered SUMO fusions: secreted phospholipase A2." Protein Sci. Sep. 2008;17(9):1586-95. Epub Jun. 6, 2008.
Liu, L., et al. "Enhanced protein expression in the baculovirus/insect cell system using engineered SUMO fusions." Protein Expr Purif. Nov. 2008;62(1):21-8. Epub Aug. 5, 2008.
Kono, K., et al. "The mobility of Bach2 nuclear foci is regulated by SUMO-1 modification." Experimental Cell Research, 314: 903-913 (2003).

* cited by examiner

*Primary Examiner* — Celine Qian
(74) *Attorney, Agent, or Firm* — Robert C. Netter, Jr.; Dann, Dorfman, Herrell & Skillman

(57) ABSTRACT

Methods for enhancing expression levels, secretion, and purification of heterologous fusion proteins in a host cell are disclosed.

15 Claims, 23 Drawing Sheets

A. β-lactamase in a complex -> Ampicilin sensitivity
B. β-lactamase free -> Ampicilin resistance
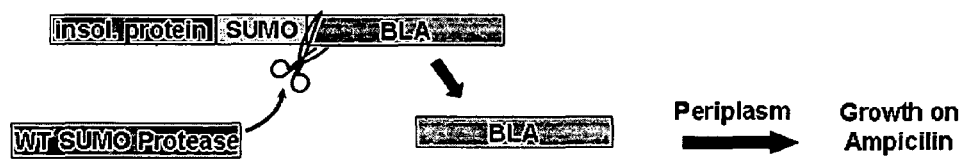
C. WT SUMO protease + mutant SUMO* -> Ampicilin sensitivity
D. SUMO* protease + mutant SUMO* -> Ampicilin resistance
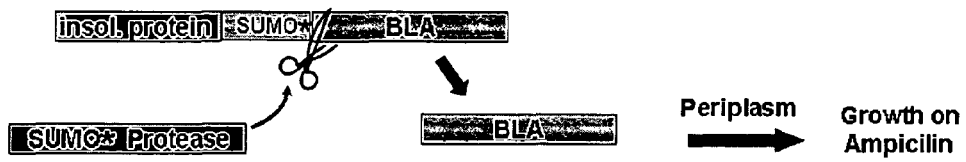
Figure 7

Sacharomyces cerevisiae Smt3 (GenBank Accession No. AY558174.1; SEQ ID NO: 67)

```
Met Ser Asp Ser Glu Val Asn Gln Glu Ala Lys Pro Glu Val Lys Pro
 1               5                   10                  15
Glu Val Lys Pro Glu Thr His Ile Asn Leu Lys Val Ser Asp Gly Ser
                20                  25                  30
Ser Glu Ile Phe Phe Lys Ile Lys Lys Thr Thr Pro Leu Arg Arg Leu
                35              40                  45
Met Glu Ala Phe Ala Lys Arg Gln Gly Lys Glu Met Asp Ser Leu Arg
        50              55                  60
Phe Leu Tyr Asp Gly Ile Arg Ile Gln Ala Asp Gln Thr Pro Glu Asp
65                      70                  75                  80
Leu Asp Met Glu Asp Asn Asp Ile Ile Glu Ala His Arg Glu Gln Ile
                85                  90                  95
Gly Gly Ala Thr Tyr
                100
```

Xenopus laevis Smt3 (GenBank Accession No. BC045271.1; SEQ ID NO: 68)

```
Met Ala Asp Asp Lys Pro Lys Glu Gly Val Lys Thr Glu Asn Asn Asp
 1               5                   10                  15
His Ile Asn Leu Lys Val Ala Gly Gln Asp Gly Ser Val Val Gln Phe
                20                  25                  30
Lys Ile Lys Arg Gln Thr Pro Leu Ser Lys Leu Met Lys Ala Tyr Cys
            35                  40                  45
Glu Arg Gln Gly Leu Ser Met Arg Gln Ile Arg Phe Arg Phe Asp Gly
        50              55                  60
Gln Pro Ile Asn Glu Thr Asp Thr Pro Ala Gln Leu Glu Met Glu Asp
65                      70                  75                  80
Glu Asp Thr Ile Asp Val Phe Gln Gln Gln Thr Gly Gly Ser Phe
                85                  90                  95
```

Homo Sapiens SUMO1 (GenBank Accession No. BT006632.1; SEQ ID NO: 69)

```
Met Ser Asp Gln Glu Ala Lys Pro Ser Thr Glu Asp Leu Gly Asp Lys
 1               5                   10                  15
Lys Glu Gly Glu Tyr Ile Lys Leu Lys Val Ile Gly Gln Asp Ser Ser
                20                  25                  30
Glu Ile His Phe Lys Val Lys Met Thr Thr His Leu Lys Lys Leu Lys
                35              40                  45
Glu Ser Tyr Cys Gln Arg Gln Gly Val Pro Met Asn Ser Leu Arg Phe
        50              55                  60
Leu Phe Glu Gly Gln Arg Ile Ala Asp Asn His Thr Pro Lys Glu Leu
65                      70                  75                  80
Gly Met Glu Glu Glu Asp Val Ile Glu Val Tyr Gln Glu Gln Thr Gly
                85                  90                  95
Gly His Ser Thr Val
                100
```

Figure 11A

Homo Sapiens –SUMO2 (GenBank Accession No. BC070159.1; SEQ ID NO: 70)

```
Met Ala Asp Glu Lys Pro Lys Glu Gly Val Lys Thr Glu Asn Asn Asp
1               5                   10                  15
His Ile Asn Leu Lys Val Ala Gly Gln Asp Gly Ser Val Val Gln Phe
            20                  25                  30
Lys Ile Lys Arg His Thr Pro Leu Ser Lys Leu Met Lys Ala Tyr Cys
        35                  40                  45
Glu Arg Gln Gly Leu Ser Met Arg Gln Ile Arg Phe Arg Phe Asp Gly
    50                  55                      60
Gln Pro Ile Asn Glu Thr Asp Thr Pro Ala Gln Leu Glu Met Glu Asp
65                  70                  75                  80
Glu Asp Thr Ile Asp Val Phe Gln Gln Gln Thr Gly Gly Val Tyr
                85                  90                  95
```

Homo Sapiens –SUMO3 (GenBank Accession No. NM_006936.2; SEQ ID NO: 71)

```
Met Ser Glu Glu Lys Pro Lys Glu Gly Val Lys Thr Glu Asn Asp His
1               5                   10                  15
Ile Asn Leu Lys Val Ala Gly Gln Asp Gly Ser Val Val Gln Phe Lys
            20                  25                  30
Ile Lys Arg His Thr Pro Leu Ser Lys Leu Met Lys Ala Tyr Cys Glu
        35                  40                  45
Arg Gln Gly Leu Ser Met Arg Gln Ile Arg Phe Arg Phe Asp Gly Gln
    50                  55                      60
Pro Ile Asn Glu Thr Asp Thr Pro Ala Gln Leu Glu Met Glu Asp Glu
65                  70                  75                  80
Asp Thr Ile Asp Val Phe Gln Gln Gln Thr Gly Gly Val Pro Glu Ser
                85                  90                  95
Ser Leu Ala Gly His Ser Phe
                100
```

Drosophila Melanogaster Smt3 (GenBank Accession No. NM_058063.3; SEQ ID NO: 72)

```
Met Ser Asp Glu Lys Lys Gly Gly Glu Thr Glu His Ile Asn Leu Lys
1               5                   10                  15
Val Leu Gly Gln Asp Asn Ala Val Val Gln Phe Lys Ile Lys Lys His
            20                  25                  30
Thr Pro Leu Arg Lys Leu Met Asn Ala Tyr Cys Asp Arg Ala Gly Leu
        35                  40                  45
Ser Met Gln Val Val Arg Phe Arg Phe Asp Gly Gln Pro Ile Asn Glu
    50                  55                      60
Asn Asp Thr Pro Thr Ser Leu Glu Met Glu Glu Gly Asp Thr Ile Glu
65                  70                  75                  80
Val Tyr Gln Gln Gln Thr Gly Gly Ala Pro
                85                  90
```

Figure 11B

Arabidopsis Thaliana SUMO1 (GenBank Accession No. NM_118818.2; SEQ ID NO: 73)

```
Met Ser Ala Asn Gln Glu Glu Asp Lys Lys Pro Gly Asp Gly Gly Ala
1               5                   10                  15
His Ile Asn Leu Lys Val Lys Gly Gln Asp Gly Asn Glu Val Phe Phe
                20                  25                  30
Arg Ile Lys Arg Ser Thr Gln Leu Lys Lys Leu Met Asn Ala Tyr Cys
                35                  40                  45
Asp Arg Gln Ser Val Asp Met Asn Ser Ile Ala Phe Leu Phe Asp Gly
            50              55                  60
Arg Arg Leu Arg Ala Glu Gln Thr Pro Asp Glu Leu Asp Met Glu Asp
65                      70                  75                  80
Gly Asp Glu Ile Asp Ala Met Leu His Gln Thr Gly Gly Ser Gly Gly
                85                  90                  95
Gly Ala Thr Ala
            100
```

Arabidopsis Thaliana SUMO2 (GenBank Accession No. NM_124898.2; SEQ ID NO: 74)

```
Met Ser Ala Thr Pro Glu Glu Asp Lys Lys Pro Asp Gln Gly Ala His
1               5                   10                  15
Ile Asn Leu Lys Val Lys Gly Gln Asp Gly Asn Glu Val Phe Phe Arg
                20                  25                  30
Ile Lys Arg Ser Thr Gln Leu Lys Lys Leu Met Asn Ala Tyr Cys Asp
                35                  40                  45
Arg Gln Ser Val Asp Phe Asn Ser Ile Ala Phe Leu Phe Asp Gly Arg
            50              55                  60
Arg Leu Arg Ala Glu Gln Thr Pro Asp Glu Leu Glu Met Glu Asp Gly
65                      70                  75                  80
Asp Glu Ile Asp Ala Met Leu His Gln Thr Gly Gly Gly Ala Lys Asn
                85                  90                  95
Gly Leu Lys Leu Phe Cys Phe
            100
```

Homo Sapiens –SUMO4 (GenBank Accession No. NP_001002255.1; SEQ ID NO: 75)

```
Met Ala Asn Glu Lys Pro Thr Glu Glu Val Lys Thr Glu Asn Asn Asn
1               5                   10                  15
His Ile Asn Leu Lys Val Ala Gly Gln Asp Gly Ser Val Val Gln Phe
                20                  25                  30
Lys Ile Lys Arg Gln Thr Pro Leu Ser Lys Leu Met Lys Ala Tyr Cys
                35                  40                  45
Glu Pro Arg Gly Leu Ser Val Lys Gln Ile Arg Phe Arg Phe Gly Gly
            50              55                  60
Gln Pro Ile Ser Gly Thr Asp Lys Pro Ala Gln Leu Glu Met Glu Asp
65                      70                  75                  80
Glu Asp Thr Ile Asp Val Phe Gln Gln Pro Thr Gly Gly Val Tyr
                85                  90                  95
```

Figure 11C

Sacharomyces cerevisiae ULP1 (GenBank Accession No. AAB68167.1; SEQ ID NO: 76)

```
  1 MSVEVDKHRN TLQYHKKNPY SPLFSPISTY RCYPRVLNNP SESRRSASFS GIYKKRTNTS
 61 RFNYLNDRRV LSMEESMKDG SDRASKAGFI GGIRETLWNS GKYLWHTFVK NEPRNFDGSE
 21 VEASGNSDVE SRSSGSRSSD VPYGLRENYS SDTRKHKFDT STWALPNKRR RIESEGVGTP
181 STSPISSLAS QKSNCDSDNS ITFSRDPFGW NKWKTSAIGS NSENNTSDQK NSYDRRQYGT
241 AFIRKKKVAK QNINNTKLVS RAQSEEVTYL RQIFNGEYKV PKILKEERER QLKLMDMDKE
301 KDTGLKKSII DLTEKIKTIL IENNKNRLQT RNENDDDLVF VKEKKISSLE RKHKDYLNQK
361 LKFDRSILEF EKDFKRYNEI LNERKKIQED LKKKKEQLAK KKLVPELNEK DDDQVQKALA
421 SRENTQLMNR DNIEITVRDF KTLAPRRWLN DTIIEFFMKY IEKSTPNTVA FNSFFYTNLS
481 ERGYQGVRRW MKRKKTQIDK LDKIFTPINL NQSHWALGII DLKKKTIGYV DSLSNGPNAM
541 SFAILTDLQK YVMEESKHTI GEDFDLIHLD CPQQPNGYDC GIYVCMNTLY GSADAPLDFD
601 YKDAIRMRRF IAHLILTDAL K
```

Homo Sapiens ULP1 (GenBank Accession No. NP_055369; SEQ ID NO: 77)

```
  1 MDDIADRMRM DAGEVTLVNH NSVFKTHLLP QTGFPEDQLS LSDQQILSSR QGHLDRSFTC
 61 STRSAAYNPS YYSDNPSSDS FLGSGDLRTF GQSANGQWRN STPSSSSSLQ KSRNSRSLYL
121 ETRKTSSGLS NSFAGKSNHH CHVSAYEKSF PIKPVPSPSW SGSCRRSLLS PKKTQRRHVS
181 TAEETVQEEE REIYRQLLQM VTGKQFTIAK PTTHFPLHLS RCLSSSKNTL KDSLFKNGNS
241 CASQIIGSDT SSSGSASILT NQEQLSHSVY SLSSYTPDVA FGSKDSGTLH HPHHHHSVPH
301 QPDNLAASNT QSEGSDSVIL LKVKDSQTPT PSSTFFQAEL WIKELTSVYD SRARERLRQI
361 EEQKALALQL QNQRLQEREH SVHDSVELHL RVPLEKEIPV TVVQETQKKG HKLTDSEDEF
421 PEITEEMEKE IKNVFRNGNQ DEVLSEAFRL TITRKDIQTL NHLNWLNDEI INFYMNMLME
481 RSKEKGLPSV HAFNTFFFTK LKTAGYQAVK RWTKKVDVFS VDILLVPIHL GVHWCLAVVD
541 FRKKNITYYD SMGGINNEAC RILLQYLKQE SIDKKRKEFD TNGWQLFSKK SQIPQQMNGS
601 DCGMFACKYA DCITKDRPIN FTQQHMPYFR KRMVWEILHR KLL
```

Homo Sapiens ULP2 (GenBank Accession No. NP_067640; SEQ ID NO: 78)

```
  1 MYRWLVRILG TIFRFCDRSV PPARALLKRR RSDSTLFSTV DTDEIPAKRP RLDCFIHQVK
 61 NSLYNAASLF GFPFQLTTKP MVTSACNGTR NVAPSGEVFS NSSSCELTGS GSWNNMLKLG
121 NKSPNGISDY PKIRVTVTRD QPRRVLPSFG FTLNSEGCNR RPGGRHSKG NPESSLMWKP
181 QEQAVTEMIS EESGKGLRRP HCTVEEGVQK EEREKYRKLL ERLKESGHGN SVCPVTSNYH
241 SSQRSQMDTL KTKGWGEEQN HGVKTTQFVP KQYRLVETRG PLCSLRSEKR CSKGKITDTE
301 TMVGIRFENE SRRGYQLEPD LSEEVSARLR LGSGSNGLLR RKVSIIETKE KNCSGKERDR
361 RTDDLLELTE DMEKEISNAL GHGPQDEILS SAFKLRITRG DIQTLKNYHW LNDEVINFYM
421 NLLVERNKKQ GYPALHVFST FFYPKLKSGG YQAVKRWTKG VNLFEQEIIL VPIHRKVHWS
481 LVVIDLRKKC LKYLDSMGQK GHRICEILLQ YLQDESKTKR NSDLNLLEWT HHSMKPHEIP
541 QQLNGSDCGM FTCKYADYIS RDKPITFTQH QMPLFRKKMV WEILHQQLL
```

Figure 12A

Drospohila Melanogaster ULP1 (GenBank Accession No. NP_067640; SEQ ID NO: 79)

```
   1 MSLPPEDTDL STNSAYESAL QIASNVSAAR VVGSAVGQRF SPSPAAHPNV IERVASHVDS
  61 RRSTFPSWGN PSVAPRGSEE AAANATATQL LWAENQGLPT SHLLPTEQAF ETLNTNAYCS
 121 PPGDSRFTFP SQNYSPLLPR CVPVPNQRYS PDGSPIHQLH ELQNCPLIDS PIRLRFPSPL
 181 PEPPSLPTIT LTVDALIDLD QNNQVAYYVQ QYNNQPVLYQ QNIHIGTGIQ LCDQASENNQ
 241 PIILHIVEHN PQTITESQEQ FHQVVPEIQI NNIQEQDQKF ENGISEQNHP IATEAQDQTL
 301 TEIRDENQIV LAVQEKNLTR ASEIQDQNQQ TLTEIPEKCL QIASPVTTDI QVQSPQVVIE
 361 IQEQNHQSVT EIQEEVHQTA PEIQVNVFQT SSDIQGQNHQ IVTEEQNHQT ITETQEDYSA
 421 VSEIQWENLS FSAEIQEQNQ QIVTEVTKLA SPSVTDIQAQ SPQSVIEIQD DDDEDLKFES
 481 DDLHTIPEIQ EKNQQSPQFV IEIHYDNEDL KFASDNQEQD QQTAELQKER FQFASEIEKR
 541 DLQIVTDTHK QNYHNVTDIP FATYIQEENE QLTPEDQEED QHYLNFEGNQ QFQLQKQDQL
 601 SVPQIQKQTH QFESKVKKRK LQPFSEYQQK GQKDHIQERQ YIQQEFTIHS NQAYSKVQYI
 661 QTIQTATPYV PQLEISQENS FEVQPAYEVN EGQRDRELVS YTGHEHQNFV DEVSTPLPPA
 721 EAQPGSTSED ISDPVSPEHW EQLESLDPST ICIRKTFNLI RDISESLVAD PEQPEAEAHR
 781 KSIFLLRQKL ADVCHKVLTE IIHGRATDEI ISILREILEQ TKEIPPRPTP KRDLQEDISM
 841 GLEILKKIRG MLSGWYSSRE SETDSTDTGT GFQAQNGKGF GAGRQPENSF LSQKRRNQEE
 901 NPRLIKYRRV DNSFPRLITN ETAEDLIPNN SMAKRDQPQS SKRLSIFNPP VYTQHRVRND
 961 APHVPTPFDD EESSQRLANA GPSSRPMTYS DAVRLGHNGI SESRVNGHSS HTVRREPSRL
1021 HRSILSHEMN CKDQEQYNEL IRTQTNYVGS RYLKPGTPPT FQRAKAQSAT SSSCSLQDNQ
1081 SNITDSFPSP HGRANPELTE YAKLINRQEN EENRSPAPQQ PKRNASNSSA SHASTISSSA
1141 SSSCSTCSTC SSSDTEPMLV KDSPEVKEAN EANEANEANE ANETKENDAP QPTTTRIKKP
1201 DFLHRRFANC IFLRNDFAEN FKARANRRQL ESMHLLGIAE QQANESKDER LAYEKKLREV
1261 MFRSGAPHRP FFEIGPLEQP EEKKETKLIP LTKEDHARFQ EMTTIEVTTN LIFKYNLQIT
1321 TDDIFTFVDG EWLNDAIINF YMSMLTERSE KRAGELPATY AMNTFFMPRL LQAGYAGVRR
1381 WTRKVDLFSK DIIPVPVHCG NVHWCMAIIH LRNKTIFYYD SMGRPNQPAL DALVKYLHEE
1441 SLDKRKQPFD MTGFVVENAQ NIPRQGNSSD CGVFSCMFAE YITRDVPITF SQAEMLYFRT
1501 KMALEIADGK LWQ
```

Arabidopsis Thaliana ULP1 (GenBank Accession No. NP_191978; SEQ ID NO: 80)

```
   1 MFVDAMQDLA LVNSALSKRN RKKILVSHKN SNIDISGETL QCLRPNQWLN DDVTNLYLEL
  61 LKERQTRDPQ KYFKCHFFNT FFYVKLVSGS GYNYKAVSRW TTKRKLGYDL IDCDIIFVPI
 121 HIDIHWTLGV INNRERKFVY LDSLFTGVGH TILNAMAKYL VDEVKQKSQK NIDVSSWGME
 181 YVEERPQQQN GYDCGMFMLK YIDFYSRGLS LQFSQVIRDV IKKDMPYFRL RTAKEILRLR
 241 AD
```

Figure 12B

```
                         SEQUENCE LISTING

<160> NUMBER OF SEQ ID NOS: 80

<210> SEQ ID NO 1
<211> LENGTH: 98
<212> TYPE: PRT
<213> ORGANISM: Artificial Sequence
<220> FEATURE:
<223> OTHER INFORMATION: Synthetic Sequence

<400> SEQUENCE: 1

Met Ser Asp Ser Glu Val Asn Gln Glu Ala Lys Pro Glu Val Lys Pro
 1               5                  10                  15

Glu Val Lys Pro Glu Thr His Ile Asn Leu Lys Val Ser Asp Gly Ser
            20                  25                  30

Ser Glu Ile Phe Phe Lys Ile Lys Lys Thr Thr Pro Leu Arg Arg Leu
        35                  40                  45

Met Glu Ala Phe Ala Lys Arg Gln Gly Lys Glu Met Asp Ser Leu Thr
    50                  55                  60

Phe Leu Tyr Asp Gly Ile Glu Ile Gln Ala Asp Gln Thr Pro Glu Asp
65                  70                  75                  80

Leu Asp Met Glu Asp Asn Asp Ile Ile Glu Ala His Arg Glu Gln Ile
                85                  90                  95
```

Gly Gly

```
<210> SEQ ID NO 2
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: VARIANT
<222> LOCATION: 1, 8
<223> OTHER INFORMATION: Xaa = any amino acid other than arginine
<220> FEATURE:
<221> NAME/KEY: VARIANT
<222> LOCATION: 3-5, 7
<223> OTHER INFORMATION: Xaa = any amino acid

<400> SEQUENCE: 2

Xaa Phe Xaa Xaa Xaa Gly Xaa Xaa
 1               5

<210> SEQ ID NO 3
<211> LENGTH: 621
<212> TYPE: PRT
<213> ORGANISM: Artificial Sequence
<220> FEATURE:
<223> OTHER INFORMATION: Synthetic Sequence

<400> SEQUENCE: 3

Met Ser Val Glu Val Asp Lys His Arg Asn Thr Leu Gln Tyr His Lys
 1               5                  10                  15

Lys Asn Pro Tyr Ser Pro Leu Phe Ser Pro Ile Ser Thr Tyr Arg Cys
             20                  25                  30

Tyr Pro Arg Val Leu Asn Asn Pro Ser Glu Ser Arg Arg Ser Ala Ser
         35                  40                  45

Phe Ser Gly Ile Tyr Lys Lys Arg Thr Asn Thr Ser Arg Phe Asn Tyr
     50                  55                  60

Leu Asn Asp Arg Arg Val Leu Ser Met Glu Glu Ser Met Lys Asp Gly
 65                  70                  75                  80

Ser Asp Arg Ala Ser Lys Ala Gly Phe Ile Gly Gly Ile Arg Glu Thr
                 85                  90                  95

Leu Trp Asn Ser Gly Lys Tyr Leu Trp His Thr Phe Val Lys Asn Glu
            100                 105                 110

Pro Arg Asn Phe Asp Gly Ser Glu Val Glu Ala Ser Gly Asn Ser Asp
        115                 120                 125

Val Glu Ser Arg Ser Ser Gly Ser Arg Ser Ser Asp Val Pro Tyr Gly
    130                 135                 140

Leu Arg Glu Asn Tyr Ser Ser Asp Thr Arg Lys His Lys Phe Asp Thr
145                 150                 155                 160

Ser Thr Trp Ala Leu Pro Asn Lys Arg Arg Ile Glu Ser Glu Gly
                165                 170                 175

Val Gly Thr Pro Ser Thr Ser Pro Ile Ser Ser Leu Ala Ser Gln Lys
            180                 185                 190

Ser Asn Cys Asp Ser Asp Asn Ser Ile Thr Phe Ser Arg Asp Pro Phe
        195                 200                 205

Gly Trp Asn Lys Trp Lys Thr Ser Ala Ile Gly Ser Asn Ser Glu Asn
    210                 215                 220

Asn Thr Ser Asp Gln Lys Asn Ser Tyr Asp Arg Arg Gln Tyr Gly Thr
225                 230                 235                 240

Ala Phe Ile Arg Lys Lys Lys Val Ala Lys Gln Asn Ile Asn Asn Thr
```

```
                      245                 250                 255
Lys Leu Val Ser Arg Ala Gln Ser Glu Glu Val Thr Tyr Leu Arg Gln
            260                 265                 270

Ile Phe Asn Gly Glu Tyr Lys Val Pro Lys Ile Leu Lys Glu Glu Arg
        275                 280                 285

Glu Arg Gln Leu Lys Leu Met Asp Met Asp Lys Glu Lys Asp Thr Gly
    290                 295                 300

Leu Lys Lys Ser Ile Ile Asp Leu Thr Glu Lys Ile Lys Thr Ile Leu
305                 310                 315                 320

Ile Glu Asn Asn Lys Asn Arg Leu Gln Thr Arg Asn Glu Asn Asp Asp
                325                 330                 335

Asp Leu Val Phe Val Lys Glu Lys Ile Ser Ser Leu Glu Arg Lys
            340                 345                 350

His Lys Asp Tyr Leu Asn Gln Lys Leu Lys Phe Asp Arg Ser Ile Leu
        355                 360                 365

Glu Phe Glu Lys Asp Phe Lys Arg Tyr Asn Glu Ile Leu Asn Glu Arg
    370                 375                 380

Lys Lys Ile Gln Glu Asp Leu Lys Lys Lys Glu Gln Leu Ala Lys
385                 390                 395                 400

Lys Lys Leu Val Pro Glu Leu Asn Glu Lys Asp Asp Gln Val Gln
                405                 410                 415

Lys Ala Leu Ala Ser Arg Glu Asn Thr Gln Leu Met Asn Arg Asp Asn
            420                 425                 430

Ile Glu Ile Thr Val Arg Asp Phe Lys Thr Leu Ala Pro Arg Arg Trp
        435                 440                 445

Leu Asn Ser Gly Ile Ile Ser Phe Phe Met Lys Tyr Ile Glu Lys Ser
    450                 455                 460

Thr Pro Asn Thr Val Ala Phe Asn Ser Phe Phe Tyr Thr Asn Leu Ser
465                 470                 475                 480

Glu Arg Gly Tyr Gln Gly Val Arg Arg Trp Met Lys Arg Lys Lys Thr
                485                 490                 495

Gln Ile Asp Lys Leu Asp Lys Ile Phe Thr Pro Ile Asn Leu Asn Gln
            500                 505                 510

Ser His Trp Ala Leu Gly Ile Ile Asp Leu Lys Lys Lys Thr Ile Gly
        515                 520                 525

Tyr Val Asp Ser Leu Ser Asn Gly Pro Asn Ala Met Ser Phe Ala Ile
    530                 535                 540

Leu Thr Asp Leu Gln Lys Tyr Val Met Glu Glu Ser Lys His Thr Ile
545                 550                 555                 560

Gly Glu Asp Phe Asp Leu Ile His Leu Asp Cys Pro Gln Gln Pro Asn
                565                 570                 575

Gly Tyr Asp Cys Gly Ile Tyr Val Cys Met Asn Thr Leu Tyr Gly Ser
            580                 585                 590

Ala Asp Ala Pro Leu Asp Phe Asp Tyr Lys Asp Ala Ile Arg Met Arg
        595                 600                 605

Arg Phe Ile Ala His Leu Ile Leu Thr Asp Ala Leu Lys
    610                 615                 620

<210> SEQ ID NO 4
<211> LENGTH: 221
<212> TYPE: PRT
<213> ORGANISM: Artificial Sequence
<220> FEATURE:
<223> OTHER INFORMATION: Synthetic Sequence

<400> SEQUENCE: 4
```

```
Met Gly Leu Val Pro Glu Leu Asn Glu Lys Asp Asp Gln Val Gln
 1               5                  10                  15

Lys Ala Leu Ala Ser Arg Glu Asn Thr Gln Leu Met Asn Arg Asp Asn
                20                  25                  30

Ile Glu Ile Thr Val Arg Asp Phe Lys Thr Leu Ala Pro Arg Arg Trp
            35                  40                  45

Leu Asn Ser Gly Ile Ile Ser Phe Phe Met Lys Tyr Ile Glu Lys Ser
     50                  55                  60

Thr Pro Asn Thr Val Ala Phe Asn Ser Phe Tyr Thr Asn Leu Ser
 65                  70                  75                  80

Glu Arg Gly Tyr Gln Gly Val Arg Arg Trp Met Lys Arg Lys Lys Thr
                85                  90                  95

Gln Ile Asp Lys Leu Asp Lys Ile Phe Thr Pro Ile Asn Leu Asn Gln
            100                 105                 110

Ser His Trp Ala Leu Gly Ile Ile Asp Leu Lys Lys Lys Thr Ile Gly
        115                 120                 125

Tyr Val Asp Ser Leu Ser Asn Gly Pro Asn Ala Met Ser Phe Ala Ile
    130                 135                 140

Leu Thr Asp Leu Gln Lys Tyr Val Met Glu Glu Ser Lys His Thr Ile
145                 150                 155                 160

Gly Glu Asp Phe Asp Leu Ile His Leu Asp Cys Pro Gln Gln Pro Asn
                165                 170                 175

Gly Tyr Asp Cys Gly Ile Tyr Val Cys Met Asn Thr Leu Tyr Gly Ser
            180                 185                 190

Ala Asp Ala Pro Leu Asp Phe Asp Tyr Lys Asp Ala Ile Arg Met Arg
        195                 200                 205

Arg Phe Ile Ala His Leu Ile Leu Thr Asp Ala Leu Lys
    210                 215                 220

<210> SEQ ID NO 5
<211> LENGTH: 229
<212> TYPE: PRT
<213> ORGANISM: Artificial Sequence
<220> FEATURE:
<223> OTHER INFORMATION: Synthetic Sequence

<400> SEQUENCE: 5

Met Gly Leu Val Pro Glu Leu Asn Glu Lys Asp Asp Gln Val Gln
 1               5                  10                  15

Lys Ala Leu Ala Ser Arg Glu Asn Thr Gln Leu Met Asn Arg Asp Asn
                20                  25                  30

Ile Glu Ile Thr Val Arg Asp Phe Lys Thr Leu Ala Pro Arg Arg Trp
            35                  40                  45

Leu Asn Ser Gly Ile Ile Ser Phe Phe Met Lys Tyr Ile Glu Lys Ser
     50                  55                  60

Thr Pro Asn Thr Val Ala Phe Asn Ser Phe Tyr Thr Asn Leu Ser
 65                  70                  75                  80

Glu Arg Gly Tyr Gln Gly Val Arg Arg Trp Met Lys Arg Lys Lys Thr
                85                  90                  95

Gln Ile Asp Lys Leu Asp Lys Ile Phe Thr Pro Ile Asn Leu Asn Gln
            100                 105                 110

Ser His Trp Ala Leu Gly Ile Ile Asp Leu Lys Lys Lys Thr Ile Gly
        115                 120                 125

Tyr Val Asp Ser Leu Ser Asn Gly Pro Asn Ala Met Ser Phe Ala Ile
    130                 135                 140
```

Leu Thr Asp Leu Gln Lys Tyr Val Met Glu Glu Ser Lys His Thr Ile
145                 150                 155                 160

Gly Glu Asp Phe Asp Leu Ile His Leu Asp Cys Pro Gln Gln Pro Asn
                165                 170                 175

Gly Tyr Asp Cys Gly Ile Tyr Val Cys Met Asn Thr Leu Tyr Gly Ser
            180                 185                 190

Ala Asp Ala Pro Leu Asp Phe Asp Tyr Lys Asp Ala Ile Arg Met Arg
        195                 200                 205

Arg Phe Ile Ala His Leu Ile Leu Thr Asp Ala Leu Lys Leu Glu His
    210                 215                 220

His His His His His
225

<210> SEQ ID NO 6
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: VARIANT
<222> LOCATION: 4, 8
<223> OTHER INFORMATION: Xaa = non-acidic amino acid
<220> FEATURE:
<221> NAME/KEY: VARIANT
<222> LOCATION: 5-7
<223> OTHER INFORMATION: Xaa = any amino acid

<400> SEQUENCE: 6

Trp Leu Asn Xaa Xaa Xaa Xaa Xaa
 1               5

<210> SEQ ID NO 7
<211> LENGTH: 33
<212> TYPE: DNA
<213> ORGANISM: Artificial Sequence
<220> FEATURE:
<223> OTHER INFORMATION: Primer

<400> SEQUENCE: 7
ggcgctcgag tcccgcgaaa ttaatacgac tca                               33

<210> SEQ ID NO 8
<211> LENGTH: 42
<212> TYPE: DNA
<213> ORGANISM: Artificial Sequence
<220> FEATURE:
<223> OTHER INFORMATION: Primer

<400> SEQUENCE: 8
cgcaaagctt gagctcttac ttgtacagct cgtccatgcc ga                     42

<210> SEQ ID NO 9
<211> LENGTH: 32
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (19)...(21)
<223> OTHER INFORMATION: n = a, c, t, or g

<400> SEQUENCE: 9
aataccgtcg tacaagaann ntaaggagtc ca                                32

<210> SEQ ID NO 10
<211> LENGTH: 36
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (18)...(20)
<223> OTHER INFORMATION: n = a, c, t, or g

<400> SEQUENCE: 10
tcttgtacga cggtattnnn attcaagctg atcaga         36

<210> SEQ ID NO 11
<211> LENGTH: 49
<212> TYPE: DNA
<213> ORGANISM: Artificial Sequence
<220> FEATURE:
<223> OTHER INFORMATION: Primer

<400> SEQUENCE: 11
cgcgacatat gagggtgctt gtactagctc ttgctgtggc tctcgcagt         49

<210> SEQ ID NO 12
<211> LENGTH: 38
<212> TYPE: DNA
<213> ORGANISM: Artificial Sequence
<220> FEATURE:
<223> OTHER INFORMATION: Primer

<400> SEQUENCE: 12
cgcgaggtct caacctccaa tctgttcgcg gtgagcct         38

<210> SEQ ID NO 13
<211> LENGTH: 55
<212> TYPE: DNA
<213> ORGANISM: Artificial Sequence
<220> FEATURE:
<223> OTHER INFORMATION: Primer

<400> SEQUENCE: 13
cgcgcaggtc tctaggtagg gtgcttgtac tagctcttgc tgtggctctc gcagt         55

<210> SEQ ID NO 14
<211> LENGTH: 58
<212> TYPE: DNA
<213> ORGANISM: Artificial Sequence
<220> FEATURE:
<223> OTHER INFORMATION: Primer

<400> SEQUENCE: 14
cgcgcaggtc tctaggtcct agggtgcttg tactagctct tgctgtggct ctcgcagt         58

<210> SEQ ID NO 15
<211> LENGTH: 44
<212> TYPE: DNA
<213> ORGANISM: Artificial Sequence
<220> FEATURE:
<223> OTHER INFORMATION: Primer

<400> SEQUENCE: 15
tgtacagagc tcacgcgtgc atgctcggac tcagaagtca atca         44

<210> SEQ ID NO 16
<211> LENGTH: 36
<212> TYPE: DNA
<213> ORGANISM: Artificial Sequence
<220> FEATURE:
<223> OTHER INFORMATION: Primer

<400> SEQUENCE: 16
cgcgagtcga cttaccaatg cttaatcagt gaggca                                36

<210> SEQ ID NO 17
<211> LENGTH: 33
<212> TYPE: DNA
<213> ORGANISM: Artificial Sequence
<220> FEATURE:
<223> OTHER INFORMATION: Primer

<400> SEQUENCE: 17
ggcgaagctt tcccgcgaaa ttaatacgac tca                                   33

<210> SEQ ID NO 18
<211> LENGTH: 32
<212> TYPE: DNA
<213> ORGANISM: Artificial Sequence
<220> FEATURE:
<223> OTHER INFORMATION: Primer

<400> SEQUENCE: 18
cgcagcatgc ggggtcttca tctcctggac ca                                    32

<210> SEQ ID NO 19
<211> LENGTH: 40
<212> TYPE: DNA
<213> ORGANISM: Artificial Sequence
<220> FEATURE:
<223> OTHER INFORMATION: Primer

<400> SEQUENCE: 19
ggaattaacc atgggtcatc accatcatca tcacggaggt                            40

<210> SEQ ID NO 20
<211> LENGTH: 27
<212> TYPE: DNA
<213> ORGANISM: Artificial Sequence
<220> FEATURE:
<223> OTHER INFORMATION: Primer

<400> SEQUENCE: 20
ttagccatct tcgtggtgcc aaggtct                                          27

<210> SEQ ID NO 21
<211> LENGTH: 55
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 31-36, 43-45
<223> OTHER INFORMATION: n = a, c, t, g

<400> SEQUENCE: 21
aagaccttgg caccacgaag atggctaaat nnnnnnatca ttnnnttttt tatga           55

<210> SEQ ID NO 22
<211> LENGTH: 32
<212> TYPE: DNA
<213> ORGANISM: Artificial Sequence
<220> FEATURE:
<223> OTHER INFORMATION: Primer

<400> SEQUENCE: 22

```
gtggtgctcg agtcatttta aagcgtcggt ta                              32
```

```
<210> SEQ ID NO 23
<211> LENGTH: 55
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (31)...(45)
<223> OTHER INFORMATION: n = a, c, t, g

<400> SEQUENCE: 23
aagaccttgg caccacgaag atggctaaat nnnnnnnnnn nnnnnttttt tatga      55
```

```
<210> SEQ ID NO 24
<211> LENGTH: 5
<212> TYPE: PRT
<213> ORGANISM: Artificial Sequence
<220> FEATURE:
<223> OTHER INFORMATION: Synthetic sequence

<400> SEQUENCE: 24

Asp Thr Ile Ile Glu
1               5
```

```
<210> SEQ ID NO 25
<211> LENGTH: 5
<212> TYPE: PRT
<213> ORGANISM: Artificial Sequence
<220> FEATURE:
<223> OTHER INFORMATION: Synthetic sequence

<400> SEQUENCE: 25

Ser Gly Ile Ile Ser
1               5
```

```
<210> SEQ ID NO 26
<211> LENGTH: 5
<212> TYPE: PRT
<213> ORGANISM: Artificial Sequence
<220> FEATURE:
<223> OTHER INFORMATION: Synthetic sequence

<400> SEQUENCE: 26

Ala Met Ile Ile Ala
1               5
```

```
<210> SEQ ID NO 27
<211> LENGTH: 5
<212> TYPE: PRT
<213> ORGANISM: Artificial Sequence
<220> FEATURE:
<223> OTHER INFORMATION: Synthetic sequence

<400> SEQUENCE: 27

Ser Thr Ile Ile Ala
1               5
```

```
<210> SEQ ID NO 28
<211> LENGTH: 5
<212> TYPE: PRT
<213> ORGANISM: Artificial Sequence
<220> FEATURE:
<223> OTHER INFORMATION: Synthetic sequence

<400> SEQUENCE: 28
```

Ser Thr Ile Ile Met
1               5

<210> SEQ ID NO 29
<211> LENGTH: 45
<212> TYPE: DNA
<213> ORGANISM: Artificial Sequence
<220> FEATURE:
<223> OTHER INFORMATION: Primer

<400> SEQUENCE: 29
cgcgacctgc atcgaggtat gggcaagggg tttgggctcc tgagg        45

<210> SEQ ID NO 30
<211> LENGTH: 47
<212> TYPE: DNA
<213> ORGANISM: Artificial Sequence
<220> FEATURE:
<223> OTHER INFORMATION: Primer

<400> SEQUENCE: 30
cgcgacctgc atgtctagat taggatccag tcttcgtgta aaccaag        47

<210> SEQ ID NO 31
<211> LENGTH: 38
<212> TYPE: DNA
<213> ORGANISM: Artificial Sequence
<220> FEATURE:
<223> OTHER INFORMATION: Primer

<400> SEQUENCE: 31
atcacgtctc gaggtggact cctggagctg gcagggac        38

<210> SEQ ID NO 32
<211> LENGTH: 35
<212> TYPE: DNA
<213> ORGANISM: Artificial Sequence
<220> FEATURE:
<223> OTHER INFORMATION: Primer

<400> SEQUENCE: 32
gcatcgtctc actagtcaat tgcacttggg agagt        35

<210> SEQ ID NO 33
<211> LENGTH: 38
<212> TYPE: DNA
<213> ORGANISM: Artificial Sequence
<220> FEATURE:
<223> OTHER INFORMATION: Primer

<400> SEQUENCE: 33
atgatgggtc tcaaggtatg tcccaggccc cgggagca        38

<210> SEQ ID NO 34
<211> LENGTH: 36
<212> TYPE: DNA
<213> ORGANISM: Artificial Sequence
<220> FEATURE:
<223> OTHER INFORMATION: Primer

<400> SEQUENCE: 34
atgatgggtc tctctagatc agtctgtccg cagcca        36

<210> SEQ ID NO 35
<211> LENGTH: 53
<212> TYPE: DNA

```
<213> ORGANISM: Artificial Sequence
<220> FEATURE:
<223> OTHER INFORMATION: Primer

<400> SEQUENCE: 35
gcgcaagctt gctatggaga cagacacact cctgctatgg gtactgctgc tct        53

<210> SEQ ID NO 36
<211> LENGTH: 55
<212> TYPE: DNA
<213> ORGANISM: Artificial Sequence
<220> FEATURE:
<223> OTHER INFORMATION: Primer

<400> SEQUENCE: 36
gatgatggtg atgaccgtca ccagtggaac ctggaaccca gagcagcagt accca       55

<210> SEQ ID NO 37
<211> LENGTH: 45
<212> TYPE: DNA
<213> ORGANISM: Artificial Sequence
<220> FEATURE:
<223> OTHER INFORMATION: Primer

<400> SEQUENCE: 37
ccaggttcca ctggtgacgg tcatcaccat catcatcacg gaggt                  45

<210> SEQ ID NO 38
<211> LENGTH: 53
<212> TYPE: DNA
<213> ORGANISM: Artificial Sequence
<220> FEATURE:
<223> OTHER INFORMATION: Primer

<400> SEQUENCE: 38
cgcgtctaga gagacggcat gccgtctcaa cctccgtgat gatgatggtg atg         53

<210> SEQ ID NO 39
<211> LENGTH: 38
<212> TYPE: DNA
<213> ORGANISM: Artificial Sequence
<220> FEATURE:
<223> OTHER INFORMATION: Primer

<400> SEQUENCE: 39
cgcaggtctc taggtgaaag acagggtaag gaaatgga                          38

<210> SEQ ID NO 40
<211> LENGTH: 51
<212> TYPE: DNA
<213> ORGANISM: Artificial Sequence
<220> FEATURE:
<223> OTHER INFORMATION: Primer

<400> SEQUENCE: 40
cgcgtctaga gagacggcat gccgtctcaa cctccaatct gttcgcggtg a           51

<210> SEQ ID NO 41
<211> LENGTH: 38
<212> TYPE: DNA
<213> ORGANISM: Artificial Sequence
<220> FEATURE:
<223> OTHER INFORMATION: Primer

<400> SEQUENCE: 41
cgcaggtctc taggttcgga ctcagaagtc aatcaaga                          38
```

<210> SEQ ID NO 42
<211> LENGTH: 35
<212> TYPE: DNA
<213> ORGANISM: Artificial Sequence
<220> FEATURE:
<223> OTHER INFORMATION: Primer

<400> SEQUENCE: 42
cgcaggtctc taggttccga ggagaagccc aagga                         35

<210> SEQ ID NO 43
<211> LENGTH: 50
<212> TYPE: DNA
<213> ORGANISM: Artificial Sequence
<220> FEATURE:
<223> OTHER INFORMATION: Primer

<400> SEQUENCE: 43
cgcgtctaga gagacggcat gccgtctcaa cctcccgtct gctgctggaa          50

<210> SEQ ID NO 44
<211> LENGTH: 38
<212> TYPE: DNA
<213> ORGANISM: Artificial Sequence
<220> FEATURE:
<223> OTHER INFORMATION: Primer

<400> SEQUENCE: 44
atcacgtctc gaggtggact cctggagctg gcagggac                      38

<210> SEQ ID NO 45
<211> LENGTH: 36
<212> TYPE: DNA
<213> ORGANISM: Artificial Sequence
<220> FEATURE:
<223> OTHER INFORMATION: Primer

<400> SEQUENCE: 45
gcatcgtctc actagatcaa ttgcacttgg gagagt                        36

<210> SEQ ID NO 46
<211> LENGTH: 35
<212> TYPE: DNA
<213> ORGANISM: Artificial Sequence
<220> FEATURE:
<223> OTHER INFORMATION: Primer

<400> SEQUENCE: 46
atcacgtctc gaggtctcct ggagctggca gggac                         35

<210> SEQ ID NO 47
<211> LENGTH: 36
<212> TYPE: DNA
<213> ORGANISM: Artificial Sequence
<220> FEATURE:
<223> OTHER INFORMATION: Primer

<400> SEQUENCE: 47
cgcaggtctc taggttctga ccaggaggca aaacct                        36

<210> SEQ ID NO 48
<211> LENGTH: 51
<212> TYPE: DNA
<213> ORGANISM: Artificial Sequence
<220> FEATURE:
<223> OTHER INFORMATION: Primer -continued

<400> SEQUENCE: 48
cgcgtctaga gagacggcat gccgtctcaa cctcccgttt gttcctgata a        51

<210> SEQ ID NO 49
<211> LENGTH: 56
<212> TYPE: DNA
<213> ORGANISM: Artificial Sequence
<220> FEATURE:
<223> OTHER INFORMATION: Primer

<400> SEQUENCE: 49
atgattatca gcaatttcct gaccctcaaa gagaaacgtg agtgaattca ttggaa    56

<210> SEQ ID NO 50
<211> LENGTH: 56
<212> TYPE: DNA
<213> ORGANISM: Artificial Sequence
<220> FEATURE:
<223> OTHER INFORMATION: Primer

<400> SEQUENCE: 50
ccaatgaatt cactcacgtt tctctttgag ggtcaggaaa ttgctgataa tcatac    56

<210> SEQ ID NO 51
<211> LENGTH: 41
<212> TYPE: DNA
<213> ORGANISM: Artificial Sequence
<220> FEATURE:
<223> OTHER INFORMATION: Primer

<400> SEQUENCE: 51
tggctgcccg tcgaactcga atgtgatctg cctcattgac a              41

<210> SEQ ID NO 52
<211> LENGTH: 41
<212> TYPE: DNA
<213> ORGANISM: Artificial Sequence
<220> FEATURE:
<223> OTHER INFORMATION: Primer

<400> SEQUENCE: 52
tcaatgaggc agatcacatt cgagttcgac gggcagccaa t              41

<210> SEQ ID NO 53
<211> LENGTH: 37
<212> TYPE: DNA
<213> ORGANISM: Artificial Sequence
<220> FEATURE:
<223> OTHER INFORMATION: Primer

<400> SEQUENCE: 53
gcgccgtctc taggtagttt ctggcagttc cagagga                   37

<210> SEQ ID NO 54
<211> LENGTH: 39
<212> TYPE: DNA
<213> ORGANISM: Artificial Sequence
<220> FEATURE:
<223> OTHER INFORMATION: Primer

<400> SEQUENCE: 54
gcgccgtctc tctagattag cactggagtt tgtccctgc                 39

<210> SEQ ID NO 55
<211> LENGTH: 37
<212> TYPE: DNA

```
<213> ORGANISM: Artificial Sequence
<220> FEATURE:
<223> OTHER INFORMATION: Primer

<400> SEQUENCE: 55
gcgcggtctc taggtaacct ggtccagttt ggagtga                              37

<210> SEQ ID NO 56
<211> LENGTH: 35
<212> TYPE: DNA
<213> ORGANISM: Artificial Sequence
<220> FEATURE:
<223> OTHER INFORMATION: Primer

<400> SEQUENCE: 56
gcgcggtctc tctagattag cagggtgggg tgggc                                35

<210> SEQ ID NO 57
<211> LENGTH: 39
<212> TYPE: DNA
<213> ORGANISM: Artificial Sequence
<220> FEATURE:
<223> OTHER INFORMATION: Primer

<400> SEQUENCE: 57
gcgcgaagac ataggtcgtc actgggacag tacctcctg                            39

<210> SEQ ID NO 58
<211> LENGTH: 44
<212> TYPE: DNA
<213> ORGANISM: Artificial Sequence
<220> FEATURE:
<223> OTHER INFORMATION: Primer

<400> SEQUENCE: 58
gcgcgaagac atctagatta tgagctccag aatttcttct gtcc                      44

<210> SEQ ID NO 59
<211> LENGTH: 39
<212> TYPE: DNA
<213> ORGANISM: Artificial Sequence
<220> FEATURE:
<223> OTHER INFORMATION: Primer

<400> SEQUENCE: 59
gcgccgtctc taggtggctt gctagaactc aagtccatg                            39

<210> SEQ ID NO 60
<211> LENGTH: 41
<212> TYPE: DNA
<213> ORGANISM: Artificial Sequence
<220> FEATURE:
<223> OTHER INFORMATION: Primer

<400> SEQUENCE: 60
gcgccgtctc tctagattag cagaggaagt tggggtaata c                         41

<210> SEQ ID NO 61
<211> LENGTH: 36
<212> TYPE: DNA
<213> ORGANISM: Artificial Sequence
<220> FEATURE:
<223> OTHER INFORMATION: Primer

<400> SEQUENCE: 61
gcgccgtctc taggtggctg gaccattcct ggcacg                               36
```

```
<210> SEQ ID NO 62
<211> LENGTH: 44
<212> TYPE: DNA
<213> ORGANISM: Artificial Sequence
<220> FEATURE:
<223> OTHER INFORMATION: Primer

<400> SEQUENCE: 62
gcgccgtctc tctagattaa tatgaggtgg cctcagcctt ccag          44

<210> SEQ ID NO 63
<211> LENGTH: 5
<212> TYPE: PRT
<213> ORGANISM: Artificial Sequence
<220> FEATURE:
<223> OTHER INFORMATION: Synthetic sequence

<400> SEQUENCE: 63

Cys Gln Gln Cys His
1               5

<210> SEQ ID NO 64
<211> LENGTH: 18
<212> TYPE: PRT
<213> ORGANISM: Artificial Sequence
<220> FEATURE:
<223> OTHER INFORMATION: Synthetic sequence

<400> SEQUENCE: 64

Gly Ser Ala Lys Lys Gly Ala Thr Leu Phe Lys Thr Arg Cys Gln Gln
1               5                   10                  15

Cys His

<210> SEQ ID NO 65
<211> LENGTH: 4
<212> TYPE: PRT
<213> ORGANISM: Artificial Sequence
<220> FEATURE:
<223> OTHER INFORMATION: Synthetic sequence
<220> FEATURE:
<221> NAME/KEY: VARIANT
<222> LOCATION: 1, 3
<223> OTHER INFORMATION: Xaa = any amino acid other than arginine

<400> SEQUENCE: 65

Xaa Phe Xaa Phe
1

<210> SEQ ID NO 66
<211> LENGTH: 8
<212> TYPE: PRT
<213> ORGANISM: Artificial Sequence
<220> FEATURE:
<223> OTHER INFORMATION: Synthetic sequence

<400> SEQUENCE: 66

Arg Phe Leu Tyr Asp Gly Ile Arg
1               5

<210> SEQ ID NO 67
<211> LENGTH: 101
<212> TYPE: PRT
<213> ORGANISM: Sacharomyces cerevisiae

<400> SEQUENCE: 67

Met Ser Asp Ser Glu Val Asn Gln Glu Ala Lys Pro Glu Val Lys Pro
1               5                   10                  15
```

Glu Val Lys Pro Glu Thr His Ile Asn Leu Lys Val Ser Asp Gly Ser
            20                  25                  30

Ser Glu Ile Phe Phe Lys Ile Lys Thr Thr Pro Leu Arg Arg Leu
        35                  40                  45

Met Glu Ala Phe Ala Lys Arg Gln Gly Lys Glu Met Asp Ser Leu Arg
50                  55                  60

Phe Leu Tyr Asp Gly Ile Arg Ile Gln Ala Asp Gln Thr Pro Glu Asp
65                  70                  75                  80

Leu Asp Met Glu Asp Asn Asp Ile Ile Glu Ala His Arg Glu Gln Ile
                85                  90                  95

Gly Gly Ala Thr Tyr
            100

<210> SEQ ID NO 68
<211> LENGTH: 95
<212> TYPE: PRT
<213> ORGANISM: Xenopus laevis

<400> SEQUENCE: 68

Met Ala Asp Asp Lys Pro Lys Glu Gly Val Lys Thr Glu Asn Asn Asp
1               5                   10                  15

His Ile Asn Leu Lys Val Ala Gly Gln Asp Gly Ser Val Val Gln Phe
            20                  25                  30

Lys Ile Lys Arg Gln Thr Pro Leu Ser Lys Leu Met Lys Ala Tyr Cys
        35                  40                  45

Glu Arg Gln Gly Leu Ser Met Arg Gln Ile Arg Phe Arg Phe Asp Gly
50                  55                  60

Gln Pro Ile Asn Glu Thr Asp Thr Pro Ala Gln Leu Glu Met Glu Asp
65                  70                  75                  80

Glu Asp Thr Ile Asp Val Phe Gln Gln Gln Thr Gly Gly Ser Phe
                85                  90                  95

<210> SEQ ID NO 69
<211> LENGTH: 101
<212> TYPE: PRT
<213> ORGANISM: Homo Sapiens

<400> SEQUENCE: 69

Met Ser Asp Gln Glu Ala Lys Pro Ser Thr Glu Asp Leu Gly Asp Lys
1               5                   10                  15

Lys Glu Gly Glu Tyr Ile Lys Leu Lys Val Ile Gly Gln Asp Ser Ser
            20                  25                  30

Glu Ile His Phe Lys Val Lys Met Thr Thr His Leu Lys Lys Leu Lys
        35                  40                  45

Glu Ser Tyr Cys Gln Arg Gln Gly Val Pro Met Asn Ser Leu Arg Phe
50                  55                  60

Leu Phe Glu Gly Gln Arg Ile Ala Asp Asn His Thr Pro Lys Glu Leu
65                  70                  75                  80

Gly Met Glu Glu Glu Asp Val Ile Glu Val Tyr Gln Glu Gln Thr Gly
                85                  90                  95

Gly His Ser Thr Val
            100

<210> SEQ ID NO 70
<211> LENGTH: 95
<212> TYPE: PRT
<213> ORGANISM: Homo sapiens

```
<400> SEQUENCE: 70

Met Ala Asp Glu Lys Pro Lys Glu Gly Val Lys Thr Glu Asn Asn Asp
1               5                   10                  15

His Ile Asn Leu Lys Val Ala Gly Gln Asp Gly Ser Val Val Gln Phe
            20                  25                  30

Lys Ile Lys Arg His Thr Pro Leu Ser Lys Leu Met Lys Ala Tyr Cys
        35                  40                  45

Glu Arg Gln Gly Leu Ser Met Arg Gln Ile Arg Phe Arg Phe Asp Gly
    50                  55                  60

Gln Pro Ile Asn Glu Thr Asp Thr Pro Ala Gln Leu Glu Met Glu Asp
65                  70                  75                  80

Glu Asp Thr Ile Asp Val Phe Gln Gln Gln Thr Gly Gly Val Tyr
                85                  90                  95

<210> SEQ ID NO 71
<211> LENGTH: 103
<212> TYPE: PRT
<213> ORGANISM: Homo sapiens

<400> SEQUENCE: 71

Met Ser Glu Glu Lys Pro Lys Glu Gly Val Lys Thr Glu Asn Asp His
1               5                   10                  15

Ile Asn Leu Lys Val Ala Gly Gln Asp Gly Ser Val Val Gln Phe Lys
            20                  25                  30

Ile Lys Arg His Thr Pro Leu Ser Lys Leu Met Lys Ala Tyr Cys Glu
        35                  40                  45

Arg Gln Gly Leu Ser Met Arg Gln Ile Arg Phe Arg Phe Asp Gly Gln
    50                  55                  60

Pro Ile Asn Glu Thr Asp Thr Pro Ala Gln Leu Glu Met Glu Asp Glu
65                  70                  75                  80

Asp Thr Ile Asp Val Phe Gln Gln Gln Thr Gly Gly Val Pro Glu Ser
                85                  90                  95

Ser Leu Ala Gly His Ser Phe
            100

<210> SEQ ID NO 72
<211> LENGTH: 90
<212> TYPE: PRT
<213> ORGANISM: Drosophila Melanogaster

<400> SEQUENCE: 72

Met Ser Asp Glu Lys Lys Gly Gly Glu Thr Glu His Ile Asn Leu Lys
1               5                   10                  15

Val Leu Gly Gln Asp Asn Ala Val Val Gln Phe Lys Ile Lys Lys His
            20                  25                  30

Thr Pro Leu Arg Lys Leu Met Asn Ala Tyr Cys Asp Arg Ala Gly Leu
        35                  40                  45

Ser Met Gln Val Val Arg Phe Arg Phe Asp Gly Gln Pro Ile Asn Glu
    50                  55                  60

Asn Asp Thr Pro Thr Ser Leu Glu Met Glu Glu Gly Asp Thr Ile Glu
65                  70                  75                  80

Val Tyr Gln Gln Gln Thr Gly Gly Ala Pro
                85                  90

<210> SEQ ID NO 73
<211> LENGTH: 100
<212> TYPE: PRT
<213> ORGANISM: Arabidopsis Thaliana
```

```
<400> SEQUENCE: 73

Met Ser Ala Asn Gln Glu Glu Asp Lys Lys Pro Gly Asp Gly Gly Ala
1               5                   10                  15

His Ile Asn Leu Lys Val Lys Gly Gln Asp Gly Asn Glu Val Phe Phe
            20                  25                  30

Arg Ile Lys Arg Ser Thr Gln Leu Lys Lys Leu Met Asn Ala Tyr Cys
        35                  40                  45

Asp Arg Gln Ser Val Asp Met Asn Ser Ile Ala Phe Leu Phe Asp Gly
    50                  55                  60

Arg Arg Leu Arg Ala Glu Gln Thr Pro Asp Glu Leu Asp Met Glu Asp
65                  70                  75                  80

Gly Asp Glu Ile Asp Ala Met Leu His Gln Thr Gly Gly Ser Gly Gly
                85                  90                  95

Gly Ala Thr Ala
            100

<210> SEQ ID NO 74
<211> LENGTH: 103
<212> TYPE: PRT
<213> ORGANISM: Arabidopsis Thaliana

<400> SEQUENCE: 74

Met Ser Ala Thr Pro Glu Glu Asp Lys Lys Pro Asp Gln Gly Ala His
1               5                   10                  15

Ile Asn Leu Lys Val Lys Gly Gln Asp Gly Asn Glu Val Phe Phe Arg
            20                  25                  30

Ile Lys Arg Ser Thr Gln Leu Lys Lys Leu Met Asn Ala Tyr Cys Asp
        35                  40                  45

Arg Gln Ser Val Asp Phe Asn Ser Ile Ala Phe Leu Phe Asp Gly Arg
    50                  55                  60

Arg Leu Arg Ala Glu Gln Thr Pro Asp Glu Leu Glu Met Glu Asp Gly
65                  70                  75                  80

Asp Glu Ile Asp Ala Met Leu His Gln Thr Gly Gly Gly Ala Lys Asn
                85                  90                  95

Gly Leu Lys Leu Phe Cys Phe
            100

<210> SEQ ID NO 75
<211> LENGTH: 95
<212> TYPE: PRT
<213> ORGANISM: Homo sapiens

<400> SEQUENCE: 75

Met Ala Asn Glu Lys Pro Thr Glu Val Lys Thr Glu Asn Asn Asn
1               5                   10                  15

His Ile Asn Leu Lys Val Ala Gly Gln Asp Gly Ser Val Val Gln Phe
            20                  25                  30

Lys Ile Lys Arg Gln Thr Pro Leu Ser Lys Leu Met Lys Ala Tyr Cys
        35                  40                  45

Glu Pro Arg Gly Leu Ser Val Lys Gln Ile Arg Phe Arg Phe Gly Gly
    50                  55                  60

Gln Pro Ile Ser Gly Thr Asp Lys Pro Ala Gln Leu Glu Met Glu Asp
65                  70                  75                  80

Glu Asp Thr Ile Asp Val Phe Gln Gln Pro Thr Gly Gly Val Tyr
                85                  90                  95
```

<210> SEQ ID NO 76
<211> LENGTH: 621
<212> TYPE: PRT
<213> ORGANISM: Sacharomyces cerevisiae

<400> SEQUENCE: 76

Met Ser Val Glu Val Asp Lys His Arg Asn Thr Leu Gln Tyr His Lys
 1               5                  10                  15

Lys Asn Pro Tyr Ser Pro Leu Phe Ser Pro Ile Ser Thr Tyr Arg Cys
             20                  25                  30

Tyr Pro Arg Val Leu Asn Asn Pro Ser Glu Ser Arg Arg Ser Ala Ser
         35                  40                  45

Phe Ser Gly Ile Tyr Lys Lys Arg Thr Asn Thr Ser Arg Phe Asn Tyr
 50                  55                  60

Leu Asn Asp Arg Arg Val Leu Ser Met Glu Glu Ser Met Lys Asp Gly
65                  70                  75                  80

Ser Asp Arg Ala Ser Lys Ala Gly Phe Ile Gly Gly Ile Arg Glu Thr
                 85                  90                  95

Leu Trp Asn Ser Gly Lys Tyr Leu Trp His Thr Phe Val Lys Asn Glu
            100                 105                 110

Pro Arg Asn Phe Asp Gly Ser Glu Val Glu Ala Ser Gly Asn Ser Asp
        115                 120                 125

Val Glu Ser Arg Ser Ser Gly Ser Arg Ser Ser Asp Val Pro Tyr Gly
    130                 135                 140

Leu Arg Glu Asn Tyr Ser Ser Asp Thr Arg Lys His Lys Phe Asp Thr
145                 150                 155                 160

Ser Thr Trp Ala Leu Pro Asn Lys Arg Arg Ile Glu Ser Glu Gly
                165                 170                 175

Val Gly Thr Pro Ser Thr Ser Pro Ile Ser Ser Leu Ala Ser Gln Lys
            180                 185                 190

Ser Asn Cys Asp Ser Asp Asn Ser Ile Thr Phe Ser Arg Asp Pro Phe
        195                 200                 205

Gly Trp Asn Lys Trp Lys Thr Ser Ala Ile Gly Ser Asn Ser Glu Asn
    210                 215                 220

Asn Thr Ser Asp Gln Lys Asn Ser Tyr Asp Arg Arg Gln Tyr Gly Thr
225                 230                 235                 240

Ala Phe Ile Arg Lys Lys Val Ala Lys Gln Asn Ile Asn Asn Thr
                245                 250                 255

Lys Leu Val Ser Arg Ala Gln Ser Glu Glu Val Thr Tyr Leu Arg Gln
            260                 265                 270

Ile Phe Asn Gly Glu Tyr Lys Val Pro Lys Ile Leu Lys Glu Glu Arg
        275                 280                 285

Glu Arg Gln Leu Lys Leu Met Asp Met Asp Lys Glu Lys Asp Thr Gly
    290                 295                 300

Leu Lys Lys Ser Ile Ile Asp Leu Thr Glu Lys Ile Lys Thr Ile Leu
305                 310                 315                 320

Ile Glu Asn Asn Lys Asn Arg Leu Gln Thr Arg Asn Glu Asn Asp Asp
                325                 330                 335

Asp Leu Val Phe Val Lys Glu Lys Lys Ile Ser Ser Leu Glu Arg Lys
            340                 345                 350

His Lys Asp Tyr Leu Asn Gln Lys Leu Lys Phe Asp Arg Ser Ile Leu
        355                 360                 365

Glu Phe Glu Lys Asp Phe Lys Arg Tyr Asn Glu Ile Leu Asn Glu Arg
    370                 375                 380

Lys Lys Ile Gln Glu Asp Leu Lys Lys Lys Lys Glu Gln Leu Ala Lys

```
                385                 390                 395                 400
Lys Lys Leu Val Pro Glu Leu Asn Glu Lys Asp Asp Gln Val Gln
                    405                 410                 415
Lys Ala Leu Ala Ser Arg Glu Asn Thr Gln Leu Met Asn Arg Asp Asn
                420                 425                 430
Ile Glu Ile Thr Val Arg Asp Phe Lys Thr Leu Ala Pro Arg Arg Trp
            435                 440                 445
Leu Asn Asp Thr Ile Ile Glu Phe Phe Met Lys Tyr Ile Glu Lys Ser
            450                 455                 460
Thr Pro Asn Thr Val Ala Phe Asn Ser Phe Phe Tyr Thr Asn Leu Ser
465                 470                 475                 480
Glu Arg Gly Tyr Gln Gly Val Arg Arg Trp Met Lys Arg Lys Lys Thr
                485                 490                 495
Gln Ile Asp Lys Leu Asp Lys Ile Phe Thr Pro Ile Asn Leu Asn Gln
            500                 505                 510
Ser His Trp Ala Leu Gly Ile Ile Asp Leu Lys Lys Thr Ile Gly
            515                 520                 525
Tyr Val Asp Ser Leu Ser Asn Gly Pro Asn Ala Met Ser Phe Ala Ile
    530                 535                 540
Leu Thr Asp Leu Gln Lys Tyr Val Met Glu Glu Ser Lys His Thr Ile
545                 550                 555                 560
Gly Glu Asp Phe Asp Leu Ile His Leu Asp Cys Pro Gln Gln Pro Asn
                565                 570                 575
Gly Tyr Asp Cys Gly Ile Tyr Val Cys Met Asn Thr Leu Tyr Gly Ser
            580                 585                 590
Ala Asp Ala Pro Leu Asp Phe Asp Tyr Lys Asp Ala Ile Arg Met Arg
        595                 600                 605
Arg Phe Ile Ala His Leu Ile Leu Thr Asp Ala Leu Lys
        610                 615                 620

<210> SEQ ID NO 77
<211> LENGTH: 643
<212> TYPE: PRT
<213> ORGANISM: Homo Sapiens

<400> SEQUENCE: 77

Met Asp Asp Ile Ala Asp Arg Met Arg Met Asp Ala Gly Glu Val Thr
1               5                   10                  15
Leu Val Asn His Asn Ser Val Phe Lys Thr His Leu Leu Pro Gln Thr
                20                  25                  30
Gly Phe Pro Glu Asp Gln Leu Ser Leu Ser Asp Gln Gln Ile Leu Ser
            35                  40                  45
Ser Arg Gln Gly His Leu Asp Arg Ser Phe Thr Cys Ser Thr Arg Ser
        50                  55                  60
Ala Ala Tyr Asn Pro Ser Tyr Tyr Ser Asp Asn Pro Ser Ser Asp Ser
65                  70                  75                  80
Phe Leu Gly Ser Gly Asp Leu Arg Thr Phe Gly Gln Ser Ala Asn Gly
                85                  90                  95
Gln Trp Arg Asn Ser Thr Pro Ser Ser Ser Ser Leu Gln Lys Ser
            100                 105                 110
Arg Asn Ser Arg Ser Leu Tyr Leu Glu Thr Arg Lys Thr Ser Ser Gly
        115                 120                 125
Leu Ser Asn Ser Phe Ala Gly Lys Ser Asn His His Cys His Val Ser
    130                 135                 140
Ala Tyr Glu Lys Ser Phe Pro Ile Lys Pro Val Pro Ser Pro Ser Trp
```

-continued

```
            145                 150                 155                 160
Ser Gly Ser Cys Arg Arg Ser Leu Leu Ser Pro Lys Lys Thr Gln Arg
                    165                 170                 175

Arg His Val Ser Thr Ala Glu Glu Thr Val Gln Glu Glu Glu Arg Glu
                    180                 185                 190

Ile Tyr Arg Gln Leu Leu Gln Met Val Thr Gly Lys Gln Phe Thr Ile
                    195                 200                 205

Ala Lys Pro Thr Thr His Phe Pro Leu His Leu Ser Arg Cys Leu Ser
                    210                 215                 220

Ser Ser Lys Asn Thr Leu Lys Asp Ser Leu Phe Lys Asn Gly Asn Ser
225                 230                 235                 240

Cys Ala Ser Gln Ile Ile Gly Ser Asp Thr Ser Ser Gly Ser Ala
                    245                 250                 255

Ser Ile Leu Thr Asn Gln Glu Gln Leu Ser His Ser Val Tyr Ser Leu
                    260                 265                 270

Ser Ser Tyr Thr Pro Asp Val Ala Phe Gly Ser Lys Asp Ser Gly Thr
                    275                 280                 285

Leu His His Pro His His His Ser Val Pro His Gln Pro Asp Asn
        290                 295                 300

Leu Ala Ala Ser Asn Thr Gln Ser Glu Gly Ser Asp Ser Val Ile Leu
305                 310                 315                 320

Leu Lys Val Lys Asp Ser Gln Thr Pro Thr Pro Ser Ser Thr Phe Phe
                    325                 330                 335

Gln Ala Glu Leu Trp Ile Lys Glu Leu Thr Ser Val Tyr Asp Ser Arg
                    340                 345                 350

Ala Arg Glu Arg Leu Arg Gln Ile Glu Glu Gln Lys Ala Leu Ala Leu
                    355                 360                 365

Gln Leu Gln Asn Gln Arg Leu Gln Arg Glu His Ser Val His Asp
        370                 375                 380

Ser Val Glu Leu His Leu Arg Val Pro Leu Glu Lys Glu Ile Pro Val
385                 390                 395                 400

Thr Val Val Gln Glu Thr Gln Lys Lys Gly His Lys Leu Thr Asp Ser
                    405                 410                 415

Glu Asp Glu Phe Pro Glu Ile Thr Glu Glu Met Glu Lys Glu Ile Lys
                    420                 425                 430

Asn Val Phe Arg Asn Gly Asn Gln Asp Glu Val Leu Ser Glu Ala Phe
                    435                 440                 445

Arg Leu Thr Ile Thr Arg Lys Asp Ile Gln Thr Leu Asn His Leu Asn
450                 455                 460

Trp Leu Asn Asp Glu Ile Ile Asn Phe Tyr Met Asn Met Leu Met Glu
465                 470                 475                 480

Arg Ser Lys Glu Lys Gly Leu Pro Ser Val His Ala Phe Asn Thr Phe
                    485                 490                 495

Phe Phe Thr Lys Leu Lys Thr Ala Gly Tyr Gln Ala Val Lys Arg Trp
                    500                 505                 510

Thr Lys Lys Val Asp Val Phe Ser Val Asp Ile Leu Leu Val Pro Ile
                    515                 520                 525

His Leu Gly Val His Trp Cys Leu Ala Val Val Asp Phe Arg Lys Lys
                    530                 535                 540

Asn Ile Thr Tyr Tyr Asp Ser Met Gly Gly Ile Asn Asn Glu Ala Cys
545                 550                 555                 560

Arg Ile Leu Leu Gln Tyr Leu Lys Gln Glu Ser Ile Asp Lys Lys Arg
                    565                 570                 575
```

```
Lys Glu Phe Asp Thr Asn Gly Trp Gln Leu Phe Ser Lys Lys Ser Gln
            580                 585                 590

Ile Pro Gln Gln Met Asn Gly Ser Asp Cys Gly Met Phe Ala Cys Lys
        595                 600                 605

Tyr Ala Asp Cys Ile Thr Lys Asp Arg Pro Ile Asn Phe Thr Gln Gln
610                 615                 620

His Met Pro Tyr Phe Arg Lys Arg Met Val Trp Glu Ile Leu His Arg
625                 630                 635                 640

Lys Leu Leu

<210> SEQ ID NO 78
<211> LENGTH: 589
<212> TYPE: PRT
<213> ORGANISM: Homo sapiens

<400> SEQUENCE: 78

Met Tyr Arg Trp Leu Val Arg Ile Leu Gly Thr Ile Phe Arg Phe Cys
1               5                   10                  15

Asp Arg Ser Val Pro Pro Ala Arg Ala Leu Leu Lys Arg Arg Arg Ser
            20                  25                  30

Asp Ser Thr Leu Phe Ser Thr Val Asp Thr Asp Glu Ile Pro Ala Lys
        35                  40                  45

Arg Pro Arg Leu Asp Cys Phe Ile His Gln Val Lys Asn Ser Leu Tyr
    50                  55                  60

Asn Ala Ala Ser Leu Phe Gly Phe Pro Phe Gln Leu Thr Thr Lys Pro
65                  70                  75                  80

Met Val Thr Ser Ala Cys Asn Gly Thr Arg Asn Val Ala Pro Ser Gly
                85                  90                  95

Glu Val Phe Ser Asn Ser Ser Cys Glu Leu Thr Gly Ser Gly Ser
            100                 105                 110

Trp Asn Asn Met Leu Lys Leu Gly Asn Lys Ser Pro Asn Gly Ile Ser
        115                 120                 125

Asp Tyr Pro Lys Ile Arg Val Thr Val Thr Arg Asp Gln Pro Arg Arg
    130                 135                 140

Val Leu Pro Ser Phe Gly Phe Thr Leu Asn Ser Glu Gly Cys Asn Arg
145                 150                 155                 160

Arg Pro Gly Gly Arg Arg His Ser Lys Gly Asn Pro Glu Ser Ser Leu
                165                 170                 175

Met Trp Lys Pro Gln Glu Gln Ala Val Thr Glu Met Ile Ser Glu Glu
            180                 185                 190

Ser Gly Lys Gly Leu Arg Arg Pro His Cys Thr Val Glu Glu Gly Val
        195                 200                 205

Gln Lys Glu Glu Arg Glu Lys Tyr Arg Lys Leu Leu Glu Arg Leu Lys
    210                 215                 220

Glu Ser Gly His Gly Asn Ser Val Cys Pro Val Thr Ser Asn Tyr His
225                 230                 235                 240

Ser Ser Gln Arg Ser Gln Met Asp Thr Leu Lys Thr Lys Gly Trp Gly
                245                 250                 255

Glu Glu Gln Asn His Gly Val Lys Thr Thr Gln Phe Val Pro Lys Gln
            260                 265                 270

Tyr Arg Leu Val Glu Thr Arg Gly Pro Leu Cys Ser Leu Arg Ser Glu
        275                 280                 285

Lys Arg Cys Ser Lys Gly Lys Ile Thr Asp Thr Glu Thr Met Val Gly
    290                 295                 300

Ile Arg Phe Glu Asn Glu Ser Arg Arg Gly Tyr Gln Leu Glu Pro Asp
```

```
                305                 310                 315                 320
Leu Ser Glu Glu Val Ser Ala Arg Leu Arg Leu Gly Ser Gly Ser Asn
                    325                 330                 335
Gly Leu Leu Arg Arg Lys Val Ser Ile Ile Glu Thr Lys Glu Lys Asn
                340                 345                 350
Cys Ser Gly Lys Glu Arg Asp Arg Arg Thr Asp Asp Leu Leu Glu Leu
            355                 360                 365
Thr Glu Asp Met Glu Lys Glu Ile Ser Asn Ala Leu Gly His Gly Pro
        370                 375                 380
Gln Asp Glu Ile Leu Ser Ser Ala Phe Lys Leu Arg Ile Thr Arg Gly
385                 390                 395                 400
Asp Ile Gln Thr Leu Lys Asn Tyr His Trp Leu Asn Asp Val Ile
                405                 410                 415
Asn Phe Tyr Met Asn Leu Leu Val Glu Arg Asn Lys Lys Gln Gly Tyr
            420                 425                 430
Pro Ala Leu His Val Phe Ser Thr Phe Tyr Pro Lys Leu Lys Ser
        435                 440                 445
Gly Gly Tyr Gln Ala Val Lys Arg Trp Thr Lys Gly Val Asn Leu Phe
    450                 455                 460
Glu Gln Glu Ile Ile Leu Val Pro Ile His Arg Lys Val His Trp Ser
465                 470                 475                 480
Leu Val Val Ile Asp Leu Arg Lys Lys Cys Leu Lys Tyr Leu Asp Ser
                485                 490                 495
Met Gly Gln Lys Gly His Arg Ile Cys Glu Ile Leu Leu Gln Tyr Leu
            500                 505                 510
Gln Asp Glu Ser Lys Thr Lys Arg Asn Ser Asp Leu Asn Leu Leu Glu
        515                 520                 525
Trp Thr His His Ser Met Lys Pro His Glu Ile Pro Gln Gln Leu Asn
    530                 535                 540
Gly Ser Asp Cys Gly Met Phe Thr Cys Lys Tyr Ala Asp Tyr Ile Ser
545                 550                 555                 560
Arg Asp Lys Pro Ile Thr Phe Thr Gln His Gln Met Pro Leu Phe Arg
                565                 570                 575
Lys Lys Met Val Trp Glu Ile Leu His Gln Gln Leu Leu
            580                 585

<210> SEQ ID NO 79
<211> LENGTH: 1513
<212> TYPE: PRT
<213> ORGANISM: Drospohila Melanogaster

<400> SEQUENCE: 79

Met Ser Leu Pro Pro Glu Asp Thr Asp Leu Ser Thr Asn Ser Ala Tyr
1               5                   10                  15
Glu Ser Ala Leu Gln Ile Ala Ser Asn Val Ser Ala Ala Arg Val Val
                20                  25                  30
Gly Ser Ala Val Gly Gln Arg Phe Ser Pro Ser Ala Ala His Pro
            35                  40                  45
Asn Val Ile Glu Arg Val Ala Ser His Val Asp Ser Arg Arg Ser Thr
        50                  55                  60
Phe Pro Ser Trp Gly Asn Pro Ser Val Ala Pro Arg Gly Ser Glu Glu
65                  70                  75                  80
Ala Ala Ala Asn Ala Thr Ala Thr Gln Leu Leu Trp Ala Glu Asn Gln
                85                  90                  95
Gly Leu Pro Thr Ser His Leu Leu Pro Thr Glu Gln Ala Phe Glu Thr
```

```
                100             105             110
Leu Asn Thr Asn Ala Tyr Cys Ser Pro Pro Gly Asp Ser Arg Phe Thr
            115                 120                 125
Phe Pro Ser Gln Asn Tyr Ser Pro Leu Leu Pro Arg Cys Val Pro Val
            130                 135                 140
Pro Asn Gln Arg Tyr Ser Pro Asp Gly Ser Pro Ile His Gln Leu His
145                 150                 155                 160
Glu Leu Gln Asn Cys Pro Leu Ile Asp Ser Pro Ile Arg Leu Arg Phe
                165                 170                 175
Pro Ser Pro Leu Pro Glu Pro Pro Ser Leu Pro Thr Ile Thr Leu Thr
            180                 185                 190
Val Asp Ala Leu Ile Asp Leu Asp Gln Asn Asn Gln Val Ala Tyr Tyr
            195                 200                 205
Val Gln Gln Tyr Asn Asn Gln Pro Val Leu Tyr Gln Gln Asn Ile His
            210                 215                 220
Ile Gly Thr Gly Ile Gln Leu Cys Asp Gln Ala Ser Glu Asn Asn Gln
225                 230                 235                 240
Pro Ile Ile Leu His Ile Val Glu His Asn Pro Gln Thr Ile Thr Glu
                245                 250                 255
Ser Gln Glu Gln Phe His Gln Val Val Pro Glu Ile Gln Ile Asn Asn
                260                 265                 270
Ile Gln Glu Gln Asp Gln Lys Phe Glu Asn Gly Ile Ser Glu Gln Asn
                275                 280                 285
His Pro Ile Ala Thr Glu Ala Gln Asp Gln Thr Leu Thr Glu Ile Arg
            290                 295                 300
Asp Glu Asn Gln Ile Val Leu Ala Val Gln Glu Lys Asn Leu Thr Arg
305                 310                 315                 320
Ala Ser Glu Ile Gln Asp Gln Asn Gln Gln Thr Leu Thr Glu Ile Pro
                325                 330                 335
Glu Lys Cys Leu Gln Ile Ala Ser Pro Val Thr Thr Asp Ile Gln Val
                340                 345                 350
Gln Ser Pro Gln Val Val Ile Glu Ile Gln Glu Gln Asn His Gln Ser
            355                 360                 365
Val Thr Glu Ile Gln Glu Glu Val His Gln Thr Ala Pro Glu Ile Gln
            370                 375                 380
Val Asn Val Phe Gln Thr Ser Ser Asp Ile Gln Gly Gln Asn His Gln
385                 390                 395                 400
Ile Val Thr Glu Glu Asn His Gln Thr Ile Thr Glu Thr Gln Glu
                405                 410                 415
Asp Tyr Ser Ala Val Ser Glu Ile Gln Trp Glu Asn Leu Ser Phe Ser
            420                 425                 430
Ala Glu Ile Gln Glu Gln Asn Gln Gln Ile Val Thr Glu Val Thr Lys
            435                 440                 445
Leu Ala Ser Pro Ser Val Thr Asp Ile Gln Ala Gln Ser Pro Gln Ser
            450                 455                 460
Val Ile Glu Ile Gln Asp Asp Asp Asp Glu Asp Leu Lys Phe Glu Ser
465                 470                 475                 480
Asp Asp Leu His Thr Ile Pro Glu Ile Gln Glu Lys Asn Gln Gln Ser
                485                 490                 495
Pro Gln Phe Val Ile Glu Ile His Tyr Asp Asn Glu Asp Leu Lys Phe
            500                 505                 510
Ala Ser Asp Asn Gln Glu Gln Asp Gln Gln Thr Ala Glu Leu Gln Lys
            515                 520                 525
```

-continued

```
Glu Arg Phe Gln Phe Ala Ser Glu Ile Glu Lys Arg Asp Leu Gln Ile
            530                 535                 540

Val Thr Asp Thr His Lys Gln Asn Tyr His Asn Val Thr Asp Ile Pro
545                 550                 555                 560

Phe Ala Thr Tyr Ile Gln Glu Asn Glu Gln Leu Thr Pro Glu Asp
                565                 570                 575

Gln Glu Glu Asp Gln His Tyr Leu Asn Phe Glu Gly Asn Gln Gln Phe
            580                 585                 590

Gln Leu Gln Lys Gln Asp Gln Leu Ser Val Pro Gln Ile Gln Lys Gln
                595                 600                 605

Thr His Gln Phe Glu Ser Lys Val Lys Arg Lys Leu Gln Pro Phe
610                 615                 620

Ser Glu Tyr Gln Gln Lys Gly Gln Lys Asp His Ile Gln Glu Arg Gln
625                 630                 635                 640

Tyr Ile Gln Gln Glu Phe Thr Ile His Ser Asn Gln Ala Tyr Ser Lys
                645                 650                 655

Val Gln Tyr Ile Gln Thr Ile Gln Thr Ala Thr Pro Tyr Val Pro Gln
                660                 665                 670

Leu Glu Ile Ser Gln Glu Asn Ser Phe Glu Val Gln Pro Ala Tyr Glu
            675                 680                 685

Val Asn Glu Gly Gln Arg Asp Arg Glu Leu Val Ser Tyr Thr Gly His
690                 695                 700

Glu His Gln Asn Phe Val Asp Glu Val Ser Thr Pro Leu Pro Pro Ala
705                 710                 715                 720

Glu Ala Gln Pro Gly Ser Thr Ser Glu Asp Ile Ser Asp Pro Val Ser
                725                 730                 735

Pro Glu His Trp Glu Gln Leu Glu Ser Leu Asp Pro Ser Thr Ile Cys
                740                 745                 750

Ile Arg Lys Thr Phe Asn Leu Ile Arg Asp Ile Ser Glu Ser Leu Val
            755                 760                 765

Ala Asp Pro Glu Gln Pro Glu Ala Glu Ala His Arg Lys Ser Ile Phe
            770                 775                 780

Leu Leu Arg Gln Lys Leu Ala Asp Val Cys His Lys Val Leu Thr Glu
785                 790                 795                 800

Ile Ile His Gly Arg Ala Thr Asp Glu Ile Ile Ser Ile Leu Arg Glu
                805                 810                 815

Ile Leu Glu Gln Thr Lys Glu Ile Pro Pro Arg Pro Thr Pro Lys Arg
            820                 825                 830

Asp Leu Gln Glu Asp Ile Ser Met Gly Leu Glu Ile Leu Lys Lys Ile
            835                 840                 845

Arg Gly Met Leu Ser Gly Trp Tyr Ser Ser Arg Glu Ser Glu Thr Asp
850                 855                 860

Ser Thr Asp Thr Gly Thr Gly Phe Gln Ala Gln Asn Gly Lys Gly Phe
865                 870                 875                 880

Gly Ala Gly Arg Gln Pro Glu Asn Ser Phe Leu Ser Gln Lys Arg Arg
                885                 890                 895

Asn Gln Glu Glu Asn Pro Arg Leu Ile Lys Tyr Arg Arg Val Asp Asn
            900                 905                 910

Ser Phe Pro Arg Leu Ile Thr Asn Glu Thr Ala Glu Asp Leu Ile Pro
            915                 920                 925

Asn Asn Ser Met Ala Lys Arg Asp Gln Pro Gln Ser Ser Lys Arg Leu
930                 935                 940

Ser Ile Phe Asn Pro Pro Val Tyr Thr Gln His Arg Val Arg Asn Asp
945                 950                 955                 960
```

-continued

```
Ala Pro His Val Pro Thr Pro Phe Asp Asp Glu Glu Ser Ser Gln Arg
            965                 970                 975

Leu Ala Asn Ala Gly Pro Ser Ser Arg Pro Met Thr Tyr Ser Asp Ala
            980                 985                 990

Val Arg Leu Gly His Asn Gly Ile Ser Glu Ser Arg Val Asn Gly His
            995                1000                1005

Ser Ser His Thr Val Arg Arg Glu Pro Ser Arg Leu His Arg Ser Ile
           1010                1015                1020

Leu Ser His Glu Met Asn Cys Lys Asp Gln Glu Gln Tyr Asn Glu Leu
1025                1030                1035                1040

Ile Arg Thr Gln Thr Asn Tyr Val Gly Ser Arg Tyr Leu Lys Pro Gly
           1045                1050                1055

Thr Pro Pro Thr Phe Gln Arg Ala Lys Ala Gln Ser Ala Thr Ser Ser
           1060                1065                1070

Ser Cys Ser Leu Gln Asp Asn Gln Ser Asn Ile Thr Asp Ser Phe Pro
           1075                1080                1085

Ser Pro His Gly Arg Ala Asn Pro Glu Leu Thr Glu Tyr Ala Lys Leu
           1090                1095                1100

Ile Asn Arg Gln Glu Asn Glu Glu Asn Arg Ser Pro Ala Pro Gln Gln
1105                1110                1115                1120

Pro Lys Arg Asn Ala Ser Asn Ser Ser Ala Ser His Ala Ser Thr Ile
           1125                1130                1135

Ser Ser Ser Ala Ser Ser Ser Cys Ser Thr Cys Ser Thr Cys Ser Ser
           1140                1145                1150

Ser Asp Thr Glu Pro Met Leu Val Lys Asp Ser Pro Glu Val Lys Glu
           1155                1160                1165

Ala Asn Glu Ala Asn Glu Ala Asn Glu Ala Asn Glu Ala Asn Glu Thr
           1170                1175                1180

Lys Glu Asn Asp Ala Pro Gln Pro Thr Thr Thr Arg Ile Lys Lys Pro
1185                1190                1195                1200

Asp Phe Leu His Arg Arg Phe Ala Asn Cys Ile Phe Leu Arg Asn Asp
           1205                1210                1215

Phe Ala Glu Asn Phe Lys Ala Arg Ala Asn Arg Arg Gln Leu Glu Ser
           1220                1225                1230

Met His Leu Leu Gly Ile Ala Glu Gln Gln Ala Asn Glu Ser Lys Asp
           1235                1240                1245

Glu Arg Leu Ala Tyr Glu Lys Lys Leu Arg Glu Val Met Phe Arg Ser
1250                1255                1260

Gly Ala Pro His Arg Pro Phe Phe Glu Ile Gly Pro Leu Glu Gln Pro
1265                1270                1275                1280

Glu Glu Lys Lys Glu Thr Lys Leu Ile Pro Leu Thr Lys Glu Asp His
           1285                1290                1295

Ala Arg Phe Gln Glu Met Thr Thr Ile Glu Val Thr Thr Asn Leu Ile
           1300                1305                1310

Phe Lys Tyr Asn Leu Gln Ile Thr Thr Asp Asp Ile Phe Thr Phe Val
           1315                1320                1325

Asp Gly Glu Trp Leu Asn Asp Ala Ile Ile Asn Phe Tyr Met Ser Met
           1330                1335                1340

Leu Thr Glu Arg Ser Glu Lys Arg Ala Gly Glu Leu Pro Ala Thr Tyr
1345                1350                1355                1360

Ala Met Asn Thr Phe Phe Met Pro Arg Leu Leu Gln Ala Gly Tyr Ala
           1365                1370                1375

Gly Val Arg Arg Trp Thr Arg Lys Val Asp Leu Phe Ser Lys Asp Ile
```

```
                    1380              1385              1390
Ile Pro Val Pro Val His Cys Gly Asn Val His Trp Cys Met Ala Ile
            1395              1400              1405

Ile His Leu Arg Asn Lys Thr Ile Phe Tyr Tyr Asp Ser Met Gly Arg
        1410              1415              1420

Pro Asn Gln Pro Ala Leu Asp Ala Leu Val Lys Tyr Leu His Glu Glu
1425              1430              1435              1440

Ser Leu Asp Lys Arg Lys Gln Pro Phe Asp Met Thr Gly Phe Val Val
            1445              1450              1455

Glu Asn Ala Gln Asn Ile Pro Arg Gln Gly Asn Ser Asp Cys Gly
            1460              1465              1470

Val Phe Ser Cys Met Phe Ala Glu Tyr Ile Thr Arg Asp Val Pro Ile
            1475              1480              1485

Thr Phe Ser Gln Ala Glu Met Leu Tyr Phe Arg Thr Lys Met Ala Leu
        1490              1495              1500

Glu Ile Ala Asp Gly Lys Leu Trp Gln
1505              1510

<210> SEQ ID NO 80
<211> LENGTH: 242
<212> TYPE: PRT
<213> ORGANISM: Arabidopis Thaliana

<400> SEQUENCE: 80

Met Phe Val Asp Ala Met Gln Asp Leu Ala Leu Val Asn Ser Ala Leu
  1               5                  10                  15

Ser Lys Arg Asn Arg Lys Lys Ile Leu Val Ser His Lys Asn Ser Asn
             20                  25                  30

Ile Asp Ile Ser Gly Glu Thr Leu Gln Cys Leu Arg Pro Asn Gln Trp
         35                  40                  45

Leu Asn Asp Asp Val Thr Asn Leu Tyr Leu Glu Leu Leu Lys Glu Arg
     50                  55                  60

Gln Thr Arg Asp Pro Gln Lys Tyr Phe Lys Cys His Phe Phe Asn Thr
 65                  70                  75                  80

Phe Phe Tyr Val Lys Leu Val Ser Gly Ser Gly Tyr Asn Tyr Lys Ala
                 85                  90                  95

Val Ser Arg Trp Thr Thr Lys Arg Lys Leu Gly Tyr Asp Leu Ile Asp
             100                 105                 110

Cys Asp Ile Ile Phe Val Pro Ile His Ile Asp Ile His Trp Thr Leu
         115                 120                 125

Gly Val Ile Asn Asn Arg Glu Arg Lys Phe Val Tyr Leu Asp Ser Leu
     130                 135                 140

Phe Thr Gly Val Gly His Thr Ile Leu Asn Ala Met Ala Lys Tyr Leu
145                 150                 155                 160

Val Asp Glu Val Lys Gln Lys Ser Gln Lys Asn Ile Asp Val Ser Ser
                 165                 170                 175

Trp Gly Met Glu Tyr Val Glu Arg Pro Gln Gln Asn Gly Tyr
             180                 185                 190

Asp Cys Gly Met Phe Met Leu Lys Tyr Ile Asp Phe Tyr Ser Arg Gly
         195                 200                 205

Leu Ser Leu Gln Phe Ser Gln Val Ile Arg Asp Val Ile Lys Lys Asp
     210                 215                 220
```

```
Met Pro Tyr Phe Arg Leu Arg Thr Ala Lys Glu Ile Leu Arg Leu Arg
225                 230                 235                 240
Ala Asp
```

METHODS AND COMPOSITIONS FOR ENHANCED PROTEIN EXPRESSION AND PURIFICATION

This application is a §371 application of PCT/US2007/089035, filed Dec. 28, 2007, which claims priority under 25 U.S.C. §119(e) to U.S. Provisional Patent Application No. 60/877,914, filed Dec. 29, 2006. The entire disclosure of each of the foregoing applications is incorporated by reference herein.

FIELD OF THE INVENTION

The present invention relates to the field of recombinant cDNA expression and purification of expressed proteins. More specifically, the invention provides materials and methods which enhance expression and facilitate purification of heterologous proteins from a variety of different host species.

BACKGROUND OF THE INVENTION

Several publications and patent documents are cited throughout the specification in order to describe the state of the art to which this invention pertains. Full citations of these references can be found throughout the specification. Each of these citations is incorporated herein by reference as though set forth in full.

Functional genomic studies have been hampered by the inability to uniformly express and purify biologically active proteins in heterologous expression systems (Ryan and Patterson (2002) Trends Biotechnol, 20:S45-51). Despite the use of identical transcriptional and translational signals in a given expression vector, expressed protein levels have been observed to vary dramatically (Weickert et al. (1996) Curr. Opin. Biotechnol., 7:494-9). For this reason, several strategies have been developed to express heterologous proteins in bacteria, yeast, mammalian and insect cells as gene-fusions (Ecker et al. (1989) J. Biol. Chem., 264:7715-9; Butt et al. (1989) Proc. Natl. Acad. Sci., 86:2540-4; Kapust and Waugh (1999) Protein Sci., 8:1668-74; Ikonomou et al. (2003) Appl. Microbiol. Biotechnol., 62:1-20).

The expression of heterologous genes in bacteria is by far the simplest and most inexpensive means available for research or commercial purposes. However, some heterologous gene products fail to attain their correct three-dimensional conformation in *E. coli* while others become sequestered in large insoluble aggregates or "inclusion bodies" when overproduced (Jonasson et al. (2002) Biotechnol. Appl. Biochem., 35:91-105; Georgiou and Valax (1999) Methods Enzymol., 309:48-58.). Major denaturant-induced solubilization methods followed by removal of the denaturant under conditions that favor refolding are often required to produce a reasonable yield of the recombinant protein.

Selection of open reading frames (ORFs) for structural genomics projects has also shown that only about 20% of the genes expressed in *E. coli* render proteins that are soluble or correctly folded (Waldo et al. (1999) Nat. Biotechnol., 17:691-5). These numbers are startlingly disappointing especially given that most scientists rely on *E. coli* for initial attempts to express gene products. Several systems for expressing proteins by conjugation to a tag such as NUS A, maltose binding protein (MBP), glutathione S transferase (GST), and thioredoxin (TRX) have been developed (Jonasson et al. (2002) Biotechnol. Appl. Biochem., 35:91-105). All of these systems have certain drawbacks, ranging from inefficient expression to inconsistent cleavage from desired structure.

Ubiquitin (Ub) and ubiquitin like proteins (Ubls) have been described in the literature (Jentsch and Pyrowolakis (2000) Trends Cell Biol., 10:335-42; Yeh et al. (2000) Gene, 248:1-14; Larsen and Wang (2002) J. Proteome Res., 1:411-9). The SUMO system has also been characterized (Muller et al. (2001) Nat. Rev. Mol. Cell. Biol., 2:202-10.). SUMO (small ubiquitin related modifier) is a Ubl that is also known as Sentrin, SMT3, PIC1, GMP1 and UBL1 in published literature. The SUMO pathway is present throughout the eukaryotic kingdom and SUMO proteins are highly conserved ranging from yeast to humans (Kim et al. (2002) J. Cell. Physiol., 191:257-68). Although overall sequence homology between ubiquitin and SUMO is only 18%, structure determination by nuclear magnetic resonance (NMR) reveals that the two proteins possess a common three dimensional structure characterized by a tightly packed globular fold with n-sheets wrapped around one α-helix (Bayer et al. (1998) J. Mol. Biol., 280:275-86; Kim et al. (2000) J. Biol. Chem., 275:14102-6). Examining the chaperoning properties of SUMO reveals that its attachment to the N-terminus of a labile protein can act as a nucleus for folding and protect the protein from aggregation.

All SUMO genes encode precursor proteins with a short C-terminal sequence that extends beyond the conserved C-terminal Gly-Gly motif (Muller et al. (2001) Nat. Rev. Mol. Cell. Biol., 2:202-10). The extension sequence varies in length and is typically 2-12 amino acids. SUMO proteases (known also as hydrolases) remove the C-terminal extensions prior to sumoylation in the cell (Coloma et al. (1992) J. Immunol. Methods, 152:89-104). Conjugating the C-terminus of SUMO to the ε-amino groups of lysine residues of a target protein is known as sumoylation. Sumoylation of cellular proteins has been proposed to regulate nuclear transport, signal transduction, stress response, and cell cycle progression (Kretz-Remy and Tanguay (1999) Biochem. Cell. Biol., 77:299-309). It is very likely that SUMO signals the translocation of proteins among various cell compartments, however, the precise mechanistic details of this function of SUMO are not known. The similarity between the SUMO pathway and the ubiquitin pathway is remarkable, given the different effects that these two protein modifications permit (Goettsch and Bayer (2002) Front. Biosci., 7:a148-62).

NusA is another fusion tag that promotes solubility of partner proteins presumably due to its large size (Davis et al. (1999) Biotecnol. Bioeng., 65:382-8). Glutathione S-transferase (GST) (Smith and Johnson (1988) Gene, 67:31-40) and maltose binding protein (MBP) (diGuan et al. (1988) Gene, 67:21-30) fusion tags have been proposed to enhance expression and yield of fusion partners as well. However, enhanced expression is not always observed when GST is used as it forms dimers and can retard protein solubility. Another problem with all of these fusion systems is that the desired protein may have to be removed from the fusion. To circumvent this problem, protease sites, such as Factor Xa, thrombin, enterokinase or Tev protease sites are often engineered downstream of the fusion tag. However, inappropriate cleavage is often observed because these proteases recognize a short specific amino acid sequence that might be present within the fusion/target protein (Jonasson et al. (2002) Biotechnol. Appl. Biochem., 35:91-105). The present invention circumvents these problems. Further, unlike SUMO proteases, Tev protease is a sequence specific protease that leaves undesirable sequence at the N-terminus of the protein of interest after cleavage of a fusion protein. In contrast, SUMO proteases cleave any sequence from the C-terminus of SUMO to generate desired N-termini in the fused protein (except for proline).

SUMMARY OF THE INVENTION

In accordance with the instant invention, engineered SUMO proteins which cannot be cleaved by wild-type SUMO proteases are provided. Nucleic acid molecules encoding the engineered SUMO proteins are also provided. In a particular embodiment, the engineered SUMO is a SUMO protein wherein at least one arginine residue in the SUMO protease interaction domain has been altered to another amino acid, preferably a non-basic amino acid. In another embodiment, the engineered SUMO protein comprises the amino acid sequence $X_1FX_2X_3X_4GX_5X_6$ (SEQ ID NO: 2), wherein $X_1$ and $X_6$ are any amino acid other than arginine and $X_2, X_3, X_4,$ and $X_5$ are any amino acid. In another embodiment, $X_1$ is selected from the group consisting of glutamine, threonine, and phenylalanine and $X_6$ is selected from the group consisting of leucine and glutamic acid. In yet another embodiment, the engineered SUMO has at least 90% identity with SEQ ID NO: 1.

In accordance with the instant invention, engineered SUMO proteases which can cleave the engineered SUMO proteins are provided. Nucleic acid molecules encoding the engineered SUMO proteases are also provided. In a particular embodiment, the engineered SUMO protease is a SUMO protease wherein the SUMO interaction domain has been altered. In a more specific embodiment, the engineered SUMO protease comprises the amino acid sequence $WLNX_1X_2X_3X_4X_5$ (SEQ ID NO: 6), wherein $X_1$ and $X_5$ are any non-acidic amino acid and $X_2, X_3, X_4,$ and $X_5$ are any amino acid. In another embodiment, $X_1$ is serine; $X_2$ is selected from the group consisting of glycine and threonine; and $X_5$ is selected from the group consisting of serine, alanine, and methionine. In yet another embodiment, the engineered SUMO protease has at least 90% homology with an amino acid sequence selected from the group consisting of SEQ ID NO: 3, SEQ ID NO: 4, and SEQ ID NO: 5.

In accordance with another aspect of the instant invention, methods for enhancing expression levels of a protein of interest in a host cell are provided. In a particular embodiment, these methods comprise i) operably linking a nucleic acid encoding an engineered SUMO to a nucleic acid sequence encoding a protein of interest thereby generating a construct encoding a fusion protein, and ii) introducing the nucleic acid into the host cell, whereby the presence of the engineered SUMO in the fusion protein increases the expression level of the protein of interest in the host cell. In a particular embodiment, the method further comprises isolating the fusion protein and, optionally, cleaving the fusion protein to release the protein of interest.

In accordance with still another aspect of the instant invention, methods for generating an altered amino terminus in a protein of interest in a host cell are provided. In a particular embodiment, these methods comprise a) providing a nucleic acid sequence encoding the protein of interest; b) altering the N-terminal amino acid coding sequence in the nucleic acid; c) operably linking a nucleic acid encoding an engineered SUMO to the nucleic acid sequence encoding the protein of interest; d) expressing the nucleic acid in a host cell, and e) expressing an engineered SUMO protease capable of cleaving the engineered SUMO in the host cell, whereby the engineered SUMO protease effects cleavage of the engineered SUMO, thereby producing a protein of interest having an altered amino terminus in the cell. In a particular embodiment, the method further comprises the isolation of the protein of interest having an altered amino terminus.

In accordance with yet another aspect of the instant invention, methods for enhancing secretion levels of a protein of interest from a host cell are provided. In a particular embodiment, these methods comprise i) operably linking a nucleic acid molecule encoding an engineered SUMO to a nucleic acid sequence encoding the protein of interest thereby generating a construct encoding a fusion protein, and ii) introducing the nucleic acid into the host cell, whereby the presence of the engineered SUMO in the fusion protein increases the secretion of the protein of interest from the host cell.

Recombinant vectors comprising a nucleic acid molecule encoding an engineered SUMO operably linked to a promoter and a multiple cloning site are also provided. In a preferred embodiment, the multiple cloning site allows for cloning a nucleic acid encoding a protein of interest 3' to the nucleic acid sequence encoding the Gly-Gly cleavage site of the engineered SUMO. In a particular embodiment, the recombinant vector is comprised within a kit which can further comprise host cells and reagents for oligonucleotide-based site-directed mutagenesis for altering the nucleic acid encoding the protein of interest to generate amino termini which are different from the native protein of interest.

In another embodiment, kits for the purification of a protein from a host cell are provided which comprise i) a recombinant vector comprising: a) a nucleic acid molecule encoding an engineered SUMO; b) a promoter; c) a multiple cloning site; and, optionally, d) a nucleic acid sequence encoding for an affinity tag; wherein the promoter is operably linked to the nucleic acid molecule encoding the engineered SUMO, wherein the nucleic acid sequence encoding an affinity tag, if present, is in-frame and operably linked to the nucleic acid molecule encoding the engineered SUMO, and wherein the multiple cloning site allows for cloning a nucleic acid encoding a protein of interest 3' to the nucleic acid sequence encoding the Gly-Gly cleavage site of the engineered SUMO, and ii) a composition comprising an engineered SUMO protease or vector encoding an engineered SUMO protease, wherein the engineered SUMO protease specifically cleaves the engineered SUMO after the Gly-Gly cleavage site. In a particular embodiment, the kits may further comprise at least one host cells, solid support for binding the affinity tag, lysis buffer, wash buffer, elution buffer, cleavage buffer, and instruction material.

In accordance with another aspect of the instant invention, microarrays comprising fusion proteins comprising an engineered SUMO protein linked to a protein of interest are provided.

BRIEF DESCRIPTION OF THE DRAWINGS

FIG. 7 is a schematic illustration of an experimental system used to screen for engineered SUMO proteases capable of cleaving engineered SUMO. β-lactamase confers resistance to ampicilin in E. coli only when it is exported into the periplasmic space. As depicted in FIG. 7A, when β-lactamase is linked with SUMO and an insoluble protein at the N-terminal end, it is trapped inside the cell and the bacteria does not grow on ampicillin containing plates. If SUMO protease is introduced into the cell in addition to β-lactamase complex, the β-lactamase gets released by SUMO protease and is subsequently exported into the periplasm where it confers resistance to ampicillin (FIG. 7B). If the SUMO tag on β-lactamase is mutated in a way that it is not cleaved by wild type SUMO protease (e.g., the SUMO is SUMO*), the cells become sensitive to ampicillin (FIG. 7C). The bacterial cells regain the resistance to ampicillin only when the SUMO protease is mutated/altered in a way that it would cleave the mutant SUMO* (FIG. 7D). Insol. protein=insoluble protein; WT SUMO Protease=wild type SUMO protease; BLA=β-lactamase; SUMO*=Engineered SUMO.

FIG. 10A demonstrates that ULP1 cleaves the SMT3 tag. FIG. 10B demonstrates that SUMO* protease 1 cleaves the SUMO* tag. FIG. 10C demonstrates that ULP1 does not cleave SUMO* tag. FIG. 10D shows that SUMO* protease 1 cleaves wild type SUMO, but less efficiently than SUMO*. U=uncut SUMO or SUMO*-GFP (no protease present); P=protease only lane, the same amount of the protease was used as in the first cutting reaction.

FIGS. 11A-11C provide sequences of SUMO proteins from various species. Underlined region is a region of interaction with SUMO proteases.

FIGS. 12A and 12B provide sequences of SUMO proteases from various species. Underlined region is a region of interaction with SUMO proteins.

DETAILED DESCRIPTION OF THE INVENTION

The instant invention provides novel engineered SUMO proteins that are not cleaved by wild type SUMO proteases in eukaryotic systems and methods of use thereof. Indeed, in order to take advantage of the expression enhancing properties of SUMO, novel engineered SUMO tags (e.g., SUMO*) have been developed which are not cleaved in eukaryotic cells. SUMO proteases are present in all eukaryotes. Therefore, in contrast to the engineered SUMO proteins of the instant invention, wild-type SUMO fusions are cleaved when expressed in eukaryotes. Notably, prokaryotes do not have a SUMO pathway or SUMO proteases. Thus, SUMO fusions (wild-type or engineered) are not cleaved when expressed in prokaryotes.

Figure 1:
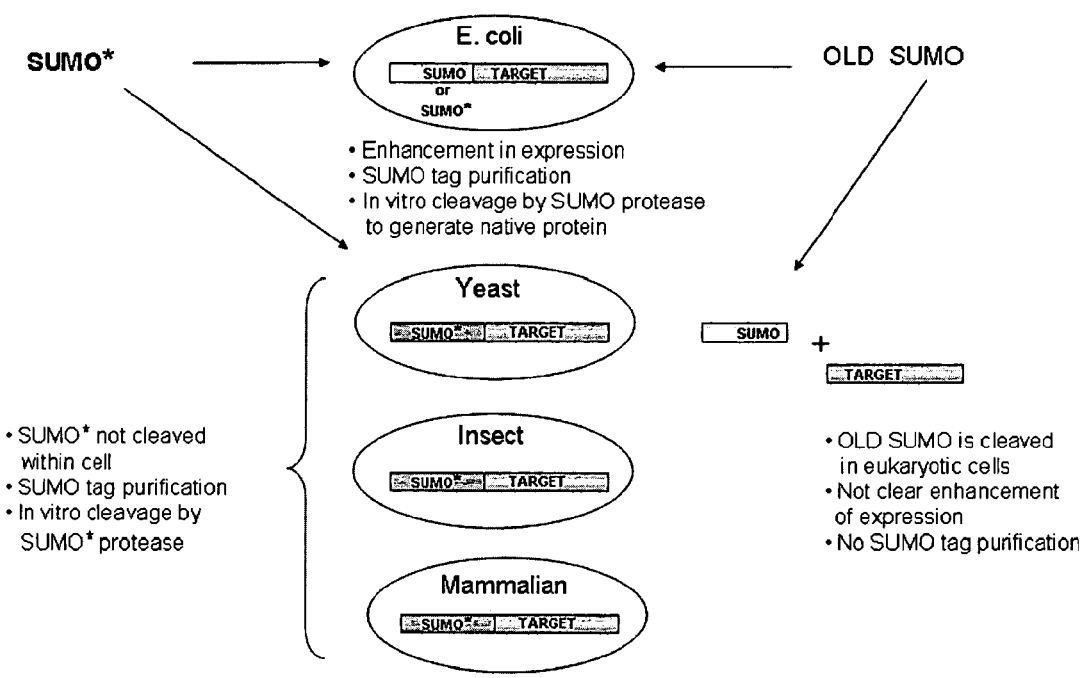
FIG. 1 is a schematic drawing illustrating the potential application of an engineered SUMO tag (e.g., SUMO*) and a corresponding engineered SUMO protease for protein production and purification from prokaryotic and eukaryotic cells as compared to wild-type SUMO and wild-type SUMO protease.

Novel engineered SUMO proteases that can cleave the engineered SUMO proteins are also provided. The engineered SUMO proteins and SUMO proteases enable the expression and purification of proteins of interest fused to the engineered SUMO in both eukaryotic and prokaryotic systems (see, e.g., FIG. 1). The system also allows for the generation of native proteins with a desired N-terminus.

Recombinant proteins may be produced, for example, by inserting a nucleic acid sequence from one organism into a foreign host organism. The foreign host synthesizes the recombinant protein (protein of interest) from the inserted nucleic acid molecule. The produced protein is then typically separated from the cells in subsequent purification steps. Prokaryotic, eukaryotic, bacteria, yeast, insect and mammalian cells can all be used to express recombinant proteins. Protein "tags" have been developed wherein a sequence of DNA is inserted, just before or after, the region encoding the protein of interest. The resultant fusion protein contains the tag and the recombinant protein of interest. Protein tags may enhance solubility, proper folding, level of expression, and the ability to purify the protein of interest.

Many different protein tags have been developed over the years to enhance protein expression and solubility in the bacteria E. coli. Such protein tags include, without limitation, GST (gluthatione S-transferase), MBP (maltose binding protein), Thx (thioredoxin), NusA, Ub (ubiquitin), and SUMO. Although these tags are being successfully used in bacteria, they can not be transferred to eukaryotic cells because of various limitations such as low expression of heterologous proteins or in the case of Ub or SUMO tags the inability to remain as a fusion protein due to endogenous proteases.

The SUMO protein as a fusion partner can greatly enhance the level and quality of recombinant protein expression in both bacterial and eukaryotic cells (see, for example, U.S. Pat. No. 7,060,461; U.S. Patent Application Publication Nos. 20040018591 and 20060040335; and PCT/US04/20778). The SUMO family of proteins is naturally added and removed from eukaryotic proteins as part of cellular regulation. The structure of SUMO and the process of SUMO protein addition and removal is highly conserved in eukaryotic cells. A high degree of structural conservation in SUMO proteins results in cross species reactivity of the SUMO fusion tag with endogenous SUMO modifying enzymes of the foreign host. Eukaryotes are able, therefore, to cleave SUMO tags and in many cases this results in the separation of tag and recombinant protein. The expression and purification of an "uncleaved" or unprocessed wild type SUMO fusion protein from eukaryotic cells is frequently impossible. To overcome this obstacle of "premature" tag cleavage in the pursuit of enhanced protein production in eukaryotic cells, novel SUMO proteins were engineered to be resistant to endogenous SUMO proteases.

The current discovery addresses at least four major problems in the field of protein expression. First, as stated hereinabove, the use of SUMO, Ub, and other ubiquitin-like protein fusions in eukaryotic cells has been limited by instant cleavage of the fusion bond by hydrolases naturally present in eukaryotes. Because of this cleavage, an affinity tag would have to be placed after the cleavage site of SUMO-hydrolase or at the C-terminus of the passenger protein in order to assist the purification the protein of interest. If the affinity tag was to be removed for downstream applications of the fusion protein, a protease site would also have to be engineered. The system presented herein circumvents the restriction of SUMO tags to prokaryotic systems, thus allowing the use of the mutant SUMO proteins of the instant invention or an affinity tag attached to the amino terminus of the mutant SUMO protein for affinity purification of the fusion proteins in all systems including eukaryotic. Engineered SUMO proteases provided herein allow for efficient removal of the tags in vitro or in vivo.

Second, many proteins are unstable or poorly expressed in eukaryotic and prokaryotic cells. Fusion with an engineered SUMO protein causes the proteins to be expressed at significantly higher levels than the unfused protein counterpart (see, e.g., FIG. 3A) and even the protein fused to wild-type SUMO (see, e.g., Example 4). Additionally, as described hereinbelow, fusion with an engineered SUMO protein may facilitate secretion of the protein of interest at levels higher than the unfused protein or even the protein fused to wild-type SUMO. The attachment of a SUMOP molecule to the protein of interest may also stabilize the protein.

Third, certain proteins are toxic to a cell, particularly when expressed heterologously. The attachment of SUMO to these toxic proteins may reduce or eliminate the toxicity of the protein and allow for greater and sustained expression of the previously difficult to express toxic protein. For example, the presence of the SUMO molecule at the amino terminus of the protein may inhibit any toxic activity of the protein localized to that region of the protein. Indeed, as demonstrated hereinbelow in Example 4, the protein $PLA_2$, which is toxic/lethal to cells and requires a free N-terminus for its activity, can be expressed at high levels in eukaryotic cells when fused to an engineered SUMO. Upon expression and purification, the SUMO molecule can be cleaved from the toxic protein, thereby restoring its toxicity and/or activity.

Fourth, a variety of fusions expressed in prokaryotic cells can be cleaved in vitro or in vivo to generate a novel N-termini that was hitherto impossible to generate as nature initiates protein synthesis only from methionine. This feature of the system is particularly useful for proteins for which a specific N-terminus is required to sustain physiological and biochemical activity (e.g. RNA-polymerases, proteases, and cytokines).

I. Definitions

The following definitions are provided to facilitate an understanding of the present invention:

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

When applied to RNA, the term "isolated nucleic acid" may refer to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An isolated nucleic acid (either DNA or RNA) may further represent a molecule produced directly by biological or synthetic means and separated from other components present during its production.

With respect to single stranded nucleic acids, particularly oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA molecule of the invention, to the substantial exclusion of hybridization of the oligonucleotide with single-stranded nucleic acids of non-complementary sequence. Appropriate conditions enabling specific hybridization of single stranded nucleic acid molecules of varying complementarity are well known in the art.

For instance, one common formula for calculating the stringency conditions required to achieve hybridization between nucleic acid molecules of a specified sequence homology is set forth below (Sambrook et al., 1989):

$$Tm=81.5° C.+16.6 \text{ Log } [Na+]+0.41(\%G+C)-0.63 (\%\text{formamide})-600/\#bp \text{ in duplex}$$

As an illustration of the above formula, using [Na+]=[0.368] and 50% formamide, with GC content of 42% and an average probe size of 200 bases, the Tm is 57° C. The Tm of a DNA duplex decreases by 1-1.5° C. with every 1% decrease in homology. Thus, targets with greater than about 75% sequence identity would be observed using a hybridization temperature of 42° C. For example, hybridizations may be performed, according to the method of Sambrook et al. using a hybridization solution comprising: 5×SSC, 5×Denhardt's reagent, 1.0% SDS, 100 µg/ml denatured, fragmented salmon sperm DNA, 0.05% sodium pyrophosphate and up to 50% formamide. Hybridization is carried out at 37-42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes-1 hour at 37.0 in 1×SSC and 1% SDS; (4) 2 hours at 42-65° in 1×SSC and 1% SDS, changing the solution every 30 minutes.

The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated Tm of the hybrid. Wash conditions should be as stringent as possible for the degree of identity of the probe for the target. In general, wash conditions are selected to be approximately 12-20° C. below the Tm of the hybrid. In regards to the nucleic acids of the current invention, a moderate stringency hybridization is defined as hybridization in 6×SSC, 5×Denhardt's solution, 0.5% SDS and 100 µg/ml denatured salmon sperm DNA at 42° C., and washed in 2×SSC and 0.5% SDS at 55° C. for 15 minutes. A high stringency hybridization is defined as hybridization in 6×SSC, 5×Denhardt's solution, 0.5% SDS and 100 µg/ml denatured salmon sperm DNA at 42° C., and washed in 1×SSC and 0.5% SDS at 65° C. for 15 minutes. A very high stringency hybridization is defined as hybridization in 6×SSC, 5×Denhardt's solution, 0.5% SDS and 100 µg/ml denatured salmon sperm DNA at 42° C., and washed in 0.1× SSC and 0.5% SDS at 65° C. for 15 minutes.

The term "probe" as used herein refers to an oligonucleotide, polynucleotide or DNA molecule, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 15-25 or more nucleotides, although it may contain fewer nucleotides. The probes herein are selected to be complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "primer" as used herein refers to a DNA oligonucleotide, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

"Complementary DNA (cDNA)" is a single-stranded DNA molecule that can be formed from an mRNA template by the enzyme reverse transcriptase. Typically, a primer complementary to portions of mRNA is employed for the initiation of reverse transcription. The term "cDNA" may also refer to a double-stranded DNA molecule consisting of such a single-stranded DNA molecule and its complementary DNA strand. The term "cDNA" may also refer to a clone of a cDNA molecule synthesized from an RNA template.

Polymerase chain reaction (PCR) has been described in U.S. Pat. Nos. 4,683,195, 4,800,195, and 4,965,188, the entire disclosures of which are incorporated by reference herein.

The terms "percent similarity", "percent identity" and "percent homology" when referring to a particular sequence are used as set forth in the University of Wisconsin GCG software program.

The term "functional" as used herein implies that the nucleic or amino acid sequence is functional for the recited assay or purpose.

"Natural allelic variants", "mutants" and "derivatives" of particular sequences of nucleic acids refer to nucleic acid sequences that are closely related to a particular sequence but which may possess, either naturally or by design, changes in sequence or structure. By closely related, it is meant that at least about 75%, but often, more than 90%, of the nucleotides of the sequence match over the defined length of the nucleic acid sequence referred to using a specific SEQ ID NO. Changes or differences in nucleotide sequence between closely related nucleic acid sequences may represent nucleotide changes in the sequence that arise during the course of normal replication or duplication in nature of the particular nucleic acid sequence. Other changes may be specifically designed and introduced into the sequence for specific purposes, such as to change an amino acid codon or sequence in a regulatory region of the nucleic acid. Such specific changes may be made in vitro using a variety of mutagenesis techniques or produced in a host organism placed under particular selection conditions that induce or select for the changes. Such sequence variants generated specifically may be referred to as "mutants" or "derivatives" of the original sequence.

The phrase "consisting essentially of" when referring to a particular nucleotide or amino acid means a sequence having the properties of a given SEQ ID NO. For example, when used in reference to an amino acid sequence, the phrase includes the sequence per se and molecular modifications that would not affect the basic and novel characteristics of the sequence.

The term "promoters" or "promoter" as used herein can refer to a DNA sequence that is located adjacent to a DNA sequence that encodes a recombinant product. A promoter is preferably linked operatively to an adjacent DNA sequence. A promoter typically increases an amount of recombinant product expressed from a DNA sequence as compared to an amount of the expressed recombinant product when no promoter exists. A promoter from one organism can be utilized to enhance recombinant product expression from a DNA sequence that originates from another organism. For example, a vertebrate promoter may be used for the expression of jellyfish GFP in vertebrates. In addition, one promoter element can increase an amount of recombinant products expressed for multiple DNA sequences attached in tandem. Hence, one promoter element can enhance the expression of one or more recombinant products. Multiple promoter elements are well-known to persons of ordinary skill in the art.

The term "enhancers" or "enhancer" as used herein can refer to a DNA sequence that is located adjacent to the DNA sequence that encodes a recombinant product. Enhancer elements are typically located upstream of a promoter element or can be located downstream of or within a coding DNA sequence (e.g., a DNA sequence transcribed or translated into a recombinant product or products). Hence, an enhancer element can be located 100 base pairs, 200 base pairs, or 300 or more base pairs upstream or downstream of a DNA sequence that encodes recombinant product. Enhancer elements can increase an amount of recombinant product expressed from a DNA sequence above increased expression afforded by a promoter element. Multiple enhancer elements are readily available to persons of ordinary skill in the art.

The terms "transfected" and "transfection" as used herein refer to methods of delivering exogenous DNA into a cell. These methods involve a variety of techniques, such as treating cells with high concentrations of salt, an electric field, liposomes, polycationic micelles, or detergent, to render a host cell outer membrane or wall permeable to nucleic acid molecules of interest. These specified methods are not limiting and the invention relates to any transformation technique well known to a person of ordinary skill in the art.

A "replicon" is any genetic element, for example, a plasmid, cosmid, bacmid, phage or virus, that is capable of replication largely under its own control. A replicon may be either RNA or DNA and may be single or double stranded.

A "vector" is a replicon, such as a plasmid, cosmid, bacmid, phage or virus, to which another genetic sequence or element (either DNA or RNA) may be attached so as to bring about the replication of the attached sequence or element.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

The term "oligonucleotide," as used herein refers to sequences, primers and probes of the present invention, and is defined as a nucleic acid molecule comprised of two or more ribo- or deoxyribonucleotides, preferably more than three. The exact size of the oligonucleotide will depend on various factors and on the particular application and use of the oligonucleotide.

The term "substantially pure" refers to a preparation comprising at least 50-60% by weight of a given material (e.g., nucleic acid, oligonucleotide, protein, etc.). More preferably, the preparation comprises at least 75% by weight, and most preferably 90-95% by weight of the given compound. Purity is measured by methods appropriate for the given compound (e.g. chromatographic methods, agarose or polyacrylamide gel electrophoresis, HPLC analysis, and the like).

The term "gene" refers to a nucleic acid comprising an open reading frame encoding a polypeptide, including both exon and (optionally) intron sequences. The nucleic acid may also optionally include non-coding sequences such as promoter or enhancer sequences. The term "intron" refers to a DNA sequence present in a given gene that is not translated into protein and is generally found between exons.

The phrase "operably linked," as used herein, may refer to a nucleic acid sequence placed into a functional relationship with another nucleic acid sequence. Examples of nucleic acid sequences that may be operably linked include, without limitation, promoters, cleavage sites, purification tags, transcription terminators, enhancers or activators and heterologous genes which when transcribed and, if appropriate to, translated will produce a functional product such as a protein, ribozyme or RNA molecule. The phrase "operably linked" may also, for example, refer to a nucleic acid sequence encoding a protein of interest placed in functional relationship with a nucleic acid encoding the carboxy-terminal domain of a Ubl such that the catalytic cleavage activity of the carboxy-terminal domain of a Ubl in proteinaceous form leads to the release of the protein of interest.

The phrase "solid support" refers to any solid surface including, without limitation, any chip (for example, silica-based, glass, or gold chip), glass slide, membrane, bead, solid particle (for example, agarose, sepharose, polystyrene or magnetic bead), column (or column material), test tube, or microtiter dish.

The phrases "affinity tag," "purification tag," and "epitope tag" may all refer to tags that can be used to effect the purification of a protein of interest. Purification/affinity/epitope tags are well known in the art (see Sambrook et al., 2001, Molecular Cloning, Cold Spring Harbor Laboratory) and include, but are not limited to: polyhistidine tags (e.g. 6×His), polyarginine tags, glutathione-S-transferase (GST), maltose binding protein (MBP), S-tag, influenza virus HA tag, thioredoxin, staphylococcal protein A tag, the FLAG™ epitope, AviTag epitope (for subsequent biotinylation), dihydrofolate reductase (DHFR), an antibody epitope (e.g., a sequence of amino acids recognized and bound by an antibody), the c-myc epitope, and heme binding peptides.

As used herein, the term "toxic protein" refers to a protein that results in cell death or inhibits cell growth when expressed in a host cell.

As used herein, an "instructional material" includes a publication, a recording, a diagram, or any other medium of expression which can be used to communicate the usefulness of the composition of the invention for performing a method of the invention. The instructional material of the kit of the invention can, for example, be affixed to a container which contains a kit of the invention to be shipped together with a container which contains the kit. Alternatively, the instructional material can be shipped separately from the container with the intention that the instructional material and kit be used cooperatively by the recipient.

As used herein, the terms "modified," "engineered," or "mutant" refer to altered polynucleotide or amino acid sequences. In one embodiment, a polynucleotide sequence encoding a SUMO or a SUMO protease is modified/engineered/mutated by introducing one or more mutations, particularly by site directed mutagenesis. Additionally, libraries of mutant polynucleotides comprising at least one mutation may also be prepared using random mutagenesis or DNA shuffling techniques. In a particular embodiment, the random mutagenesis is limited to desired regions of the polynucleotide, particularly the region(s) believed to encode the amino acids responsible for the interaction between SUMO and SUMO protease. Common mutagenesis techniques are described in Current Protocols in Molecular Biology, Ausubel, F. et al. eds., John Wiley (2006) and U.S. Pat. Nos. 5,605,793; 5,811,238; 5,830,721; 5,834,252; and 5,837,458. As used herein, a "mutation" or "alteration" refers to a variation in the nucleotide or amino acid sequence of a gene as compared to the naturally occurring or normal nucleotide or amino acid sequence. A mutation may result from the deletion, insertion or substitution of at least one nucleotide or amino acid. In a preferred embodiment, the mutation is a substitution (i.e., the replacement of at least one nucleotide or amino acid with a different nucleotide(s) or amino acid residue(s).

As used herein, the term "domain" means a functional portion, segment or region of a protein, or polypeptide. "Interaction domain" refers specifically to a portion, segment or region of a protein, polypeptide or protein fragment that is responsible for the physical affinity of that protein, protein fragment or isolated domain for another protein, protein fragment or isolated domain. Interaction domains can be consecutive amino acid residues in the primary sequence of a protein or may be comprised of amino acid residues from portions of the polypeptide chain that are not close to one another in the primary sequence but are brought together by the tertiary fold of the polypeptide chain.

As used herein, the terms "multiple cloning site" or "polylinker" refer to an artificially created nucleotide sequence comprising at least one restriction site for the purpose of cloning nucleic acid fragments into another nucleic acid such as a vector.

II. Engineered SUMO Proteins

The instant invention encompasses SUMO proteins which cannot be cleaved by SUMO proteases (e.g., Ulp1). The SUMO can be from any eukaryotic species or be a mutated version of any SUMO molecule. In a particular embodiment, the SUMO is yeast or human. In contrast to yeast, four members of SUMO have been described to date in vertebrates: SUMO-1 and close homologues SUMO-2, SUMO-3 and SUMO-4. All of these vertebrate SUMO proteins are encompassed by the instant invention. Examples of SUMO proteins are provided in FIGS. 11A-11C. Examples of nucleic acid sequences encoding human SUMO proteins are also provided at GenBank Accession Nos. NM_003352.4 (SUMO1), NM_001005781.1 (SUMO1), NM_001005782.1 (SUMO1), NM_006937.3 (SUMO2), NM_001005849.1 (SUMO2), NM_006936.2 (SUMO3), and NM_001002255.1 (SUMO4).

In a particular embodiment, the engineered SUMO proteins of the instant invention are cleaved less than 10% by a SUMO protease which cleaves at least 90%, preferably at least 95%, more preferably at least 99%, and still more preferably 100% of the wild-type SUMO under the same reaction conditions (e.g., a standard in vitro cleavage assay or expression in eukaryotic cells). In a more preferred embodiment, the engineered SUMO is cleaved less than 5%, preferably less than 1%, more preferably less than 0.1%, and still more preferably 0% or below levels of detection. As discussed hereinbelow, the engineered SUMO proteins may be cleaved by engineered SUMO proteases.

Engineered SUMO proteins may be generated by altering or changing at least one residue that is in contact with or interacts with the SUMO protease. The residues may be changed to any of the other 20 natural amino acids or to a synthetic or modified amino acid (see, e.g., Table 4 of the MPEP at §2422). The changes may be conservative or non-conservative. A conservative change is the replacement of an amino acid with a one possessing similar properties. For example, Asp and Glu are both acidic amino acids; Lys, Arg, and His are basic amino acids; Asn, Gln, Ser, Thr, and Tyr possess uncharged polar side chains; Ala, Gly, Val, Leu, Ile, Pro, Phe, Met, Trp, and Cys have nonpolar side chains; Ala, Gly, and Leu are small amino acids; Phe, Tyr, and Trp possess large aromatic side chains; and Phe, Tyr, Trp, Val, Ile, and Thr possess bulky uncharged side chains. Accordingly, the replacement of an Asp with a Glu may be considered a conservative change, but replacement of Asp with His would not be a conservative change.

In a particular embodiment, alterations are made within the region which interacts with SUMO protease. As seen in FIG. 11, the regions of SUMO which interact with the SUMO protease are generally within the region from about residue 53 to about residue 72. For example, for yeast SUMO (Smt3) the region is from about residues 63 to 72. In a particular embodiment, at least one of the arginine residues and preferably both arginine residues (or more, if present) are altered (e.g., in Smt3, the arginine residues within the SUMO protease interaction domain are at positions 64 and 71). In a preferred embodiment, the arginine residues are altered to non-basic amino acids. In a particular embodiment, the arginine at position 64 is changed to a threonine and the arginine at position 71 is changed to a glutamic acid. This construct is SUMO* and has the following amino acid sequence (SEQ ID NO: 1):

```
Met Ser Asp Ser Glu Val Asn Gln Glu Ala Lys Pro
1               5                   10

Glu Val Lys Pro Glu Val Lys Pro Glu Thr His Ile
        15              20

Asn Leu Lys Val Ser Asp Gly Ser Ser Glu Ile Phe
25                  30                      35

Phe Lys Ile Lys Lys Thr Thr Pro Leu Arg Arg Leu
            40              45

Met Glu Ala Phe Ala Lys Arg Gln Gly Lys Glu Met
50                      55                  60

Asp Ser Leu Thr Phe Leu Tyr Asp Gly Ile Glu Ile
                65                      70

Gln Ala Asp Gln Thr Pro Glu Asp Leu Asp Met Glu
            75              80

Asp Asn Asp Ile Ile Glu Ala His Arg Glu Gln Ile
85                  90                      95

Gly Gly
```

In another embodiment, the engineered SUMO of the instant invention has at least 75%, 80%, 85%, 90%, 95%, 97%, 99%, or 100% homology with SEQ ID NO: 1, particularly at least 90% or 95% homology. In a particular embodiment, both residues at positions 64 and 71 are not arginines.

In still another embodiment, the engineered SUMO of the instant invention is a SUMO protein (e.g., yeast SUMO (Smt3) or human SUMO1) which has been altered to comprise the sequence (SUMO protease interaction domain):

$X_1FX_2X_3X_4GX_5X_6$  (SEQ ID NO: 2)

wherein $X_1$ and $X_6$ are any amino acid other than arginine and $X_2$, $X_3$, $X_4$, and $X_5$ are any amino acid and may be wild-type (i.e., unmutated). In a particular embodiment, $X_1$ and $X_6$ are any non-basic amino acid. In a preferred embodiment, $X_2$ is L or R; $X_3$ is F, W, or Y, $X_4$ is D or E; and $X_5$ is I, Q, or R. In a particular embodiment, $X_1$ is selected from the group consisting of glutamine, threonine, and phenylalanine, and/or $X_6$ is selected from the group consisting of leucine and glutamic acid at position 71.

In another embodiment, the engineered SUMO of the instant invention is a SUMO protein (e.g., human SUMO2, SUMO3, and SUMO4) which has been altered to comprise the sequence (SUMO protease interaction domain):

$X_1FX_2F$  (SEQ ID NO: 65)

wherein $X_1$ and $X_2$ are any amino acid other than arginine. In a particular embodiment, $X_1$ and $X_2$ are any non-basic amino acid. In a specific embodiment, $X_1$ is an amino acid which possesses an uncharged side chain, particularly threonine, and $X_2$ is an acidic amino acid, particularly glutamic acid.

Preferably, the engineered SUMO protein retains at least one property of the wild-type SUMO. For example, it is preferred that the engineered SUMO increases the expression of a fused protein of interest as well as or better than wild-type SUMO does. The engineered SUMO may also increase secretion and/or solubility of the protein of interest and/or alter the cellular localization of the fused protein of interest.

Nucleic acid molecules encoding the uncleavable SUMO proteins are also encompassed by the instant invention. Nucleic acid molecules encoding the engineered SUMO of the invention may be prepared by any method known in the art. The nucleic acid molecules may be maintained in any convenient vector, particularly an expression vector. Different promoters may be utilized to drive expression of the nucleic acid sequences based on the cell in which it is to be expressed. Antibiotic resistance markers are also included in these vectors to enable selection of transformed cells. Engineered SUMO encoding nucleic acid molecules of the invention include cDNA, DNA, RNA, and fragments thereof which may be single- or double-stranded. The instant invention also encompasses primers, oligonucleotides, probes, antisense molecules, and siRNA molecules directed to or hybridizing with the nucleic acid molecules encoding the engineered SUMO proteins, preferably to the region(s) mutated from the wild-type sequence such that they hybridize preferentially or exclusively to the mutant SUMO compared to the wild-type SUMO.

The present invention also encompasses antibodies capable of immunospecifically binding to engineered SUMO proteins. Polyclonal and monoclonal antibodies directed toward an engineered SUMO may be prepared according to standard methods. In a preferred embodiment, the antibodies react immunospecifically with the altered region of the mutant uncleavable SUMO as compared to wild-type SUMO. Polyclonal or monoclonal antibodies that immunospecifically interact with mutant uncleavable SUMO proteins can be utilized for identifying and purifying such proteins. The antibodies may be immunologically specific for the engineered SUMO to the exclusion of wild-type SUMO or may be cross-reactive to both.

The engineered SUMO proteins of the instant invention may also be posttranslationally modified. The engineered SUMO proteins may be posttranslationally modified in a cell or in vitro. Posttranslational modifications (PTM) of amino acids can alter the structure, activity, function, and stability of a protein. PTMs generally involve the addition of biochemical functional groups such as, without limitation, acetate, phosphate, lipids, and carbohydrates to the amino acids of the proteins. How a protein is posttranslationally modified can be altered by altering the amino acid sequence of the protein. For example, altering the amino acid sequence of a protein to contain either the sequence Asn-X-Ser or Asn-X-Thr may result in the asparagine being glycosylated.

PTMs include, without limitation, acetylation (the addition of an acetyl group, usually at the N-terminus of the protein), alkylation (the addition of an alkyl group (e.g. methyl, ethyl)), methylation (the addition of a methyl group, usually to a lysine or arginine residue), biotinylation (acylation of conserved lysine residues with a biotin appendage), glutamylation (covalent linkage of glutamic acid residues to tubulin or other protein), glycylation (covalent linkage of at least one glycine residues to the tubulin C-terminal tail), glycosylation (the addition of a glycosyl group to either asparagine, hydroxylysine, serine, or threonine, thereby resulting in a glycoprotein), isoprenylation (the addition of an isoprenoid group (e.g., farnesol and geranylgeraniol), lipidation (addition of a lipid), lipoylation (the attachment of a lipoate functionality), phosphopantetheinylation (the addition of a 4'-phosphopantetheinyl moiety from coenzyme A, as in fatty acid, polyketide, non-ribosomal peptide and leucine biosynthesis), phosphorylation (the addition of a phosphate group, usually to serine, tyrosine, threonine or histidine), sulfation (the addition of a sulfate group to a tyrosine), selenation, and C-terminal amidation. Posttranslational modifications are well known to those of skill in the art (see, e.g., Creighton, T. E., Proteins—Structure and Molecular Properties. 2nd Ed., W. H. Freeman and Company, New York, 1993; Wold, F., Posttranslational Covalent Modification of Proteins, Academic Press, New York. 1983; Seifter et al., "Analysis for protein modifications and nonprotein cofactors" (1990) Meth. Enymol., 182:626-646; and Rattan et al., "Protein Synthesis: Posttranslational Modifications and Aging" (1992) Ann. N.Y. Acad. Sci., 663: 48-62).

The engineered SUMO proteins of the instant invention may comprise at least one affinity tag, preferably at the amino-terminus. In a particular embodiment, the affinity tag is heme binding peptide. Full length cytochrome C (CYC7, GenBank Accession No. AAA34940) has a peroxidase activity once a heme co-factor is attached to it (Sander C. Translocation and maturation of c-type cytochromes. Ph.D. Theses. 2001. University of Osnabrueck, Germany). A peptide comprising the heme binding motif of cytochrome C, such as CYC7, can be used as an affinity tag for the engineered SUMO proteins of the instant invention or any protein of interest. An exemplary heme binding peptide comprises the heme binding motif CQQCH (SEQ ID NO: 63). A specific example of a heme binding peptide is GSAKKGATLFK-TRCQQCH (SEQ ID NO: 64). Heme binding peptides can be about 5 to about 50 amino acids in length, preferably about 5 to about 25 amino acids in length, more preferably about 5 to about 20 amino acids in length, and more preferably about 5 to about 15 amino acids. Heme binding peptides have peroxidase activity. Notably, this activity is not destroyed by subjecting the peptide to denaturing SDS-PAGE analysis and blotting the peptide to a membrane. Accordingly, the affinity tag allows for its detection without antibodies by only the use of a peroxidase substrate. Additionally, the heme binding peptide causes the covalently attached protein of interest to appear red, allowing for easy detection and tracking during purification. The heme binding peptide has a very high bind-

III. Engineered SUMO Proteases

The instant invention also encompasses engineered SUMO proteases which can cleave the engineered SUMO proteins, which cannot be cleaved by wild-type SUMO protease. The SUMO protease can be from any eukaryotic species. In a particular embodiment, the SUMO protease is from the same species as the engineered SUMO sought to be cleaved. Examples of SUMO proteases include ULP1 and SENP 1 through 5 and certain amino acid sequences are provided in FIGS. 12A-12B.

In a particular embodiment, the engineered SUMO proteases of the instant invention can cleave at least 50%, preferably at least 75%, 90%, or 95%, more preferably at least 99%, and still more preferably 100% of the engineered SUMO.

Engineered SUMO proteases may be generated by altering or changing at least one residue that is in contact with or interacts with the wild-type SUMO or engineered SUMO. The residues may be changed to any of the other 20 natural amino acids or to a synthetic or modified amino acid. The changes may be conservative or non-conservative.

In a particular embodiment, alterations are made within the SUMO interaction domain of the SUMO protease (see, e.g., FIG. 12). For example, the SUMO interaction domain of yeast ULP1 corresponds to about residues 446 to 460, and more preferably about 451 to 455. In a particular embodiment, at least one of residues 451, 452, and 455 is altered. Preferably, at least residues 451 and 455 are altered and, more preferably, all three amino acids are altered. In particular, the aspartic acid at position 451 is changed to a serine, the threonine residue at position 452 is changed to glycine, and the glutamic acid residue at position 455 is changed to a serine. This construct has the following amino acid sequence (SEQ ID NO: 3):

```
  1 MSVEVDKHRN TLQYHKKNPY SPLFSPISTY RCYPRVLNNP SESRRSASFS GIYKKRTNTS

61 RFNYLNDRRV LSMEESMKDG SDRASKAGFI GGIRETLWNS GKYLWHTFVK NEPRNFDGSE

121 VEASGNSDVE SRSSGSRSSD VPYGLRENYS SDTRKHKFDT STWALPNKRR RIESEGVGTP

181 STSPISSLAS QKSNCDSDNS ITFSRDPFGW NKWKTSAIGS NSENNTSDQK NSYDRRQYGT

241 AFIRKKKVAK QNINNTKLVS RAQSEEVTYL RQIFNGEYKV PKILKEERER QLKLMDMDKE

301 KDTGLKKSII DLTEKIKTIL IENNKNRLQT RNENDDDLVF VKEKKISSLE RKHKDYLNQK

361 LKFDRSILEF EKDFKRYNEI LNERKKIQED LKKKKEQLAK KKLVPELNEK DDDQVQKALA

421 SRENTQLMNR DNIEITVRDF KTLAPRRWLN SGIISFFMKY IEKSTPNTVA FNSFFYTNLS

481 ERGYQCVRRW MKRKKTQIDK LDKIFTPINL NQSHWALGII DLKKKTIGYV DSLSNGPNAM

541 SFAILTDLQK YVMEESKHTI GEDFDLIHLD CPQQPNGYDC GIYVCMNTLY GSADAPLDFD

601 YKDAIRMRRF IAHLILTDAL K
``` ing affinity to cytochrome lyase (CYC3, e.g., GenBank Accession No. AAC04992.1). CYC3 could be immobilized on a solid surface and used as affinity resin to purify proteins that contain a heme binding peptide.

In a particular embodiment, the SUMO protease may have a deletion of or within the amino-terminus (e.g., up to and including residue 402). An exemplary amino acid sequence of a truncated SUMO protease is (SEQ ID NO: 4):

```
401 MGLVPELNEK DDDQVQKALA

421 SRENTQLMNR DNIEITVRDF KTLAPRRWLN SGIISFFMKY IEKSTPNTVA FNSFFYTNLS
```

```
481 ERGYQGVRRW MKRKKTQIDK LDKIFTPINL NQSHWALGII DLKKKTIGYV DSLSNGPNAM

541 SFAILTDLQK YVMEESKHTI GEDFDLIHLD CPQQPNGYDC GIYVCMNTLY GSADAPLDFD

601 YKDAIRMRRF IAHLILTDAL K
```

SUMO* protease 1 is a truncated SUMO protease with a 6× histidine tag and has the amino acids sequence (SEQ ID NO: 5):

```
401 MGLVPELNEK DDDQVQKALA

421 SRENTQLMNR DNIEITVRDF KTLAPRRWLN SGIISFFMKY IEKSTPNTVA FNSFFYTNLS

481 ERGYQGVRRW MKRKKTQIDK LDKIFTPINL NQSHWALGII DLKKKTIGYV DSLSNGPNAM

541 SFAILTDLQK YVMEESKHTI GEDFDLIHLD CPQQPNGYDC GIYVCMNTLY GSADAPLDFD

601 YKDAIRMRRF IAHLILTDAL KLEHHHHHH
```

In another embodiment, the engineered SUMO protease of the instant invention has at least 75%, 80%, 85%, 90%, 95%, 97%, 99%, or 100% homology with SEQ ID NO: 3, 4, or 5, particularly at least 90% or 95% homology. In a particular embodiment, the residue at position 451 is not an aspartic acid, more preferably not an acidic amino acid; the residue at position 455 is not a glutamic acid, more preferably not an acidic amino acid; and, optionally, the residue at position 452 is not threonine.

In still another embodiment, the engineered SUMO protease of the instant invention is a SUMO protease which has been engineered to comprise the sequence:

$$WLNX_1X_2X_3X_4X_5 \quad\quad (SEQ\ ID\ NO:\ 6)$$

wherein $X_1$ and $X_5$ are any non-acidic amino acid and $X_2$, $X_3$, and $X_4$ are any amino acid and may be wild-type (i.e., unmutated). In a particular embodiment, $X_1$ is an uncharged polar side chain amino acid, a nonpolar side chain amino acid, or a small amino acid. $X_5$ may be an uncharged polar side chain amino acid, a nonpolar side chain amino acid, or a small amino acid. In another embodiment, $X_3$ is I or V and $X_4$ is I or T. In a particular embodiment, $X_1$ is serine; $X_2$ is selected from the group consisting of glycine and threonine; and/or $X_5$ is selected from the group consisting of serine, alanine, and methionine.

Nucleic acid molecules encoding the engineered SUMO proteases are also encompassed by the instant invention. Nucleic acid molecules encoding the engineered SUMO proteases of the invention may be prepared by any method known in the art. The nucleic acid molecules may be maintained in any convenient vector, particularly an expression vector. Different promoters may be utilized to drive expression of the nucleic acid sequences based on the cell in which it is to be expressed. Antibiotic resistance markers are also included in these vectors to enable selection of transformed cells. Engineered SUMO protease encoding nucleic acid molecules of the invention include cDNA, DNA, RNA, and fragments thereof which may be single- or double-stranded. The instant invention also encompasses primers, oligonucleotides, probes, antisense molecules, and siRNA molecules directed to or hybridizing with the nucleic acid molecules encoding the engineered SUMO proteases, preferably to the region(s) mutated from the wild-type sequence such that the nucleic acid molecules hybridize preferentially or exclusively to the engineered SUMO protease compared to the wild-type SUMO protease.

The present invention also encompasses antibodies capable of immunospecifically binding to engineered SUMO proteases. Polyclonal and monoclonal antibodies directed toward an engineered SUMO protease may be prepared according to standard methods. In a preferred embodiment, the antibodies react immunospecifically with the altered region of the engineered SUMO protease as compared to wild-type SUMO protease. Polyclonal or monoclonal antibodies that immunospecifically interact with engineered SUMO proteases can be utilized for identifying and purifying such proteins. The antibodies may be immunologically specific for the engineered SUMO protease to the exclusion of wild-type SUMO protease or may be cross-reactive to both.

The engineered SUMO proteases of the instant invention may also be posttranslationally modified as described hereinabove. The engineered SUMO proteases may be posttranslationally modified in a cell or in vitro.

The engineered SUMO proteases of the instant invention may comprise at least one affinity tag, preferably at the amino-terminus. In a particular embodiment, the affinity tag is heme binding peptide, as described hereinabove.

IV. Methods of Use

The fusion protein technology of the instant invention has several applications in production and purification of proteins and peptides. Exemplary methods using this technology include, without limitation:

(1) To enhance expression of proteins and peptides (proteins of interest), particularly those that are poorly expressed, as C-terminal fusions to the engineered SUMO proteins. The SUMO-fusion protein configuration is not cleaved during expression in either prokaryotes (e.g., E. coli; see FIG. 2) or eukaryotes (yeast and insect cells; see FIG. 3), unless an engineered SUMO protease is also transformed into the cell. Exemplary proteins of interest include, without limitation, multimeric proteins, cytokines, vaccines, enzymes, growth factors, receptors, interferons, hematopoeitic agents, albumin, insulin, and hormones.

(2) The engineered SUMO proteins can be fused with an affinity tag. Preferably, the affinity tag is placed at the amino-terminus of the engineered SUMO and the protein of interest is added to the carboxy-terminus of the engineered SUMO protein. The affinity tag allows for the purification of the fusion protein and the protein of the interest can be obtained through the cleavage of the engineered SUMO by an engineered SUMO protease of the instant invention.

(3) The engineered SUMO can be used to purify a protein of interest, i.e., in the absence of an affinity tag. The engineered SUMO can be linked to the N-terminus of the protein of interest. The fusion protein can be expressed and then purified by agents which specifically bind the engineered SUMO, such as immunologically specific antibodies. The protein of interest may then be cleaved from the fusion protein by an engineered SUMO protease of the instant invention.

(4) The engineered SUMO proteases may be used to cleave fusion proteins comprising the engineered SUMO in vitro. The cleavage may occur, for example, in solution when the fusion protein is bound to a solid support via interactions with SUMO or an affinity tag, if present.

(5) The engineered SUMO and SUMO proteases can be removed from post-cleavage mixtures of engineered SUMO containing fusion proteins, which may also contain an affinity tag, by contacting the reaction mixture with a solid support comprising agents which specifically bind the engineered SUMO and/or SUMO protease, such as immunologically specific antibodies.

(6) Affinity tagged engineered SUMO and affinity tagged engineered SUMO proteases can be removed from post-cleavage mixtures by contacting the reaction mixture with a solid support comprising the affinity ligand (e.g. hexahistidine tagged engineered SUMO or SUMO protease can be removed using metal chelate affinity chromatography).

(7) The instant invention allows for proteins of interest to be generated with any amino acid at the amino terminus. For example, fusion proteins can be generated with the protein of interest linked to the carboxy-terminus of an engineered SUMO. The codon encoding the amino-terminal residue of the protein of interest can be altered by directed mutagenesis to encode for the desired amino acid or create a library encompassing more than one amino acid encoded by the mutated codon. The mutagenesis can occur before or after linking to the engineered SUMO. Engineered SUMO protease may then be used in vivo or in vitro after the fusion protein, optionally containing an affinity tag, is expressed to cleave the engineered SUMO from the fusion protein in order to liberate the protein of interest with altered amino-terminus.

(8) Fusion proteins comprising an engineered SUMO can be expressed in prokaryotic and/or eukaryotic cells to generate peptide libraries.

(9) Fusion proteins comprising an engineered SUMO linked to a protein of interest and, optionally an affinity tag, may be expressed in prokaryotic and/or eukaryotic cells to generate peptide libraries. The expressed protein library can then be purified via the engineered SUMO or the affinity tag. Optionally, the engineered SUMO and affinity tag, if present, may be cleaved from the fusion proteins with an engineered SUMO protease to generate a library of pure proteins or peptides by isolation of the library form the cleaved tags.

(10) cDNA libraries of fusion proteins comprising an engineered SUMO and, optionally, an affinity tag may be generated. These cDNA libraries may be used to express the fusion proteins in any host.

(11) Expressed fusion proteins comprising an engineered SUMO and, optionally, an affinity tag, may also be immobilized on a solid support. In a particular embodiment, the fusion proteins comprise a library of proteins of interest and are arranged in an array on the solid support. The fusion proteins may be immobilized to the solid support through the SUMO tag or the affinity tag. Generated arrays may be used, for example, to detect and/or quantitate protein interactions with the immobilized proteins of interest.

V. Kits

The present invention also encompasses kits for use in effecting enhanced expression, secretion, purification, localization, and alteration of the amino terminus of a protein of interest. Such kits comprise at least one recombinant vector containing a nucleic acid sequence encoding an engineered SUMO operably linked to a promoter suitable for expression in the desired host cell and a multiple cloning site suitable for cloning a nucleic acid encoding the protein of interest in-frame with the nucleic acid sequence encoding the engineered SUMO. The promoter is preferably a strong promoter and may be constitutive or regulated. Such promoters are well known in the art and include, but are not limited to, CMV, RSV, SV40, ADH1, T7, and CUP1 promoters.

The recombinant vector may also contain a nucleic acid sequence encoding at least one affinity tag in-frame with the sequence encoding the engineered SUMO. Preferably, the nucleic acid sequence encoding the affinity tag is operably linked to 5' end of the sequence encoding the engineered SUMO. Reagents including, but not limited to, at least one solid support (e.g., one capable of binding at least one of the affinity tags), lysis buffers, wash buffers, and elution buffers may also be included in the kits to assist in the purification of the expressed fusion protein.

The kit may further comprise at least one engineered SUMO protease for cleaving the engineered SUMO. The engineered SUMO protease may be provided as a nucleic acid molecule encoding the engineered SUMO (e.g., an expression vector) and/or as the expressed protein in solution. The engineered SUMO protease may optionally have an affinity tag which is the same or different from the affinity tag attached to the engineered SUMO. The kits may also further comprise at least one cleavage buffer, frozen stocks of host cells, and/or instruction manuals.

The kits may also further comprise reagents for altering the nucleic acid encoding a protein of interest to generate amino termini which are different from those native to the wild-type protein. Methods for altering the nucleic acid are well known in the art and include, but are not limited to, site-directed mutagenesis and oligonucleotide-based site-directed mutagenesis (see, e.g., Ausubel et al., eds., 2006, Current Protocols in Molecular Biology, John Wiley and Sons, Inc.). Exemplary reagents include, without limitation, a DNA polymerase, PCR buffers, and a solution of dNTPs.

The following examples are provided to illustrate various embodiments of the present invention. The examples are illustrative and are not intended to limit the invention in any way.

Example I

Materials and Methods

To co-express SMT3-GFP and ULP1 protease in the same E. coli cell, the T7-SMT3-GFP cassette was amplified from pET24d-Smt3-GFP vector (Malakhov et al. (2004).1. Struct. Funct. Genomics, 5: 75-86) with primers 23 (5'-GGCGCTC-GAGTCCCGCGAAATTAATACGACTCA-3'; SEQ ID NO: 7) and 46 (5'-CGCAAAGCTTGAGCTCTTACTTGTA-CAGCTCGTCCATGCCGA-3'; SEQ ID NO: 8), digested with XhoI and HindIII and inserted into pACYC177 vector (GenBank Accession No. X06402) cut with XhoI and HindIII. This manipulation replaced Kan resistance gene in pACYC177 with SMT3-GFP expression cassette and resulted in the pACYC-SMT3-GFP vector. pACYC-SMT3-GFP was transformed into BL21(DE3) competent cells. The cells carrying pACYC-SMT3-GFP were grown on ampicillin containing media and were made competent using standard $CaCl_2$ method. These competent cells were transformed with another vector carrying ULP1 protease under inducible T7 promoter, pET24-ULP1, described previously (Malakhov et al. (2004) J. Struct. Funct. Genomics, 5: 75-86). Transformants were selected on the LB media with ampicillin and kanamycin. The SMT3-GFP fusion in the cells co-expressing ULP1 protease was processed into SMT3 (20 kD) and GFP (28 kD) when induced with IPTG. The cells not co-expressing ULP1 produced full length SMT3-GFP fusion, 48 kD in size.

To randomize the positions R64 and R71, two overlapping PCR products were produced using pACYC-SMT3-GFP as a template. The first PCR was with primers 23 and 80 (5'-AATACCGTCGTACAAGAANNNTAAGGAGTCCA-3'; SEQ ID NO: 9) the second with primers 79 (5'-TCTTGTAC-GACGGTATTNNNATTCAAGCTGATCAGA-3'; SEQ ID NO: 10) and 46. The two PCR fragments were gel isolated, mixed and used as a template for a secondary PCR with primers 23 and 46. The resulting library of mutant SUMO-GFP fragments was cloned into XhoI-HindIII digested pACYC177 vector. The ligation mixture was transformed into BL21(DE3) competent cells carrying pET24-ULP1 plasmid.

For the selection of engineered SUMOs, the transformed colonies were grown in LB media supplemented with ampicillin and kanamycin to OD-0.5 and then induced with 1 mM IPTG. The induction continued for 12 hours at 20° C. After harvesting, the cells were frozen and stored at −80° C. The pellet was re-suspended in the 10 mM TRIS buffer pH-8.0 containing 1 mM EDTA and 1 unit/ml lysozyme. After a 10-minute incubation at room temperature, $MgCl_2$ was added to the final concentration of 10 mM and DNaseI to the concentration of 10 units/ml. After the 10-minute incubation, 1 µl of dye was and the samples and they were loaded on 12% native polyacrylamide gel without sodium dodecyl-sulphate (SDS). Gels were run at 15 V/cm for 1 hour and visualized on 365 nM UV box.

The β-lactamase construct shown in the FIG. 7 was created in the following way. The β-lactamase gene was amplified in two consecutive PCR reactions with oligo pairs 65 (5'-CGC-GACATATGAGGGTGCTTGTACTAGCTCT-TGCTGTGGCTCTCGCAGT-3'; SEQ ID NO: 11)/61 (5'-CGCGAGGTCTCAACCTCCAATCTGTTCGCGGTGAG-CCT-3'; SEQ ID NO: 12) and 66 (5'-CGCGCAG-GTCTCTAGGTAGGGTGCTTGTAC-TAGCTCTTGCTGTGGCT-CTCGCAGT-3'; SEQ ID NO: 13)/61 or 67 (5'-CGCGCAGGTCTCTAGGTCCTAGGGT-GCTTGTACTAGCTCTTGCTGTGGCTC TCGCAGT-3'; SEQ ID NO: 14)/61 for β-lactamase starting with proline. The resulting β-lactamase had 15 amino acid secretion signal fused to β-lactamase open reading frame (ORF). Mutant SUMO was amplified with oligos 26 (5'-TGTACAGAGCT-CACGCGTGCATGCTCGGACTCAGAAGTCAATCA-3'; SEQ ID NO: 15) and 61. The resulting SUMO and β-lactamase PCR products were digested with Eco31I restriction endonuclease and ligated together. The ligation product was used as a template for the PCR reaction with oligos 26 and 59 (5'-CGCGAGTCGACTTACCAATGCTTAAT-CAGTGAGGCA-3'; SEQ ID NO: 16) and yielded the fusion product (mutant SUMO)-(secretion signal)-(β-lactamase). To add insoluble protein MMP13 to the N-terminus of mutant SUMO, the ORF of MMP13 in the expression cassette together with T7 promoter was amplified from p24d-MMP13 vector with oligos 60 (5'-GGCGAAGCTTTCCCGC-GAAATTAATACGACTCA-3'; SEQ ID NO: 17) and 35 (5'-CGCAGCATGCGGGGTCTTCATCTCCTGGACCA-3'; SEQ ID NO: 18). The resultant product T7-MMP13 was digested with HindIII and SphI and was cloned in three piece ligation together with SphI-SalI digested (mutant SUMO)-(secretion signal)-β-lactamase) into HindIII-SalI digested pACYC184. This resulted into pACYC-mutSUMO-Lac plasmid.

To create a ULP1 expression vector under arabinose inducible promoter P-BAD, the LacI gene along with T7 promoter in pET24d-ULP1 was replaced with the AraC gene and P-BAD promoter. Specifically, the pBAD/His/A vector (Invitrogen) was digested with NcoI and AccI and the fragment carrying araC gene and P-BAD promoter gel isolated. This fragment was ligated into NcoI-AccI digested pET24d-ULP1 yielding a pARA-6His-ULP plasmid.

To mutagenize ULP1, the 5' end of the gene was amplified with oligos 88 (5'-GGAATTAACCATGGGTCATCACCAT-CATCATCACGGAGGT-3'; SEQ ID NO: 19) and 91 (5'-TTAGCCATCTTCGTGGTGCCAAGGTCT-3'; SEQ ID NO: 20), whereas the 3' portion was amplified introducing mutations with oligos 191 (5'-AAGACCTTGGCACCAC-GAAGATGGCTAAATNNNNNNATCATTNNNTTTTT TATGA-3'; SEQ ID NO: 21) and 89 (5% GTGGTGCTC-GAGTCATTTTAAAGCGTCGGTTA-3'; SEQ ID NO: 22), or 192 (5'-AAGACCTTGGCACCACGAAGATG-GCTAAATNNNNNNNNNNNNNNTTTTT TATGA-3'; SEQ ID NO: 23) and 89. 5' and 3' parts were gel isolated and used in the secondary PCR as a template to amplify a mutagenized ULP1 (i.e., mutant SUMO protease) with primers 88 and 89. The resulting PCR was digested with NcoI and XhoI and cloned into pARA-6His vector.

The library of mutant SUMO proteases was transformed into competent TOP10 *E. coli* carrying the pACYC-mut-SUMO-Lac plasmid. After the heat shock at 42° C., the cells were revitalized for 1 hour at 37° C. in 2xYT media. Then four volumes of LB media was added and cells were agitated at 37° C. for 2 hours. The cells were plated on the LB plates supplemented with 34 mg/L chloramphenicol, 50 mg/L kanamycin, 50 mg/L ampicillin and 0.02% arabinose. The plasmids that carry unmutated Ulp1 gene do not support the growth on ampicillin. The positive mutant clones, that grew, were sequenced and used for protease purification for in vitro cutting. The mutant SUMO protease was purified using standard Ni-sepharose method and used in the standard cutting reaction as described previously (Marblestone et al. (2006) Protein Sci., 15:182-9). (Mutant SUMO)-GFP was used as a substrate in the cutting reaction.

Results

Figure 2:
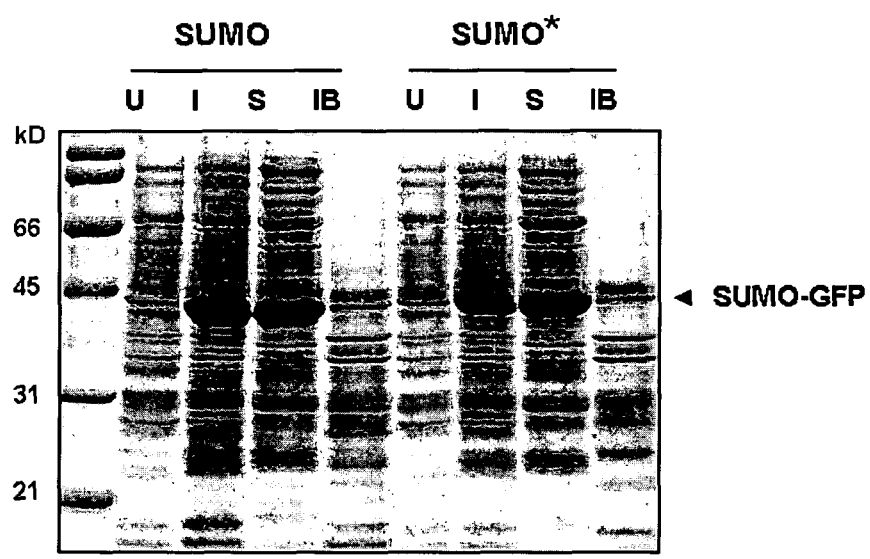
FIG. 2 is an image of a Coomassie stained SDS-PAGE gel demonstrating that SUMO* strongly enhances the expression and solubility of its fusion partner (GFP in this experiment) in bacteria cells compared to untagged GFP, as with wild-type SUMO. U=uninduced culture; I=induced culture; S=soluble fraction; IB=inclusion bodies, insoluble.

The SUMO protein, when linked to a protein of interest as a fusion partner, can greatly enhance the level and quality of recombinant protein expressed in both bacterial and eukaryotic cells (see FIG. 2 and FIG. 3A; Malakhov et al. (2004) J. Struct. Funet. Genom., 5:75-86). The SUMO family of proteins is naturally added and removed from eukaryotic proteins as part of cellular regulation. The structure of SUMO and the process of SUMO protein addition and removal are highly conserved in eukaryotic cells. A high degree of structural conservation in SUMO proteins results in cross species reactivity of the SUMO fusion tag with endogenous SUMO modifying enzymes of the foreign host. Accordingly, eukaryotes are able to cleave SUMO tags and this cleavage generally results in the separation of the tag from the recombinant protein. The expression and purification of an "uncleaved" or unprocessed wild type SUMO fusion protein from eukaryotic cells is, therefore, not readily possible.

To overcome the obstacle of "premature" tag cleavage in the pursuit of enhanced protein production in eukaryotic cells, a novel SUMO protein, called SUMO* was engineered to be resistant to endogenous SUMO proteases. The *Saccharomyces cerevisiae* gene SMT3 was used as the genetic basis for developing such a SUMO Tag.

Figure 4A:
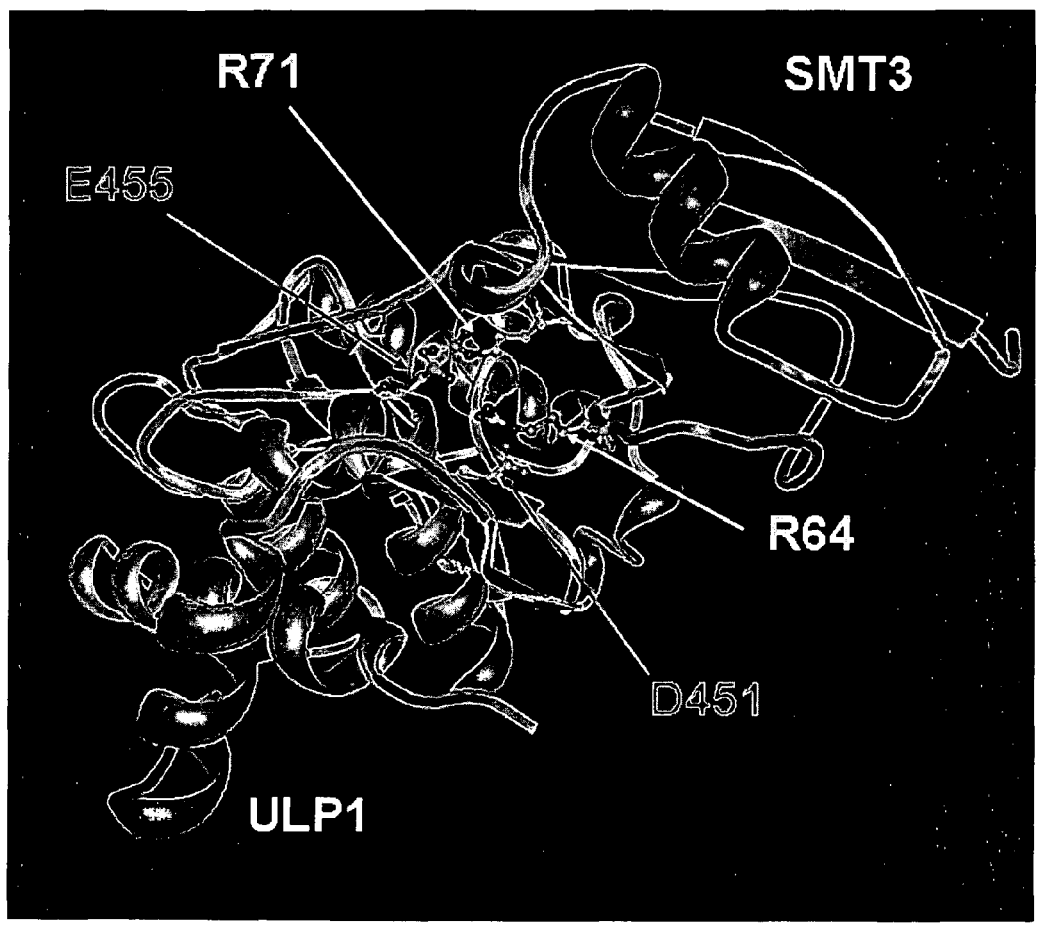
FIGS. 4A and 4B are crystal structures of Smt3 and ULP1 and their potential interactions. Two residues in SUMO (arginine 64 and arginine 71) and two residues in ULP1 (glutamic acid 455 and aspartic acid 451), which are part of the SUMO-ULP1 interaction, are specifically depicted. Different angles of view are shown in FIGS. 4A and 4B.
Figure 4B:
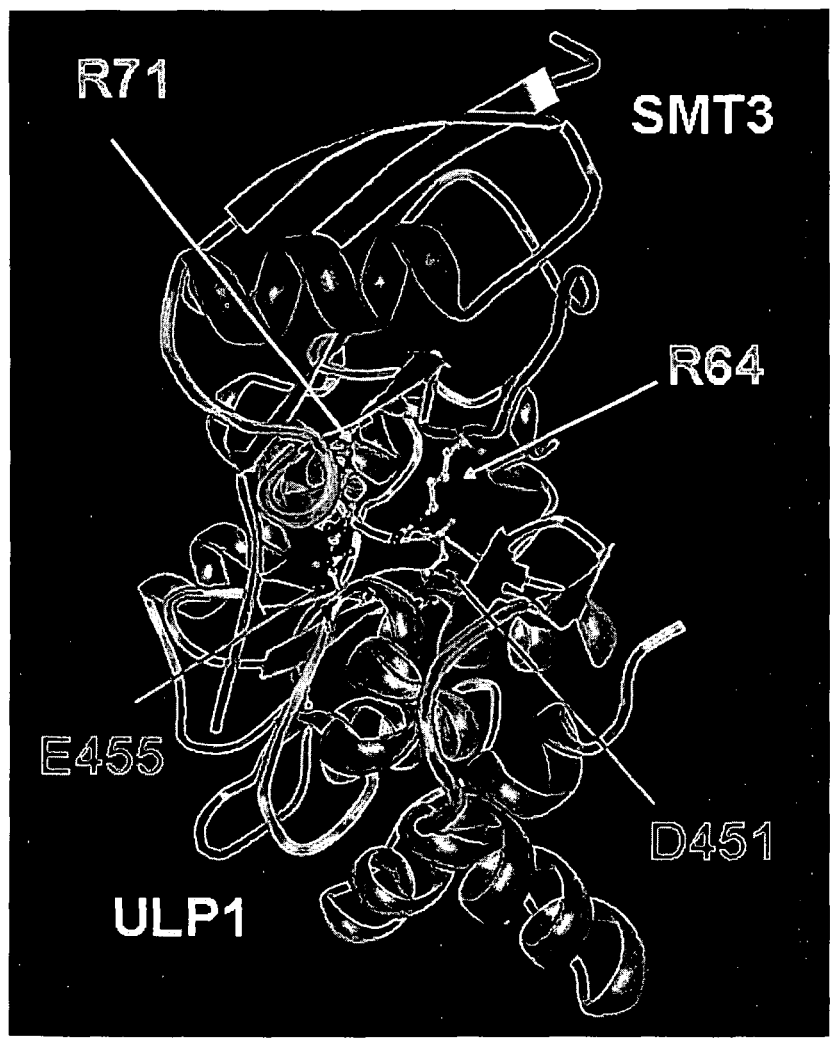
Figure 5:
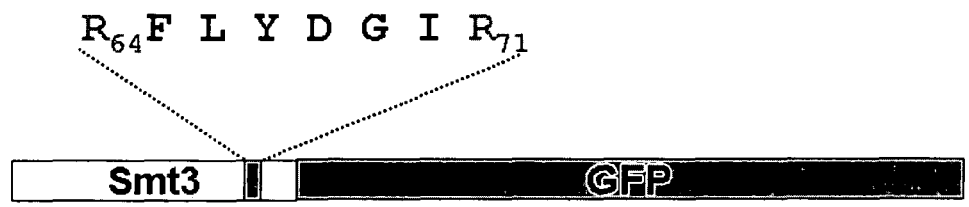
FIG. 5 is an illustration of a region of SUMO which is predicted to interface with ULP1. Arginines at position R64 and R71 are highlighted. SEQ ID NO: 66 is provided.

After evaluating the crystal structure of Smt3 and its corresponding protease Ulp1 (Protein Data Bank #1EUV) (FIG. 4), the region of Smt3 protein which appeared to interact with Ulp1 was mutagenized (FIG. 5). First, the region encoding amino acids 64-71 was randomized using general PCR mutagenesis techniques. Then, because arginines at positions 64 and 71 (R64 and R71) directly face Ulp1 (FIGS. 4A and 4B), these residues were specifically mutagenized by PCR mutagenesis. The resultant SUMO-GFP mutants were screened using a novel in vivo to cutting assay, namely E. coli transformed with Ulp1.

One mutant that exhibited no cleavage in the presence of ULP1 in vivo in E. coli comprises a threonine in place of the arginine at position 64 and a glutamic acid in place of the arginine at position 71. This particular mutant is referred to herein as SUMO*. Certain SUMO mutants are provided below in Table 1.

TABLE 1

Amino acid changes at positions R64 and R71 of certain mutants of SUMO and their ability to be cleaved by ULP1.

| Name | Modification to R64 and R71 | % Cleavage with ULP1 |
|---|---|---|
| wild-type | none | 100% |
| 1A3 | R64 -> Q | 10% |
| 1C1 | R64 -> L | 10% |
| 2E4 | R64 -> T; R71 -> E | 0% |
| 2E11 | R64 -> F; R71 -> E | 0% |
| 2F4 (SUMO*) | R64 -> T; R71 -> E | 0% |

As seen in FIGS. 3A and 3B, SUMO-GFP was almost fully cleaved by yeast and insect SUMO proteases, respectively, while SUMO*-GFP remained uncleaved. Additionally, the SUMO* fusion greatly enhances the expression of GFP compared to untagged GFP (compare lanes 1 and 2 with 5 and 6).

Figure 3:
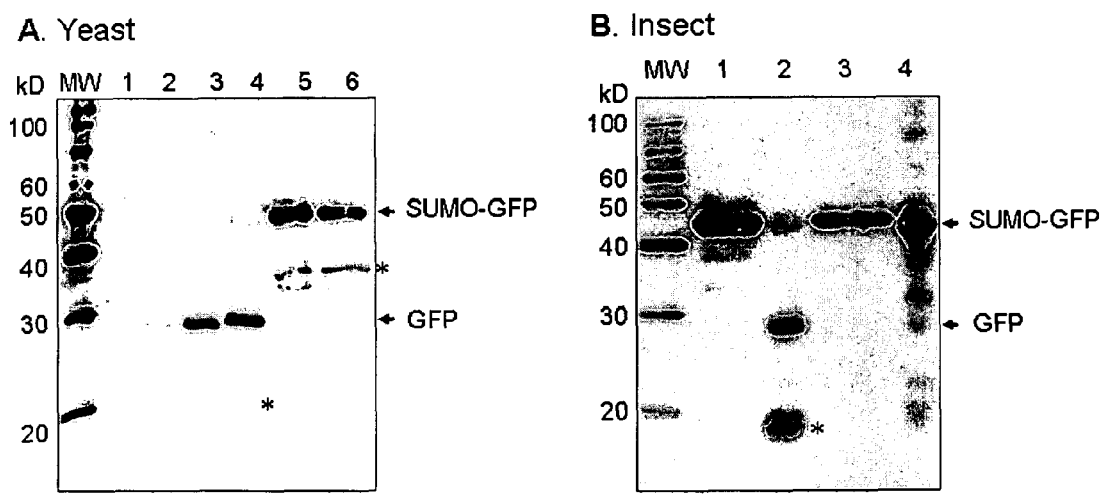
FIGS. 3A and 3B are images of Western blots showing that the SUMO* fusion tag is not cleaved by SUMO protease of the yeast Saccharomyces cerevisiae or by insect cell SUMO proteases, respectively. For FIG. 3A, yeast were transformed with constructs expressing GFP (lanes 1 and 2), SUMO-GFP (lanes 3 and 4) or SUMO*-GFP (lanes 5 and 6). For FIG. 3B, SUMO*-GFP or SUMO-GFP were incubated for 3 hours at 22° C. with (lanes 1 and 2) or without (lanes 3 and 4) insect Sf9 cell extract. Proteins were separated on 15% SDS-PAGE gel and detected by anti-GFP antibodies. *=GFP degradation product.
Figure 6:
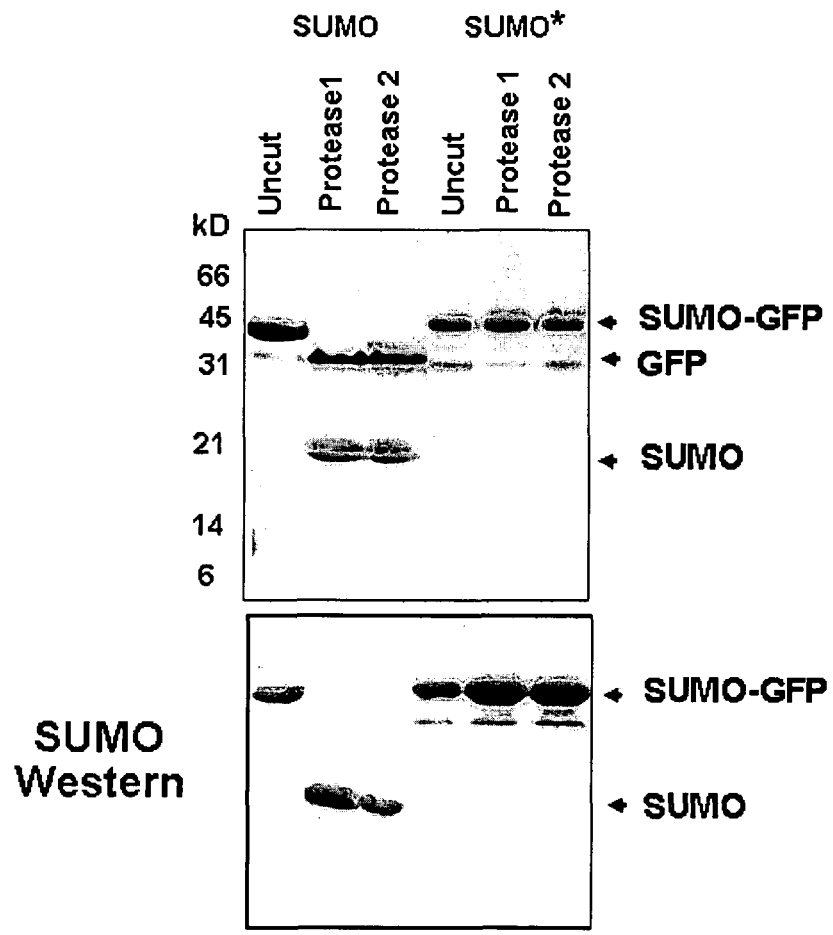
FIG. 6 provides images of a Coomassie stained SDS-PAGE (top panel) and an anti-Smt3 Western blot (bottom panel) of an identical gel demonstrating that wild-type SUMO (Smt3) is cleaved by ULP1 and SENP2 (SUMO protease 1 and 2) in vitro, but SUMO* (mutant Smt3) is not cleaved in vitro by either protease.
Figure 10:
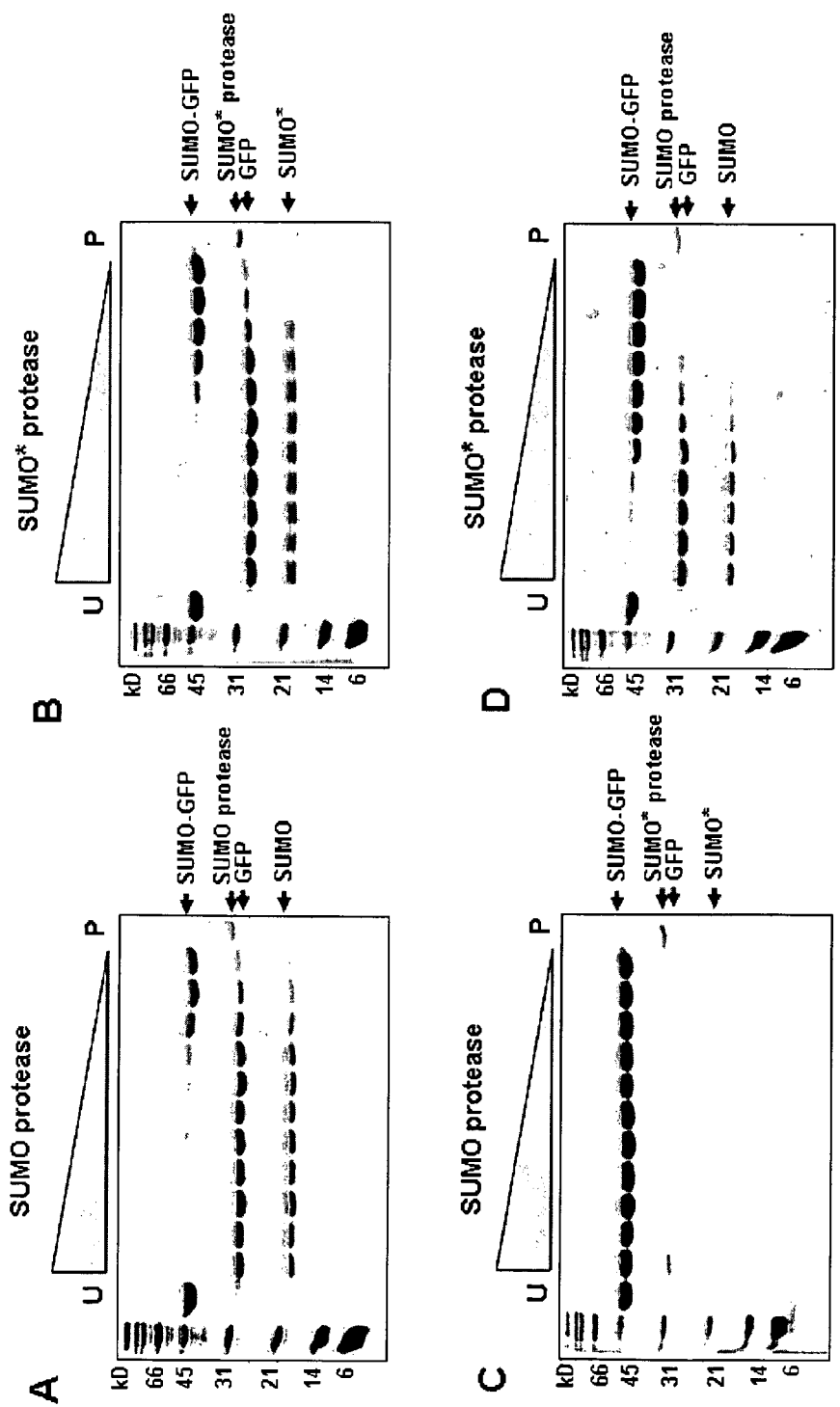
FIGS. 10A-10D are images of Coomassie stained SDS-PAGE gels demonstrating that SUMO* protease efficiently cleaves SUMO* from a fusion protein with GFP, but ULP1 does not cleave the SUMO* tag. The ramps indicate a protease titration where each consecutive lane contains two-fold less protease than the lane before.

SUMO*-GFP was purified and subjected to in vitro cleavage reactions. Both, SUMO protease 1 (Ulp1) and SUMO protease 2 (SENP2) were tested (FIG. 6). Neither protease cleaved SUMO* (FIG. 6). Indeed, SUMO* tagged fusions were incubated with increasing amounts of Ulp1 up to 1000 fold excess of the enzyme concentration required to fully cleave SUMO and still no cleavage was detected (FIG. 10). Additionally, when SUMO*-GFP was expressed in yeast or insect cells the mutated tag, unlike the wild type Smt3 tag, was not cleaved off by the natural SUMO proteases of either organism (FIG. 3).

Figure 8:
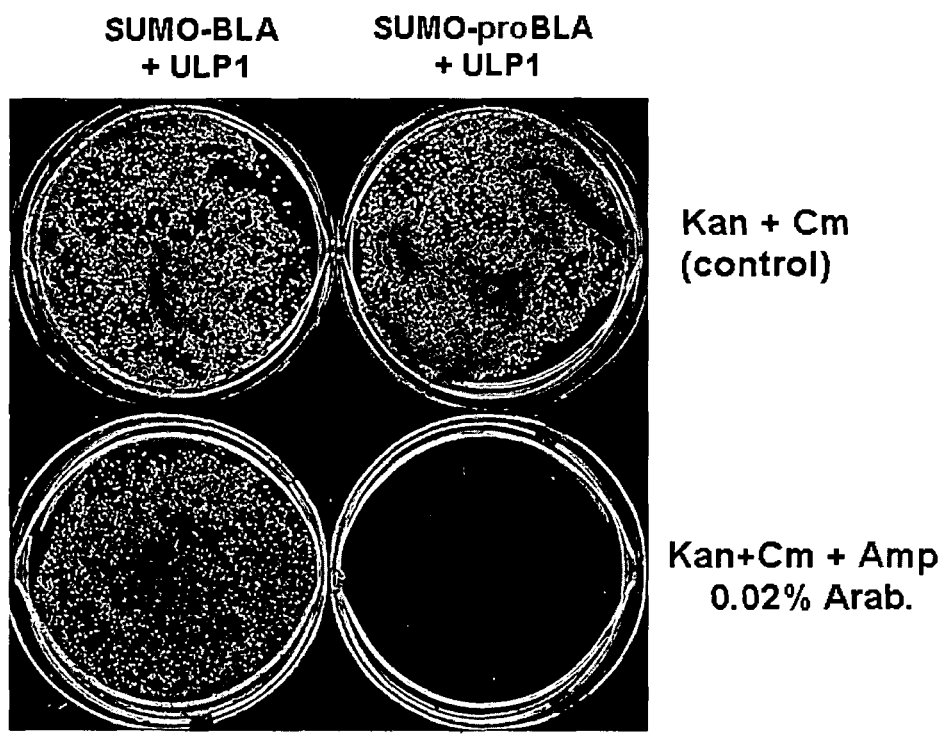
FIG. 8 are images of cultures of the in vivo β-lactamase screen demonstrating that E. coli does not grow on ampicillin when the protease can not cleave the SUMO containing substrate. For protease induction, plates were supplied with 0.02% arabinose.

In order for a fusion-tag to be optimal, it must have the ability to be removed in subsequent purification steps, leaving only the protein of interest. To engineer a protease that would cleave the SUMO* tag, hydrolases were screened for their ability to cleave mutant SUMOs from their fusion partners in E. coli (FIG. 7). The screen is based on the ability of E. coli to grow on media containing the antibiotic ampicillin if the ampicillin resistance protein, β-lactamase, is expressed in the cell. It has been demonstrated that only unfused β-lactamase can confer ampicillin resistance. Accordingly, if a SUMO tag was fused to β-lactamase, it would not confer ampicillin resistance. β-lactamase was fused to the C-terminus of SUMO* and expressed in concert with various hydrolases. Only when the tag was cleaved could β-lactamase be released in its active form, thus allowing the cells to live by conferring ampicillin resistance. It is known that if a protein starts with proline, then the SUMO-protein fusion is not cleaved by Ulp1. Therefore Smt3-pro-BLA fusion protein, a fusion where first amino acid after the Smt3 tag is proline, was constructed as a proof of concept for the screen (FIG. 8).

Figure 9:
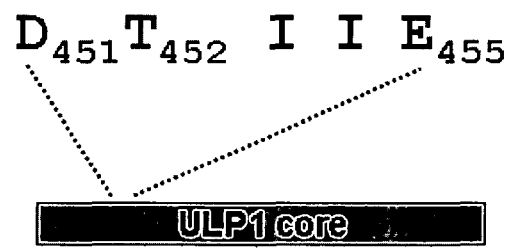
FIG. 9 provides a schematic illustration of the region in wild-type SUMO protease ULP1 and certain specific residues which restored enzymatic activity against SUMO* when mutated. SEQ ID NO: 24 is provided.

Analyzing the structure of Ulp1, the amino acid residues that interact with the SUMO amino acids R64 and R71 were determined to lay in the region between residues 450 and 456. The potential amino acids that interact with R64 and R71 are aspartic acid and glutamic acid at positions 451 and 455, respectively, as well as threonine at position 452 (FIGS. 4 and 9). These three residues in Ulp1 were randomly mutated using the PCR saturation mutagenesis technique. After mutagenesis, the mutants were selected on ampicillin containing plates using the in vivo β-lactamase assay. Ulp1 mutants were identified in the screen with varying degrees of cutting efficiency. The most efficient, mutant 2.2, was chosen and termed "SUMO* protease 1" (FIG. 10). Exemplary mutants are provided below in Table 2.

TABLE 2

Amino acid sequence between positions 451 and 455 in the wild-type ULP1 and certain mutants and their ability to cleave SUMO*.

| Name | Sequence of residues 451 to 455 (SEQ ID NO) | % Cleavage of SUMO* tag |
|---|---|---|
| wild-type | -D T I I E- (24) | 0% |
| mut 2.2 (SUMO* protease) | -S G I I S- (25) | 100% |
| mut 2.3 | -A M I I A- (26) | 10% |
| mut 1.38 | -S T I I A- (27) | 75% |
| mut 1.48 | -S T I I M- (28) | 75% |

Example II

Figure 13:
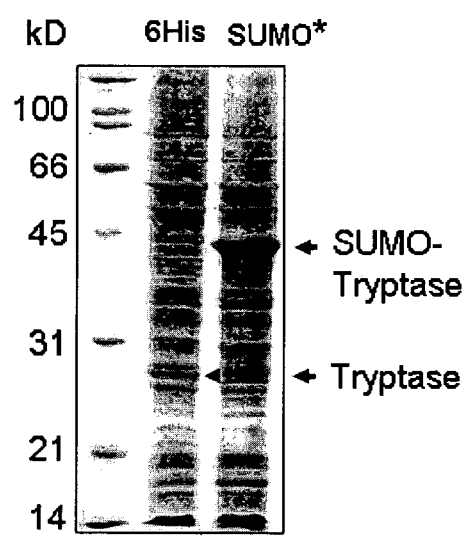
FIG. 13 is an image of a Coomassie stained SDS-PAGE gel demonstrating that SUMO* tagged tryptase is expressed at higher levels than the 6×His-tagged tryptase in insect cells and is not cleaved.

As with wild-type SUMO, engineered SUMOs are capable of increasing the expression of heterologous proteins. Indeed, FIG. 3A demonstrates that GFP is expressed to higher levels in Saccharomyces cerevisiae when the protein is fused to SUMO* as compared to untagged GFP. Additionally, FIG. 13 provides evidence that SUMO* enhances expression of heterologous proteins in insect cells. Specifically, tryptase was cloned into pFastBac vector with either a 6×His tag or SUMO* tag. The fusion proteins were expressed in insect sf9 cells. The Coomassie stained SDS-PAGE gel of the intracellular proteins clearly demonstrates that the enhanced expression of SUMO*-Tryptase as compared to 6×His-tagged tryptase. Notably, the SUMO*-tryptase fusion is not cleaved in insect cells.

Figure 14:
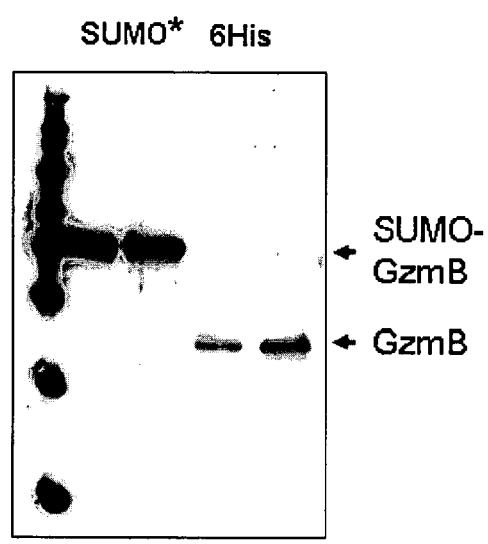
FIG. 14 is an image of a Western blot demonstrating that SUMO* tagged GzmB is expressed and secreted at higher levels than the 6×His-tagged GzmB in Pichia cells and is not cleaved.

Additionally, engineered SUMOs of the instant invention increase the secretion of heterologous proteins similarly to wild-type SUMO. FIG. 14 is a Western blot of the media proteins from Pichia pastoris expressing Granzyme B (GzmB) with a 6×His tag or GzmB fused to SUMO*. The media was separated from the cells and analyzed by SDS-PAGE and Western blot analysis using anti-GzmB antibodies to visualize SUMO*-GzmB and 6×His-GzmB. Notably, the SUMO*-GzmB fusion is not cleaved in Pichia cells.

Example III

Insect expression vectors were based on pFastBac (Invitrogen, Carlsbad, Calif.) and were made in two steps, similar to *Pichia*. First, 6×His, SUMO and SUMO* fusion tags were cloned behind the P-polh promoter. Then UBP43, a ubiquitin protease (Liu et al. (1999) Mol. Cell. Biol., 19: 3029-3038), was inserted in frame with the fusion tags into BsmBI-XbaI predigested vectors. Mouse UBP43 was amplified with primers: #265 (CGCGACCTGCATCGAGG-TATGGGCAAGGGGTTTGGGCTCCTGAGG; SEQ ID NO: 29) and #266 (CGCGACCTGCATGTCTAGATTAG-GATCCAGTCTTCGTGTAAACCAAG; SEQ ID NO: 30), digested with BfuAI. The bacmids were created in DH10bac *E. coli* cells. After obtaining and titrating the virus, the sf9 cells were transfected and the samples were analyzed for protein production after 72 hours.

For mammalian expression pcDNA3.1 vector was used. The mouse IgG kappa secretion signal and the three protein tags, 6×His, 6×His-SUMO, and 6×His-SUMO*, were cloned into the HindIII-BamHI sites behind the CMV promoter. The mouse secreted group X PLA2 was amplified with the primers 576 (ATCACGTCTCGAGGTGGACTCCTG-GAGCTGGCAGGGAC; SEQ ID NO: 31) and 285 (GCATCGTCTCACTAGTCAATTGCACTTGGGAGAGT; SEQ ID NO: 32), digested with BsmBI restriction endonuclease and cloned behind either 6×His, or SUMO, or SUMO* fusion tags. JOSD2 was expressed intracellularly without the kappa secretion tag. The JOSD2 open reading frame was amplified with DNA oligos 344 (ATGATGGGTCTCAAGG-TATGTCCCAGGCCCCGGGAGCA; SEQ ID NO: 33) and 345 (ATGATGGGTCTCTCTAGATCAGTCTGTC-CGCAGCCA; SEQ ID NO: 34) and cloned behind either 6×His or SUMO* tags into the pcDNA3.1 based vector.

2.5 micrograms of each purified plasmid was used to transfect each well of a 6 well plate containing HEK293T cells in 2 ml media. After 48 hours the cell and media samples were collected and analyzed by Western blotting.

Figure 15A:
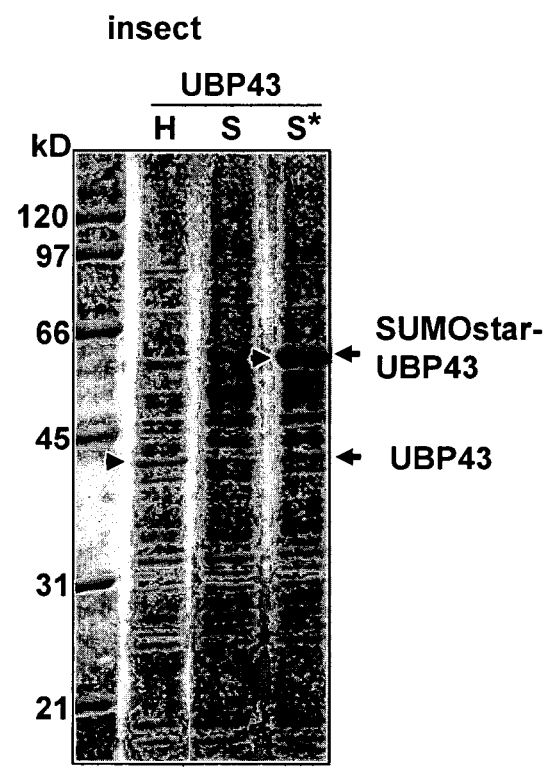
FIG. 15A is an image of a Coomassie stained SDS-PAGE gel showing a drastic enhancement of a heterologously expressed UBP43 protein by SUMO* fusion in insect sf9 cells. Arrows pinpoint the unfused or SUMO* fused UBP43 sizes.
Figure 15B:
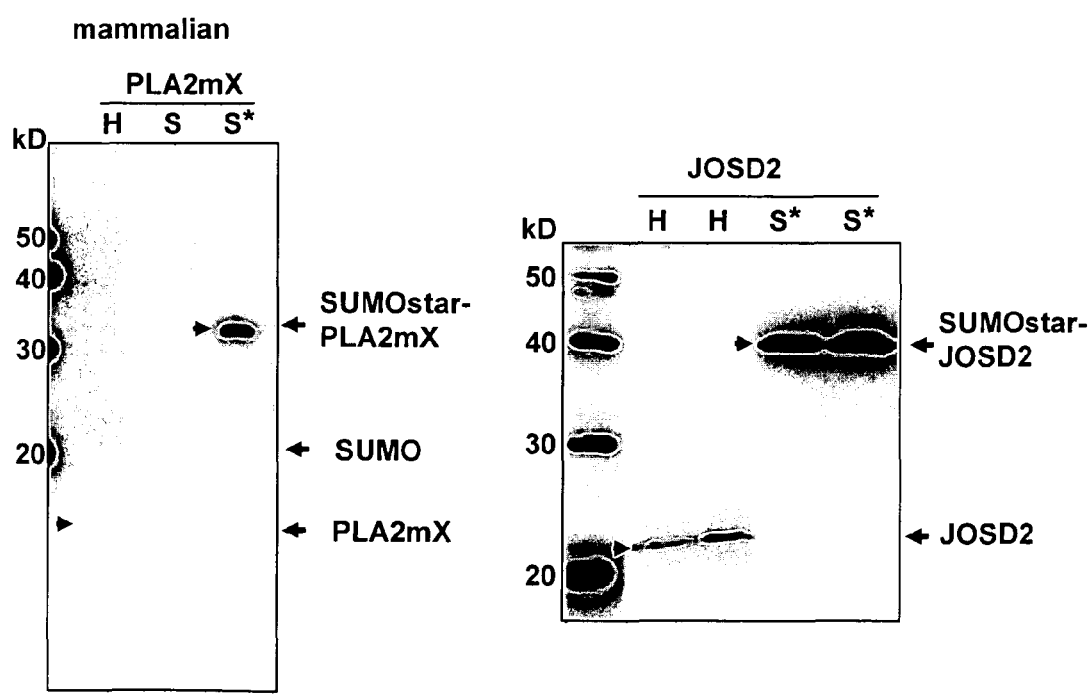
FIG. 15B provides images of Western blots showing the expression of mouse group X phospholipase 2A (mX PLA$_2$; left panel) and a deubiquitinase JOSD2 (right panel) in HEK293T cells. Only the PLA$_2$ fusion with SUMO* is secreted to the media, whereas the fusions with 6×His and wild-type SUMO are not. The 6×His-PLA$_2$ and fully cleaved SUMO-PLA$_2$ are barely detectable in the cell extract. Arrows pinpoint to the expected size of PLA$_2$, cleaved off wild-type SUMO, and SUMO*-PLA2. JOSD2 is expressed intracellularly and SUMO* greatly enhances its expression. H=6×His; S=SUMO; and S*=SUMO*.

As seen in FIGS. 15A and 15B, SUMO* fusion tag enhances the expression of fusion partner proteins and is not cleaved off in insect and mammalian cells.

Example IV

The sPLA$_2$ enzymes are marked by their catalysis of the sn-2 ester bond of phospholipids, a hydrolytic reaction. Following hydrolysis, lysophospholipid and free fatty acid result. These fatty acids can act as second messengers in signal transduction, while lysophospholipid notably aids in phospholipid remodeling.

PLA$_2$ was first discovered in 1890 in cobra venom (Six and Dennis (2000) Biochim. Biophys. Acta., 1488:1-19). Currently 11 different sPLA$_2$ groups have been identified in mice, classified on the basis of amino acid sequence homology and structural similarity. Of the 11 groups known, groups IIC, IIE, III, V, and X were implemented in these studies. (Letters correspond to different homologs of a particular group.) Group IIC, with 8 disulfide bonds, is found in rodent testis, brain, and pancreas, but is not expressed in humans (Six and Dennis (2000) Biochim. Biophys. Acta., 1488:1-19). Group IIE, with an inflammatory response in vivo, is found in humans (lung tissue) and mice (brain, heart, and liver tissue). Interestingly, group III, originally isolated from bee venom, induces dendrite maturation in humans, but is also expressed highly in pathologic endothelial human cells and appears to increase angiogenesis in tumor cells (Murakami et al. (2005) J. Biol. Chem., 280:24987-24998). Group V PLA$_2$, a 14 kDa protein with 6 disulfide bonds, has no unique loops in its structure and is expressed in rat and human heart in the presence of inflammatory stimuli (Six and Dennis (2000) Biochim. Biophys. Acta., 1488:1-19). Group X, the last of the analyzed PLA$_2$s, contains 123 amino acids and has 27-35% sequence identity to groups I, II, and V. It is found in the spleen, leukocytes, lung alveolar tissue, and thymus of humans, and in the stomach of mice. Like most PLA$_2$s, group X PLA$_2$s are present upon inflammatory stimuli and are also involved in signal transduction.

Many eukaryotic proteins require a complex translational and posttranslational environment for correct folding and activity. These conditions are not present in organisms like *E. coli* or yeast, which can lead to in incorrect processing and/or poor yield during attempts at recombinant expression in these hosts. The secreted phospholipase A$_2$s are a difficult family of proteins to produce in *E. coli.*, often being expressed in inclusion bodies. In addition, due to a relatively high number of disulfide bonds, typically between 5 and 8, the PLA$_2$s are difficult to refold, following solubilization. Expression is usually low and the subsequent refolding procedures often result in poor yields. Despite elegant protocols and laborious efforts, refolded protein activity can deviate from that of its natural version, making proper characterization evasive. Previous attempts to express sPLA$_2$s in mammalian cells have generally resulted in low expression levels. However, as described herein, the expression of heterologous proteins can be enhanced in *E. coli, P. pastoris*, and a baculovirus/insect cell system through fusion to members of the small ubiquitin-like modifier (SUMO) family. Accordingly, it was postulated that an approach similar to those done previously may lead to enhanced sPLA2 production in mammalian cells, specifically mouse PLA$_2$ groups.

Additionally, a free N-terminus of PLA$_2$ is essential for the biological activity of the PLA family of proteins. The production of active PLA$_2$ is deleterious to cells and overproduction of active PLA$_2$ kills the cells. Fusion proteins comprising an engineered SUMO at the N-terminus of PLA$_2$ are not cleaved in the cell allowing dormant/inactive PLA$_2$ to accumulate intracellularly or be secreted in the media (extracellular). The engineered SUMO-PLA$_2$ fusion can then be purified and cleaved with an engineered SUMO protease in vitro to produce active PLA$_2$ protein. Therefore, engineered SUMO fusions provide a superior means by which to express active toxic proteins, particularly when the toxicity of the protein is related to the N-terminus of the protein. Notably, other proteins such as trypsin, factor X, thrombin, and granzyme B can be toxic to a cell when overexpressed and require a free N-terminus for activity. Like PLA$_2$, these proteins can be readily expressed as an engineered SUMO fusion and then freed from the SUMO tag with an engineered SUMO protease.

Materials and Methods
Construction of Fusion Tag Vectors

For all vector constructs pcDNA3.1/V5-His (Invitrogen) was utilized as a backbone. Platinum Taq DNA Polymerase High Fidelity (Invitrogen) was used for all PCR reactions, while all restriction enzymes and T4 DNA ligase were from Fermentas (Burlington, Ontario, Canada). Cloning was performed according to standard techniques. All clones were verified by sequencing. Initially a kappa S.S. and 6×His tag were generated via overlapping primers with a region of homology between the two (primers 1+2 and 3+4, respectively; see Table 3 for primer sequences). The kappa S.S and His tag were joined in a secondary PCR reaction using primers 1+4. The kappa-6×His fusion was inserted into pcDNA3.1 via HindIII and BamHI restriction sites, generating pcDNA3.1-kappa-6×His. Primers 3 and 4 were designed so that the His tag was followed by two glycines and an Esp3I/BsmBI restriction site on the opposite strand, upstream of the BamHI site. Digestion with Esp3I generated a four base overhang on the non-coding strand which consisted of tcca from the di-glycine ggaggt coding sequence. CTHS, SUMO, SUMOmut and hSUMO3 were amplified with primers 5+6, 7+6, 7+6 and 8+9, respectively. All reverse primers recreated the Esp3I recognition site downstream of the various SUMO terminal di-glycine codons, while employing a second Esp3I recognition site downstream. SUMO tags were inserted into pcDNA3.1-kappa-6×His via Eco31I and BamHI restrictions sites generating the following vectors: pcDNA3.1-kappa-6× His-CTHS, pcDNA3.1-kappa-6×His-SUMO, pcDNA3.1-kappa-6×His-SUMOmut, pcDNA3.1-kappa-6×His-hSUMO3.

Initial Mouse sPLA$_2$-X Construct Creation

Active sPLA$_2$-X was PCR amplified using primers 10+11. Inactive sPLA$_2$-X was PCR amplified from the same clone using primers 12+11. Both active and inactive sPLA$_2$-X constructs were created by digesting both PCR product and vectors with Esp3I.

Expansion of Fusion Tag Vectors

Human SUMO-1 was PCR amplified from cDNA using primers 13+14 and cloned into pcDNA3.1-kappa-6×His via Esp3I and XbaI restrictions sites generating pcDNA3.1-kappa-6×His-hSUMO1. Mutant human SUMO-1 and 3 were generated using PCR site-directed mutagenesis in which the N-terminal and C-terminal halves were produced in separate reactions, gel isolated, and joined in a subsequent PCR reaction. Human SUMO-1 primary PCR used primers 13+15 and 16+14 for the N and C-terminal reactions, respectively. Human SUMO-3 primary PCR used primers 8+17 and 18+9 for the N and C-terminal reactions, respectively. In the secondary PCR purified primary products were mixed for each human SUMO and primers 13+14 were used for hSUMO1mut while primers 8+9 were used for hSUMO3mut. Products were inserted into pcDNA3.1-kappa-6×His generating pcDNA3.1-kappa-6×His-hSUMO1mut and pcDNA3.1-kappa-6×His-hSUMO3mut.

Expansion of Mouse sPLA$_2$ Constructs cDNAs for mouse sPLA2-IIC, IIE, III and V were purchased from Open Biosystems (Huntsville, Ala.). PLA$_2$ primers were designed with the goal of generating mature proteins subsequent to purification and tag removal. Secretory signals and propeptides were therefore omitted in primer design, based on literature review and SignalP analysis. Mouse sPLA$_2$-IIC was cloned from cDNA, corresponding to GenBank entry BC029347, with primers 19+20. Mouse sPLA$_2$-IIE was cloned from cDNA, corresponding to GenBank entry BCO$_{27524}$, with primers 21+22. Full length mouse sPLA$_2$-III was cloned from cDNA, corresponding to GenBank entry BC079556, with primers 23+24. Mouse sPLA$_2$-V was cloned from cDNA, corresponding to GenBank entry BC030899, with primers 25+26. The active domain of mouse sPLA2-III (Murakami et al. (2005) J. Biol. Chem., 280:24987-24998) was cloned from cDNA, corresponding to GenBank entry BC079556, with primers 27+28. All sPLA$_2$ genes including sPLA$_2$-X active and inactive were sub-cloned into pcDNA3.1-kappa-6×His, pcDNA3.1-kappa-6×His-SUMO, pcDNA3.1-kappa-6×His-SUMOmut, pcDNA3.1-kappa-6×His-hSUMO1, pcDNA3.1-kappa-6×His-hSUMO1mut, pcDNA3.1-kappa-6×His-hSUMO3 and pcDNA3.1-kappa-6×His-hSUMO3mut.

Transient Transfection in HEK-293 Cells

HEK-293T cells were seeded into 6 well plates (Becton Dickinson; Sparks, Md.) at a density of 500,000 cells per well in a DMEM containing 10% Fetal Bovine Serum media and incubated overnight at 37° C. with 95% air/CO$_2$. Cells were transiently transfected with various PLA2 cDNA constructs in pcDNA3.1 vector (2.5 µg/well) using the Lipofectamine-LTX as described by the manufactures (Invitrogen). After transfection, cells were then incubated for additional 48 hours at 37° C. before being analyzed for PLA$_2$ expression.

Expression Analysis

After 48 hours of incubation, following transfection, media and cells was collected for analysis. Culture media was removed from each well (~1.5 ml) and debris was separated by centrifugation. For SDS-PAGE/Western blotting 100 µl of media was mixed with 6×SDS loading buffer and boiled for 5 minutes. The remaining media was stored at −80° C. for later assay. Cells were washed from each well of the plate, separated by centrifugation, re-suspended in 180 µl cold RIPA buffer, sonicated briefly, mixed with 6×SDS loading buffer and boiled for 5 minutes. All samples were resolved on denaturing 15% acrylamide gels with a 4% acrylamide stacking layer. Gels were transferred to Immoblin™ nitrocellulose (Millipore; Billerica, Mass.) using a Trans-Blot® SD semi-dry transfer cell (BioRad; Hercules, Calif.). After transfer, blots were blocked with 5% non-fat milk in PBS pH 7.5+ 0.05% Tween-20 (PBST) for one hour. Following blocking, the blots were incubated in 1:1000 monoclonal Anti-His Antibody (Sigma) in PBST+milk for one hour. Blots were washed with PBST three times and incubated with 1:2500 anti-mouse HRP conjugated antibody (Sigma; St. Louis, Mo.) in PBST+ milk for one hour. Blots were again washed three times with PBST. HRP conjugates were detected with SuperSignal® West Pico chemoluminescent substrate (Pierce; Rockford, Ill.). Blots were imaged using a LAS-3000 (Fujifilm Life Science; Stamford, Conn.).

TABLE 3

Primers

|   | Gene | Sequence | Enzyme(s) | SEQ ID NO | Dir. |
|---|------|----------|-----------|-----------|------|
| 1 | kappa | GCGCAAGCTTGCTATGGAG ACAGACACACTCCTGCTAT GGGTACTGCTGCTCT | HindIII | 35 | F |
| 2 | kappa | GATGATGGTGATGACCGTC ACCAGTGGAACCTGGAACC CAGAGCAGCAGTACCCA |  | 36 | R |
| 3 | 6xHis | CCAGGTTCCACTGGTGACG GTCATCACCATCATCATCA CGGAGGT |  | 37 | F |
| 4 | 6xHis | CGCGTCTAGAGAGACGGCA TGCCGTCTCAACCTCCGTG ATGATGATGGTGATG | XbaII, Esp3I | 38 | R |
| 5 | CTHS | CGC AGGTCTCTAGGTGAAA GACAGGGTAAGGAAATGGA | Eco31I | 39 | F |
| 6 | SUMO | CGCGTCTAGAGAGACGGCA TGCCGTCTCAACCTCCAAT CTGTTCGCGGTGA | XbaI, Esp3I | 40 | R |
| 7 | SUMO | CGCAGGTCTCTAGGTTCGG ACTCAGAAGTCAATCAAGA | Eco31I | 41 | F |
| 8 | hSUMO3 | CGCAGGTCTCTAGGTTCCG AGGAGAAGCCCAAGGA | Eco31I | 42 | F |
| 9 | hSUMO3 | CGCGTCTAGAGAGACGGCA TGCCGTCTCAACCTCCCGT CTGCTGCTGGAA | XbaI, Esp3I | 43 | R |
| 10 | sPLA$_2$-X | ATCACGTCTCGAGGTGGAC TCCTGGAGCTGGCAGGGAC | Esp3I | 44 | F |

TABLE 3-continued

Primers

| | Gene | Sequence | Enzyme(s) | SEQ ID NO | Dir. |
|---|---|---|---|---|---|
| 11 | sPLA₂-X | GCATCGTCTCACTAGATCA ATTGCACTTGGGAGAGT | Esp3I | 45 | R |
| 12 | sPLA₂-Xmut | ATCACGTCTCGAGGTCTCC TGGAGCTGGCAGGGAC | Esp3I | 46 | F |
| 13 | hSUMO1 | CGCAGGTCTCTAGGTTCTG ACCAGGAGGCAAAACCT | Eco31I | 47 | F |
| 14 | hSUMO1 | CGCGTCTAGAGAGACGGCA TGCCGTCTCAACCTCCCGT TTGTTCCTGATAA | XbaI, Esp3I | 48 | R |
| 15 | hSUMO1 mut | ATGATTATCAGCAATTTCC TGACCCTCAAAGAGAAACG TGAGTGAATTCATTGGAA | | 49 | R |
| 16 | hSUMO1 mut | CCAATGAATTCACTCACGT TTCTCTTTGAGGGTCAGGA AATTGCTGATAATCATAC | | 50 | F |
| 17 | hSUMO3 mut | TGGCTGCCCGTCGAACTCG AATGTGATCTGCCTCATTG ACA | | 51 | R |
| 18 | hSUMO3 mut | TCAATGAGGCAGATCACAT TCGAGTTCGACGGGCAGCC AAT | | 52 | F |
| 19 | sPLA2-IIC | GCGCCGTCTCTAGGTAGTT TCTGGCAGTTCCAGAGGA | Esp3I | 53 | F |
| 20 | sPLA2-IIC | GCGCCGTCTCTCTAGATTA GCACTGGAGTTTGTCCCTG C | Esp3I | 54 | R |
| 21 | sPLA2-IIE | GCGCGGTCTCTAGGTAACC TGGTCCAGTTTGGAGTGA | Eco31I | 55 | F |
| 22 | sPLA2-IIE | GCGCGGTCTCTCTAGATTA GCAGGGTGGGGTGGGC | Eco31I | 56 | R |
| 23 | sPLA2-III | GCGCGAAGACATAGGTCGT CACTGGGACAGTACCTCCT G | BpiI | 57 | F |
| 24 | sPLA2-III | GCGCGAAGACATCTAGATT ATGAGCTCCAGAATTTCTT CTGTCC | BpiI | 58 | R |
| 25 | sPLA2-V | GCGCCGTCTCTAGGTGGCT TGCTAGAACTCAAGTCCAT G | Esp3I | 59 | F |
| 26 | sPLA2-V | GCGCCGTCTCTCTAGATTA GCAGAGGAAGTTGGGGTAA TAC | Esp3I | 60 | R |
| 27 | sPLA2-IIIcore | GCGCCGTCTCTAGGTGGCT GGACCATTCCTGGCACG | Esp3I | 61 | F |
| 28 | sPLA2-IIIcore | GCGCCGTCTCTCTAGATTA ATATGAGGTGGCCTCAGCC TTCCAG | Esp3I | 62 | R |

Results

To evaluate the potential utility of expressing SUMO-fusion proteins in the mammalian secretory pathway, mouse sPLA₂-X was used as a model protein. Initially the following four N-terminal fusions were tested: Smt3 (SUMO), the C-terminal half of Smt3 comprising AA45-99 (CTHS), a double mutant, Smt3 R64T R71E (SUMOmut (SUMO*)), which is uncleavable by SUMO proteases and human SUMO-3 (hSUMO3). All tags were created with a hexahistidine (6×His) N-terminus and directed for secretion using the IgG kappa secretory signal from mouse. For control purposes a vector was created with only the signal sequence and 6×His tag, creating a total of five vectors differing only in their SUMO based tag. Fusion to Smt3 has been shown to enhance the expression of heterologous proteins in *E. coli*, while fusion to human SUMO-3 resulted in enhanced expression in *E. coli* and *P. pastoris*. Certain expression data is provided in Table 4.

TABLE 4

| sPLA₂ | Tag | sPLA₂ Expression (wt tag) (mg/L) | sPLA₂ Expression (mut tag) (mg/L) |
|---|---|---|---|
| mGIIE | 6×His | 0.05 | |
| | 6×His-SUMO | 4.85 | 8.11 |
| | 6×His-hSUMO1 | 0.15 | 3.44 |
| | 6×His-hSUMO3 | 7.86 | 9.77 |
| mGIII | 6×His | 0.94 | |
| | 6×His-SUMO | 4.54 | 2.26 |
| | 6×His-hSUMO1 | 0.18 | 2.40 |
| | 6×His-hSUMO3 | 4.85 | 4.22 |
| mGV | 6×His | 0.28 | |
| | 6×His-SUMO | 0.43 | 2.16 |
| | 6×His-hSUMO1 | 0.77 | 3.06 |
| | 6×His-hSUMO3 | 0.78 | 6.50 |
| mGX | 6×His | 0.50 | |
| | 6×His-SUMO | 0.05 | 2.84 |
| | 6×His-hSUMO1 | 0.15 | 2.03 |
| | 6×His-hSUMO3 | 0.16 | 4.62 |

CTHS was developed initially for baculovirus/insect cell expression since it was observed that full length SUMO fusions were cleaved by endogenous desumoylases (see, e.g., PCT/US04/20778 and U.S. patent application Ser. No. 10/504,785). Based on the development of split-ubiquitin (Johnsson and Varshaysky (1994) PNAS 91:10340-10344), CTHS would only be cleaved in the presence of its N-terminal half (NTHS). It has been found that CTHS fusion enhances the production of fusion partners while avoiding endogenous cleavage.

As described herein, the mutant Smt3 was developed with the goal of creating a SUMO fusion, which in a eukaryotic host would not be cleaved in vivo, while maintaining all the positive enhancements of Smt3 fusion demonstrated in prokaryotes. Following extensive crystal structure analysis of Smt3 bound to its natural protease Ulp1, a rational mutagenesis screening campaign resulted in the modification of two interfacial amino acids. These modifications, R64T and R71E, resulted in a SUMO which could not be cleaved by Ulp1 regardless of enzyme concentration. In screening, the novel SUMO displayed an enhancement in the expression of its fusion partner equivalent to that obtained with wild-type Smt3. Following the generation of mutant Smt3, Ulp1 was also subjected to rational mutagenesis screening and a mutant enzyme was developed capable of cleaving mutant Smt3 fusions in vitro.

Figure 16:
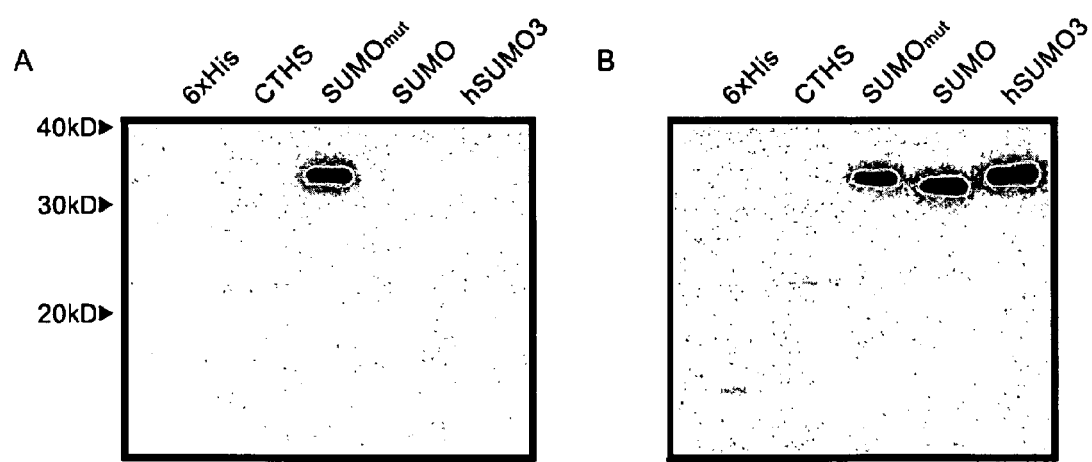
FIG. 16 provides images of Western blots of media (15 µl) from the initial mouse sPLA$_2$-X constructs (both active (FIG. 16A) and inactive (FIG. 16B) forms), 48 hours post transfection (HEK-293T). The following five N-terminal fusion tags were tested: 6×His, 6×His-CTHS, 6×His-SUMOmut, 6×His-SUMO, and 6×His-hSUMO3. All constructs also comprised the mouse IgG kappa secretory signal. Results are representative of at least 3 independent experiments.
Figure 17:
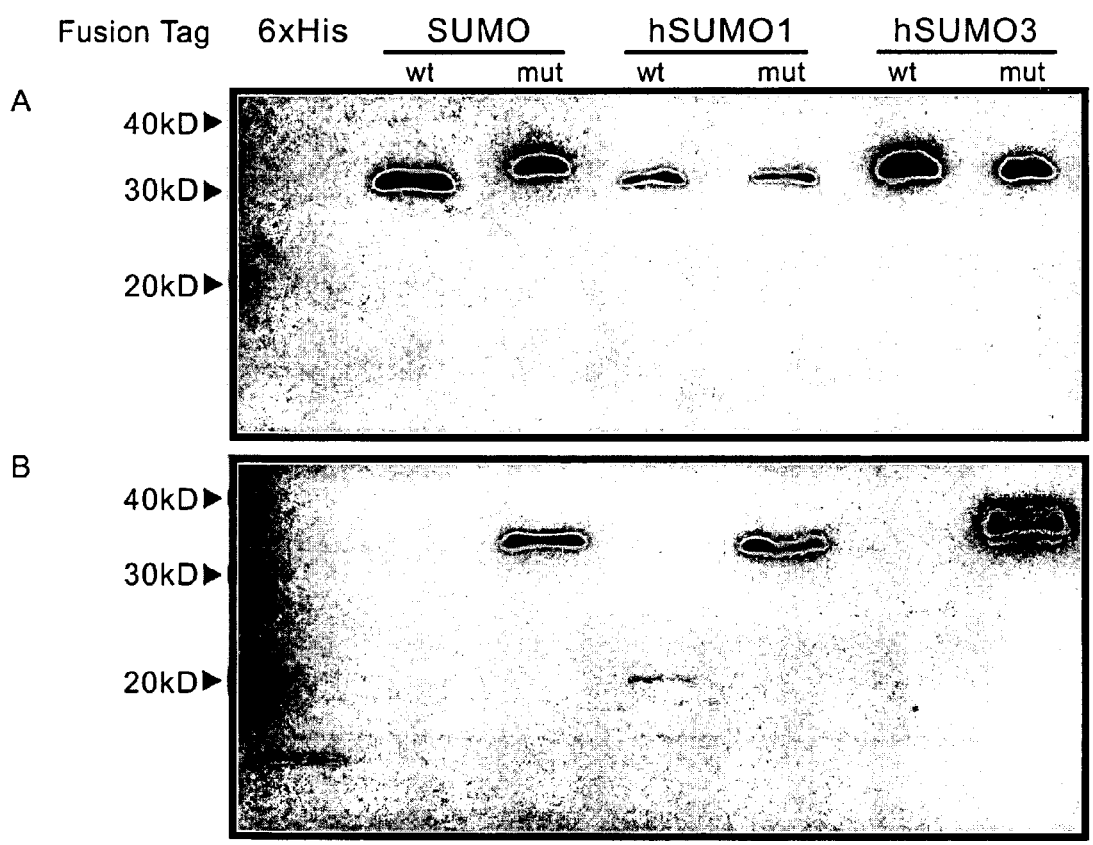
FIG. 17 provides images of Western blots of media (15 µl) from the revised mouse sPLA2-X constructs (both inactive (FIG. 17A) and active (FIG. 17B) forms), 48 hours post transfection (HEK-293T). The following seven N-terminal fusion tags were tested: 6×His, 6×His-SUMO, 6×His-SUMO mut, 6×His-hSUMO1, 6×His-hSUMO1 mut, 6×His-hSUMO3 and 6×His-hSUMO3 mut. All constructs comprised the mouse IgG kappa secretory signal. Results are representative of at least 3 independent experiments.
Figure 18:
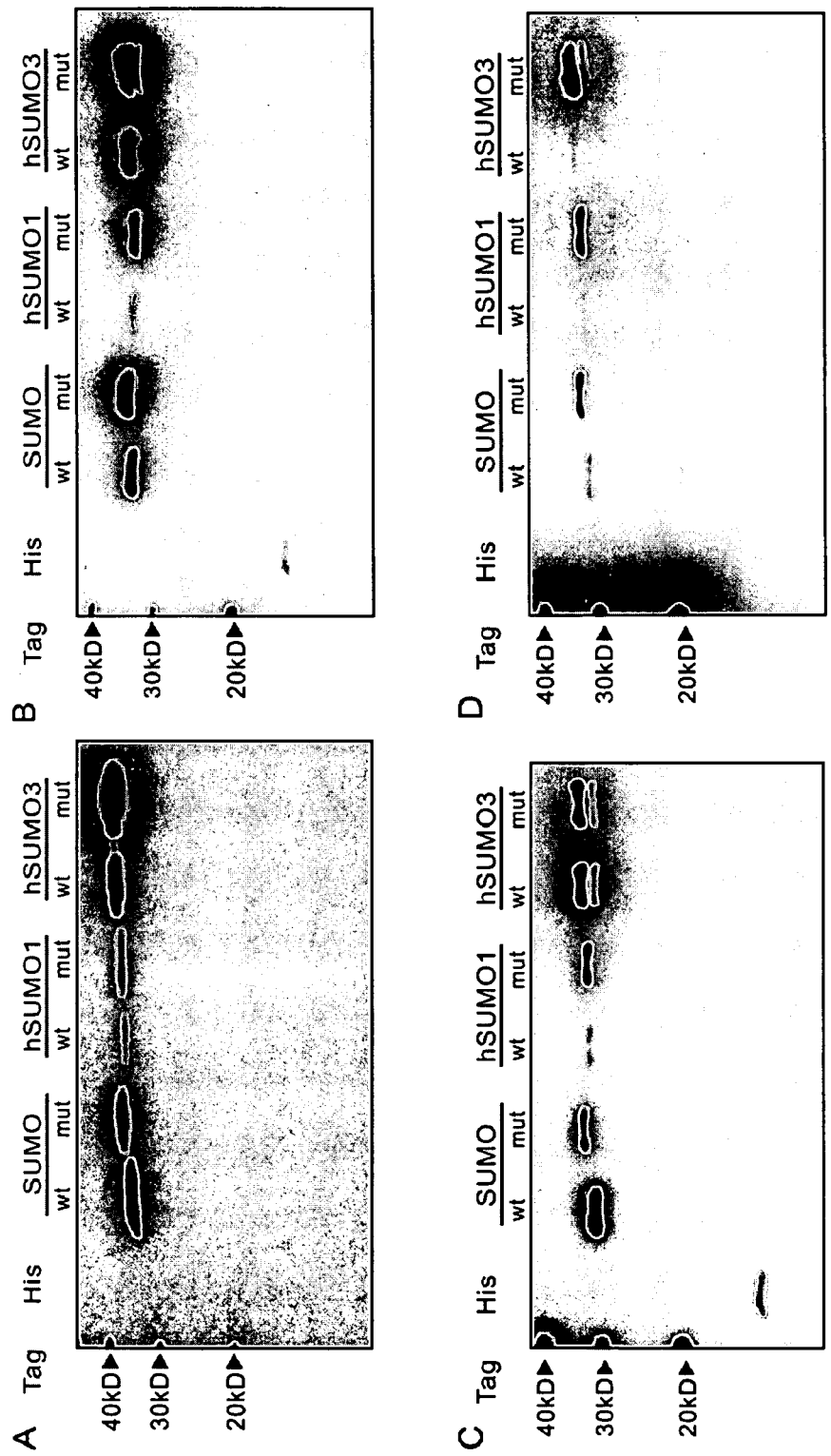
FIG. 18 provides images of Western blots of sPLA$_2$-IIC (FIG. 18A, intracellular fraction), IIE (FIG. 18B, media (15 µl)), III (media (15 µl)), and V (media (15 µl)) constructs, 48 hours post transfection (HEK-293T). Comparisons were made for each sPLA$_2$ by using the three SUMOs in both mutant and wild-type forms with a 6×His tag serving as the control. All constructs comprised the mouse IgG kappa secretory signal. Results are representative of 2-3 independent experiments.

Expression of sPLA₂-X in HEK-293T cells can be seen in FIG. 16A. SUMOmut clearly shows an enhancement in the production of sPLA₂-X compared to the other tags; however the Smt3 and hSUMO3 cultures appeared to be less confluent at the end of 48 hours. The transfection was repeated several times with the same results. sPLA₂-X is naturally produced as a zymogen and the mature form was cloned behind the various tags. The overexpression of sPLA₂-X may be toxic to the cells in a scenario were it could be released from its fusion partner. To evaluate whether the proposed toxicity of sPLA₂-X was a result of cleavage, a series of inactive $sPLA_2$-X fusions were generated by omitting the N-terminal glycine of $sPLA_2$-X. Expression of those fusions with inactive $sPLA_2$-X in HEK-293T cells can be seen in FIG. 16B. The results demonstrate that, although no cleavage product is visible, $sPLA_2$-X activity and the susceptibility of its N-terminal pro-peptide to cleavage clearly plays a role in over-expression.

A comparison of the crystal structures of human SUMO-1, 2, 3 and Smt3 reveals a strong conservation between SUMO structures with nearly identical locations of the two interfacial arginine residues. Notably, SUMO-2 and 3 share 97% identity. Accordingly, hSUMO-1 and 3 were investigated with the expectation that SUMO-2 would behave the same SUMO-3. In hSUMO1, the arginine at position 63 was changed to a threonine (R63T) and the arginine at position 70 was changed to a glutamic acid (R70E). For hSUMO3, the arginine at position 58 was changed to a threonine (R58T) and the arginine at position 60 was changed to a glutamic acid (R60E). Active and inactive $sPLA_2$-X fusions were made with the mutant and wild-type versions of Smt3, hSUMO1 and 3. The results of expressing the inactive and active fusions for 48 hours can be seen in FIGS. 17A and B, respectively. The cultures expressing wild-type Smt3, hSUMO1 and hSUMO3 again did not grow as well in addition to not expressing $sPLA_2$-X. This is likely due to the cleavage of the fusion protein and release of the toxic $PLA_2$. Interestingly some His-tagged hSUMO1 is visible in 17A while none can be seen in the other wild-type SUMO fusions with active $sPLA_2$-X.

Given the expression data using mouse $sPLA_2$-X, other $sPLA_2$ groups were tested. Four additional mouse $sPLA_2$ genes were tested based on their varied levels of recombinant expression previously reported (Rouault et al. (2007) Biochemistry 46:1647-1662). Mouse $sPLA_2$-IIC and III have previously been produced in insect cells with yields of 150 and 70 ng/L, respectively. There are currently no refolding protocols for either $sPLA_2$ and both enzymes are naturally glycosylated, making eukaryotic production a necessity. Mouse $sPLA_2$-IIE represents the lowest reported yield in bacterial production at 800 ng/L, while $sPLA_2$-V represents the highest yield at 20 mg/L. Mouse $sPLA_2$-X was expressed a 10 mg/L in *E. coli.*

The active versions of mouse sPLA2-IIC, IIE, III and V were tested. The intracellular expression of $sPLA_2$-IIC after 48 hours can be seen in FIG. 18A. His-tagged protein could not be detected in the media. Despite an apparently large increase in expression with all the SUMO tags, secretion was somehow inhibited. The expression and secretion of $sPLA_2$-IIE can be seen in FIG. 18B. After 48 hours, significantly more $sPLA_2$-IIE is visible in most of the SUMO fusions, with 140 times more SUMOmut and 190 times more hSUMO3mut than His-tag alone via densitometry analysis. Mouse and human $sPLA_2$-III is expressed as a 55 kD protein but often matures via post-translational and cell-specific proteolytic processing to a 28 kD active domain (Murakami et al. (2003) J. Biol. Chem., 278:10657-10667; Murakami et al. (2005) J. Biol. Chem., 280:24987-24998.). The active or S domain is preceded by an N domain and followed by a C domain. Initially, fusions with the full length $sPLA_2$-III were generated, only replacing is native secretory signal with SUMO and the kappa signal. In HEK-293 cells, all $sPLA_2$-III fusions were processed at their first cleavage point, dividing the N and S domains as seen in FIG. 18C, where the His tagged proteins are only 12 kD or approximately 32 kD with the various SUMOs. Intracellular blotting demonstrated the production of a 55 kD protein with no additional forms visible. The expression and secretion of $sPLA_2$-V can be seen in FIG. 18D. Similar to group X, there is a strong preference for the mutant SUMO fusions in the expression of $sPLA_2$-V. Although there was clearly a lack of expression in the wild-type SUMO fusions, similar cell culture problems were not seen in the case of $sPLA_2$-V.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. An isolated nucleic acid molecule encoding an engineered SUMO protease, wherein said engineered SUMO protease comprises a SUMO interaction domain comprising the amino acid sequence

WLNX$_1$X$_2$X$_3$X$_4$X$_5$  (SEQ ID NO: 6)

wherein X$_1$ and X$_5$ are any non-acidic amino acid and X$_2$, X$_3$, and X$_4$ are any amino acid, and
 wherein said engineered SUMO protease has at least 80% homology with an amino acid sequence selected from the group consisting of SEQ ID NO: 3 SEQ ID NO: 4, and SEQ ID NO: 5.

2. The isolated nucleic acid molecule of claim 1, wherein X$_1$ is serine and X$_5$ is selected from the group consisting of serine, alanine, and methionine.

3. The isolated nucleic acid molecule of claim 1, wherein X$_1$ is serine; X$_2$ is glycine; and X$_5$ is serine.

4. The isolated nucleic acid molecule of claim 1, wherein X$_2$ is selected from the group consisting of glycine and threonine; X$_3$ is isoleucine or valine; and X$_4$ is isoleucine or threonine.

5. The isolated nucleic acid molecule of claim 1, wherein said engineered SUMO protease is selected from the group consisting of SEQ ID NO: 3, SEQ ID NO: 4, and SEQ ID NO: 5.

6. An expression vector comprising the nucleic acid molecule of claim 1.

7. An isolated cell comprising the expression vector of claim 6.

8. The isolated nucleic acid molecule of claim 1, wherein said engineered SUMO protease has at least 80% homology with SEQ ID NO: 4.

9. The isolated nucleic acid molecule of claim 8, wherein said engineered SUMO protease has at least 90% homology with SEQ ID NO: 4.

10. The isolated nucleic acid molecule of claim 1, wherein X$_1$ and X$_5$ are selected from the group consisting of asparagine, glutamine, serine, threonine, tyrosine, alanine, glycine, valine, leucine, isoleucine, proline, phenylalanine, methionine, tryptophan, and cysteine.

11. The isolated nucleic acid molecule of claim 10, wherein X$_2$ is glycine or threonine, X$_3$ is isoleucine or valine, and X$_4$ is isoleucine or threonine.

12. The isolated nucleic acid molecule of claim 10, wherein X$_1$ is serine and X$_5$ is selected from the group consisting of serine, alanine, and methionine.

13. An isolated nucleic acid molecule encoding an engineered SUMO protease, wherein said engineered SUMO protease comprises a SUMO interaction domain comprising the amino acid sequence

WLNX$_1$X$_2$X$_3$X$_4$X$_5$  (SEQ ID NO: 6)

wherein:
 X$_1$ is serine; X$_2$ is glycine; X$_3$ is isoleucine; X$_4$ is isoleucine; and X$_5$ is serine;
 X$_1$ is alanine; X$_2$ is methionine; X$_3$ is isoleucine; X$_4$ is isoleucine; and X$_5$ is alanine;
 X$_1$ is serine; X$_2$ is threonine; X$_3$ is isoleucine; X$_4$ is isoleucine; and X$_5$ is alanine; or
 X$_1$ is serine; X$_2$ is threonine; X$_3$ is isoleucine; X$_4$ is isoleucine; and X$_5$ is methionine.

14. The isolated nucleic acid molecule of claim 1, wherein said engineered SUMO protease has at least 90% homology with an amino acid sequence selected from the group consisting of SEQ ID NO: 3 SEQ ID NO: 4, and SEQ ID NO: 5.

15. The isolated nucleic acid molecule of claim 13, wherein X$_1$ is serine; X$_2$ is glycine; X$_3$ is isoleucine; X$_4$ is isoleucine; and X$_5$ is serine.

* * * * *